United States Patent
Kim et al.

(10) Patent No.: US 10,361,377 B2
(45) Date of Patent: Jul. 23, 2019

(54) CONDENSED CYCLIC COMPOUND AND ORGANIC LIGHT EMITTING DEVICE INCLUDING THE SAME

(71) Applicants: SAMSUNG SDI CO., LTD., Yongin-si, Gyeonggi-do (KR); SAMSUNG ELECTRONICS CO., LTD., Suwon-si, Gyeonggi-do (KR)

(72) Inventors: Hyung-Sun Kim, Suwon-si (KR); Byung-Ku Kim, Suwon-si (KR); Young-Kwon Kim, Suwon-si (KR); Chang-Woo Kim, Suwon-si (KR); Joo-Hee Seo, Suwon-si (KR); Chang-Ju Shin, Suwon-si (KR); Seung-Jae Lee, Suwon-si (KR); Kyu Young Hwang, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 415 days.

(21) Appl. No.: 15/102,912

(22) PCT Filed: Jan. 8, 2015

(86) PCT No.: PCT/KR2015/000192
§ 371 (c)(1),
(2) Date: Jun. 9, 2016

(87) PCT Pub. No.: WO2015/108301
PCT Pub. Date: Jul. 23, 2015

(65) Prior Publication Data
US 2016/0308143 A1   Oct. 20, 2016

(30) Foreign Application Priority Data
Jan. 14, 2014 (KR) ........................ 10-2014-0004697

(51) Int. Cl.
*H01L 51/00* (2006.01)
*C07D 519/02* (2006.01)
(Continued)

(52) U.S. Cl.
CPC ........ *H01L 51/0071* (2013.01); *C07D 519/00* (2013.01); *C07D 519/02* (2013.01);
(Continued)

(58) Field of Classification Search
CPC .............. C07D 403/04; H01L 51/0072; H01L 51/0052
See application file for complete search history.

(56) References Cited

U.S. PATENT DOCUMENTS

2004/0043247 A1* 3/2004 Lee ....................... C07D 231/38
428/690
2008/0026135 A1 1/2008 Bentsen et al.
2013/0306955 A1* 11/2013 Mizutani ............. H01L 51/0072
257/40

FOREIGN PATENT DOCUMENTS

CN    1708485 A    12/2005
CN    103313979 A    9/2013
(Continued)

OTHER PUBLICATIONS

Kim, et al., "Synthesis and Hole-Transporting Properties of Phenyl-Carbazyl Derivatives." Mol. Cryst. Liq. Cryst. 2008, vol. 491, pp. 133-144.
(Continued)

*Primary Examiner* — Michael M Dollinger
(74) *Attorney, Agent, or Firm* — Lee & Morse, P.C.

(57) ABSTRACT

A novel condensed cyclic compound and an organic light emitting device including the same are disclosed.

12 Claims, 1 Drawing Sheet

(51) Int. Cl.
  *C07D 519/00* (2006.01)
  *C09K 11/02* (2006.01)
  *C09K 11/06* (2006.01)
  *H01L 51/50* (2006.01)

(52) U.S. Cl.
  CPC ............ *C09K 11/025* (2013.01); *C09K 11/06* (2013.01); *H01L 51/006* (2013.01); *H01L 51/0052* (2013.01); *H01L 51/0061* (2013.01); *H01L 51/0072* (2013.01); *H01L 51/0081* (2013.01); *C09K 2211/185* (2013.01); *H01L 51/0085* (2013.01); *H01L 51/5016* (2013.01); *H01L 51/5024* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(56) References Cited

FOREIGN PATENT DOCUMENTS

| | | |
|---|---|---|
| CN | 102056899 B | 11/2013 |
| JP | 2011-523943 A | 8/2011 |
| KR | 10-2006-0069089 A | 6/2006 |
| KR | 10-2011-0116177 A | 7/2010 |
| KR | 10-2010-0088604 A | 8/2010 |
| KR | 10-2010-0105099 | 9/2010 |
| KR | 10-2012-0009984 A | 2/2012 |
| KR | 10-2010-0122798 | 5/2012 |
| KR | 10-2012-0117693 A | 10/2012 |
| KR | 10-2013-0110051 A | 10/2013 |
| KR | 10-2013-0127563 | 11/2013 |
| KR | 10-2014-0000611 A | 1/2014 |
| KR | 10-2015-0061976 | 6/2015 |
| TW | 201343628 A | 11/2013 |
| WO | WO 2012/067425 A1 | 5/2012 |
| WO | WO 2013/012297 A1 | 1/2013 |
| WO | WO 2013/081416 A1 | 6/2013 |
| WO | WO 2013/180376 A1 | 12/2013 |

OTHER PUBLICATIONS

Search Report dated Mar. 28, 2017 of the corresponding Chinese Patent Application No. 201580003313.5.
Taiwanese Search Report dated Sep. 2, 2015.

* cited by examiner

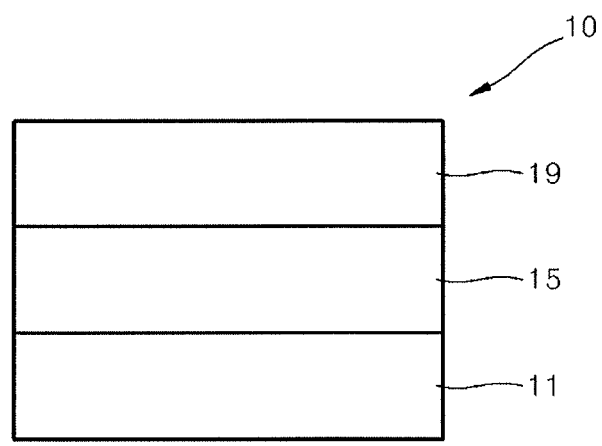

CONDENSED CYCLIC COMPOUND AND ORGANIC LIGHT EMITTING DEVICE INCLUDING THE SAME

CROSS REFERENCE TO RELATED APPLICATIONS

This is the U.S. national phase application based on PCT Application No. PCT/KR2015/000192, filed Jan. 8, 2015, which is based on Korean Patent Application No. 10-2014-0004697, filed Jan. 14, 2014, the entire contents of all of which are hereby incorporated by reference.

TECHNICAL FIELD

A condensed cyclic compound and an organic light emitting device including the same are disclosed.

BACKGROUND ART

Organic light emitting devices (OLEDs), which are self-emitting devices, have advantages such as wide viewing angles, excellent contrast, quick response, high brightness, excellent driving voltage characteristics, and may provide multicolored images. For example, an organic light emitting device may include an anode, a cathode and an emission layer interposed between the anode and the cathode. The organic light emitting device may include a hole transport region between the anode and the emission layer, and an electron transport region between the emission layer and the cathode. Holes injected from the anode move to the emission layer via the hole transport region, while electrons injected from the cathode move to the emission layer via the electron transport region. Carriers such as the holes and electrons recombine in the emission layer to generate excitons. When the excitons drop from an excited state to a ground state, light is emitted.

DISCLOSURE

Technical Problem

A novel condensed cyclic compound and an organic light emitting device including the same are provided.

Technical Solution

According to one aspect, a condensed cyclic compound represented by the following Formula 1 is provided:

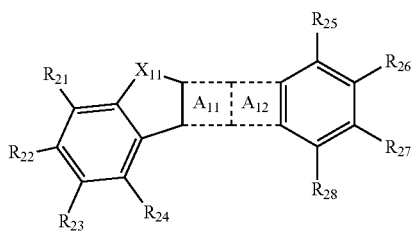

<Formula 1>

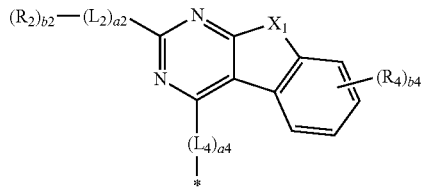

<Formula 2A>

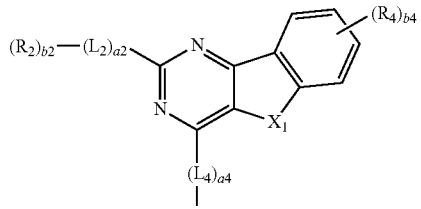

<Formula 2B>

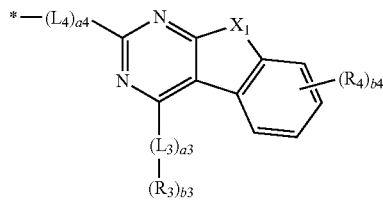

<Formula 2C>

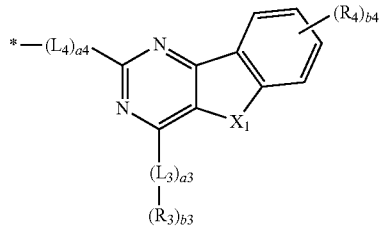

<Formula 2D>

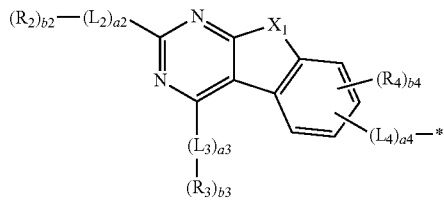

<Formula 2E>

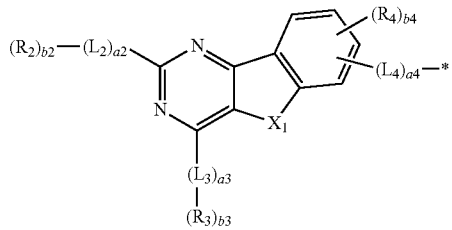

<Formula 2F>

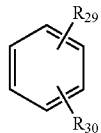

<Formula 1A>

-continued

<Formula 1B>

wherein, in the Formulae, in the Formula 1, the ring $A_{11}$ is represented by the Formula 1A;

in the Formula 1, the ring $A_{12}$ is represented by the Formula 1B;

$X_{11}$ is N-[$(L_{11})_{a11}$-$(R_{11})_{b11}$], S, O, S(=O), S(=O)$_2$, C(=O), C($R_{13}$)($R_{14}$), Si($R_{13}$)($R_{14}$), P($R_{13}$), P(=O)$R_{13}$ or C=N($R_{13}$);

$X_{12}$ is N-[$(L_{12})_{a12}$-$(R_{12})_{b12}$], S, O, S(=O), S(=O)$_2$, C(=O), C($R_{15}$)($R_{16}$), Si($R_{15}$)($R_{16}$), P($R_{15}$), P(=O)$R_{16}$ or C=N($R_{15}$);

$X_1$ is N-[$(L_1)_{a1}$-$(R_1)_{b1}$], S, O, S(=O), S(=O)$_2$, C(=O), Si($R_5$)($R_6$), P($R_5$), P(=O)$R_5$ or C=N($R_5$);

$L_1$ to $L_4$, $L_{11}$ and $L_{12}$ are independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic heterocondensed polycyclic group;

a1 to a4, a11 and a12 are independently selected from integers of 0 to 3;

$R_1$ to $R_6$, $R_{11}$ to $R_{16}$ and $R_{21}$ to $R_{30}$ are independently one of hydrogen, deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), —B($Q_6$)($Q_7$) or the group represented by the Formula 2A to the group represented by the Formula 2F, provided that the $R_1$ to $R_6$ are not the group represented by the Formula 2A to the group represented by the Formula 2F;

b1 to b4, b11 and b12 are independently selected from integers of 1 to 3;

i) in the Formula 1, when $X_{11}$ is N-[$(L_{11})_{a11}$-$(R_{11})_{b11}$] and $X_{12}$ is not N-[$(L_{12})_{a12}$-$(R_{12})_{b12}$], in the Formula 1, at least one of b11 $R_{11}$'s and $R_{21}$ to $R_{30}$ is selected from the group represented by the Formula 2A to the group represented by the Formula 2F;

ii) in the Formula 1, when $X_{11}$ is not N-[$(L_{11})_{a11}$-$(R_{11})_{b11}$] and $X_{12}$ is N-[$(L_{12})_{a12}$-$(R_{12})_{b12}$], in the Formula 1, at least one of b12 $R_{12}$'s and $R_{21}$ to $R_{30}$ is selected from the group represented by the Formula 2A to the group represented by the Formula 2F; and iii) in the Formula 1, when $X_{11}$ is N-[$(L_{11})_{a11}$-$(R_{11})_{b11}$] and $X_{12}$ is N-[$(L_{12})_{a12}$-$(R_{12})_{b12}$], in the Formula 1, at least one of b11 $R_{11}$'s, and b12 $R_{12}$'s and $R_{21}$ to $R_{30}$ is selected from the group represented by the Formula 2A to the group represented by the Formula 2F;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_6$ heteroaryl group, the substituted monovalent non-aromatic condensed polycyclic group and substituted monovalent non-aromatic hetero-condensed polycyclic group is, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{11}$)($Q_{12}$), —Si($Q_{13}$)($Q_{14}$)($Q_{15}$) and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —$N(Q_{21})(Q_{22})$, —$Si(Q_{23})(Q_{24})(Q_{25})$ and —$B(Q_{26})(Q_{27})$; or —$N(Q_{31})(Q_{32})$, —$Si(Q_{33})(Q_{34})(Q_{35})$ or —$B(Q_{36})(Q_{37})$;

wherein the $Q_1$ to $Q_7$, $Q_{11}$ to $Q_{17}$, $Q_{21}$, to $Q_{27}$ and $Q_{31}$ to $Q_{37}$ are independently hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group.

According to another aspect, an organic light emitting device includes a first electrode; a second electrode; and an organic layer including an emission layer interposed between the first electrode and the second electrode, and the organic layer includes at least one of the condensed cyclic compounds represented by the Formula 1.

The condensed cyclic compound may be included in the emission layer, the emission layer may further include a dopant, and the condensed cyclic compound in the emission layer may function as a host.

Advantageous Effects

The condensed cyclic compound has excellent electrical characteristics and thermal stability, and thus an organic light emitting device including the condensed cyclic compound may have a low driving voltage, high efficiency, high luminance and long life-span characteristics.

DESCRIPTION OF THE DRAWINGS

FIG. 1 is a schematic cross-sectional view showing an organic light emitting device according to one embodiment.

MODE FOR INVENTION

The condensed cyclic compound is represented by the following Formula 1:

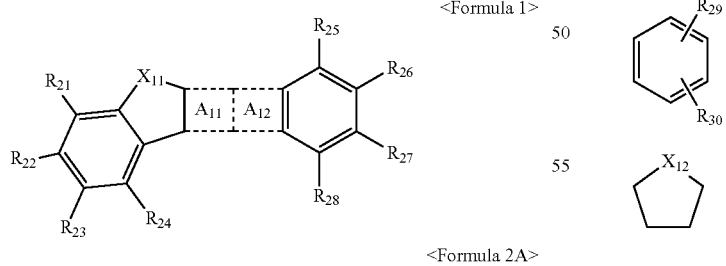

<Formula 1>

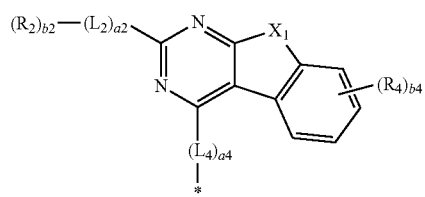

<Formula 2A>

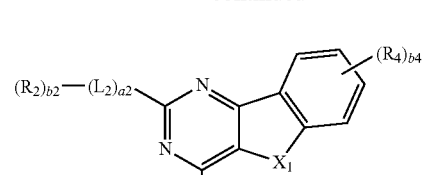

<Formula 2B>

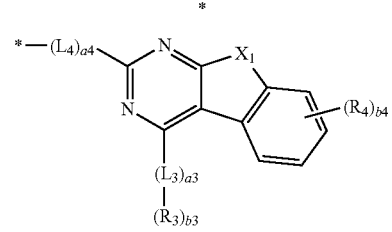

<Formula 2C>

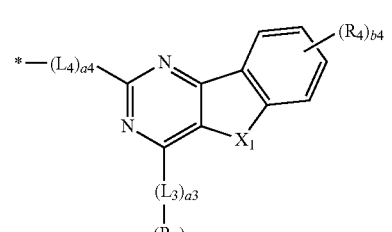

<Formula 2D>

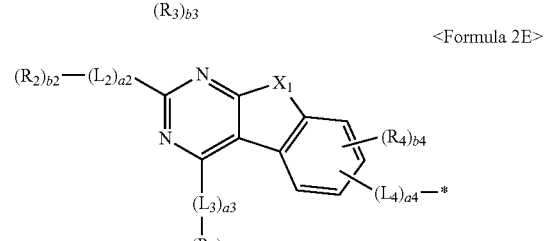

<Formula 2E>

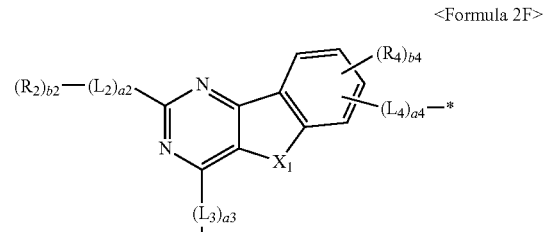

<Formula 2F>

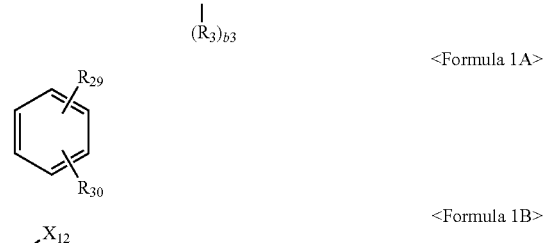

<Formula 1A>

<Formula 1B>

In the Formula 1, the ring $A_{11}$ is represented by the Formula 1A. In the Formula 1, the ring $A_{11}$ shares carbon atoms with adjacent 5-membered ring and the ring $A_{12}$, respectively and is fused therewith.

In the Formula 1, the ring $A_{12}$ is represented by the Formula 1B. In the Formula 1, the ring $A_{12}$ shares carbon atoms with adjacent 6-membered ring and the ring $A_{11}$, respectively and is fused therewith.

In the Formula 1, $X_{11}$ is $N-[(L_{11})_{a11}-(R_{11})_{b11}]$, S, O, S(=O), S(=O)$_2$, C(=O), C(R$_{13}$)(R$_{14}$), Si(R$_{13}$)(R$_{14}$), P(R$_{13}$), P(=O)R$_{13}$ or C=N(R$_{13}$), in the Formula 1B, $X_{12}$ is $N-[(L_{12})_{a12}-(R_{12})_{b12}]$, S, O, S(=O), S(=O)$_2$, C(=O), C(R$_{15}$)(R$_{16}$), Si(R$_{15}$)(R$_{16}$), P(R$_{15}$), P(=O)R$_{15}$ or C=N (R$_{15}$), and in the Formulae 2A to 2F, $X_1$ is $N-[(L_1)_{a1}-(R_1)_{b1}]$, S, O, S(=O), S(=O)$_2$, C(=O), Si(R$_5$)(R$_6$), P(R$_5$), P(=O) R$_5$ or C=N(R$_5$).

$L_1$ to $L_4$, $L_{11}$ and $L_{12}$ are independently a substituted or unsubstituted cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic heterocondensed polycyclic group;

a1 to a4, a11 and a12 are independently selected from integers of 0 to 3;

$R_1$ to $R_6$, $R_{11}$ to $R_{16}$ and $R_{21}$ to $R_{30}$ are independently one of hydrogen, deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N(Q$_1$)(Q$_2$), —Si(Q$_3$)(Q$_4$)(Q$_5$), —B(Q$_6$)(Q$_7$) or the group represented by the Formula 2A to the group represented by the Formula 2F, provided that the $R_1$ to $R_6$ are not the group represented by the Formula 2A to the group represented by the Formula 2F;

b1 to b4, b11 and b12 are independently selected from integers of 1 to 3; and the relationship between the Formula 1 and the Formulae 2A to 2F are as follows:

i) in the Formula 1, when $X_{11}$ is $N-[(L_{11})_{a11}-(R_{11})_{b11}]$ and $X_{12}$ is not $N-[(L_{12})_{a12}-(R_{12})_{b12}]$, in the Formula 1, at least one of b11 $R_{11}$'s and $R_{21}$ to $R_{30}$ is selected from the group represented by the Formula 2A to the group represented by the Formula 2F;

ii) in the Formula 1, when $X_{11}$ is not $N-[(L_{11})_{a11}-(R_{11})_{b11}]$ and $X_{12}$ is $N-[(L_{12})_{a12}-(R_{12})_{b12}]$, in the Formula 1, at least one of b12 $R_{12}$'s and $R_{21}$ to $R_{30}$ is selected from the group represented by the Formula 2A to the group represented by the Formula 2F; and iii) in the Formula 1, when $X_{11}$ is $N-[(L_{11})_{a11}-(R_{11})_{b11}]$ and $X_{12}$ is $N-[(L_{12})_{a12}-(R_{12})_{b12}]$, in the Formula 1, at least one of b11 $R_{11}$'s, and b12 $R_{12}$'s and $R_{21}$ to $R_{30}$ is selected from the group represented by the Formula 2A to the group represented by the Formula 2F.

At least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_6$ heteroaryl group, the substituted monovalent non-aromatic condensed polycyclic group and substituted monovalent non-aromatic heterocondensed polycyclic group is, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N(Q$_{11}$)(Q$_{12}$), —Si(Q$_{13}$)(Q$_{14}$)(Q$_{15}$) and —B(Q$_{16}$)(Q$_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one selected from deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N(Q$_{21}$)(Q$_{22}$), —Si(Q$_{23}$)(Q$_{24}$)(Q$_{25}$) and —B(Q$_{26}$)(Q$_{27}$); or —N(Q$_{31}$)(Q$_{32}$), —Si(Q$_{33}$)(Q$_{34}$)(Q$_{35}$) or —B(Q$_{36}$)(Q$_{37}$);

wherein the $Q_1$ to $Q_7$, $Q_{11}$ to $Q_{17}$, $Q_{21}$ to $Q_{27}$ and $Q_{31}$ to $Q_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group.

According to one embodiment, $X_{11}$ in the Formula 1 may be N-$[(L_{11})_{a11}$-$(R_{11})_{b11}]$, S, or O.

According to another embodiment, $X_{12}$ in the Formula 1B may be N-$[(L_{12})_{a12}$-$(R_{12})_{b12}]$, S, or O.

According to another embodiment, $X_1$ in the Formulae 2A to 2F may be N-$[(L_1)_{a1}$-$(R_1)_{b1}]$, S, or O.

The $X_{11}$ and $X_{12}$ may be the same or different from each other.

In the Formulae, $L_1$ to $L_4$, $L_{11}$ and $L_{12}$ may be independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic heterocondensed polycyclic group.

For example, in the Formulae, $L_1$ to $L_4$, $L_{11}$ and $L_{12}$ may be independently, a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, s thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, or an imidazopyridinylene group; or a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group or an imidazopyridinylene group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, a $C_2$-$C_{60}$ heteroaryl group, a monovalent non-aromatic condensed polycyclic group, a monovalent non-aromatic heterocondensed ring group, and —Si($Q_{33}$)($Q_{34}$)($Q_{35}$); and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group or a quinazolinyl group.

According to one embodiment, in the Formulae, $L_1$ to $L_4$, $L_{11}$ and $L_{12}$ may be independently represented by one of Formulae 2-1 to 2-13, but is not limited thereto:

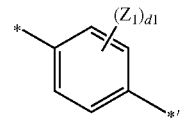

Formula 2-1

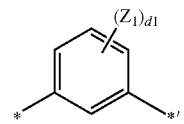

Formula 2-2

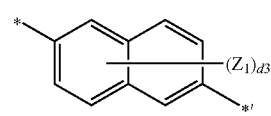

Formula 2-3

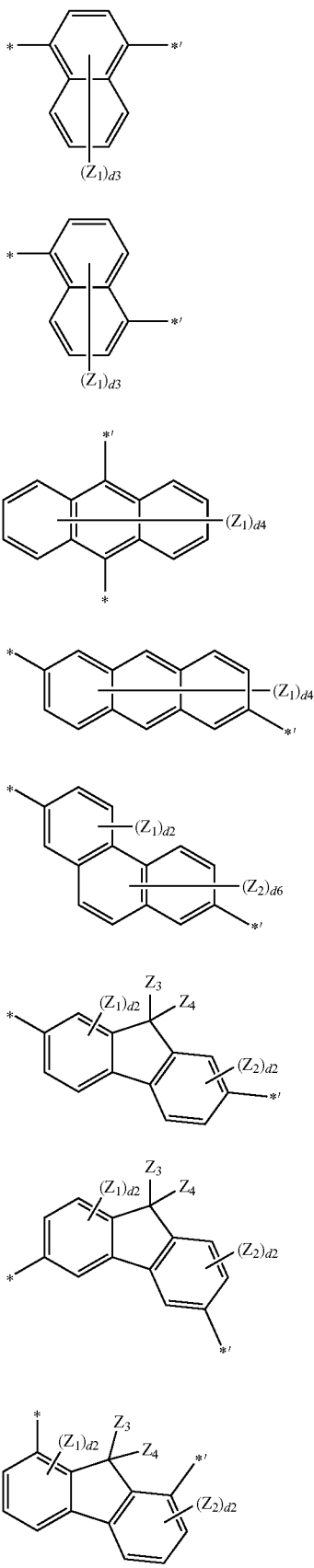

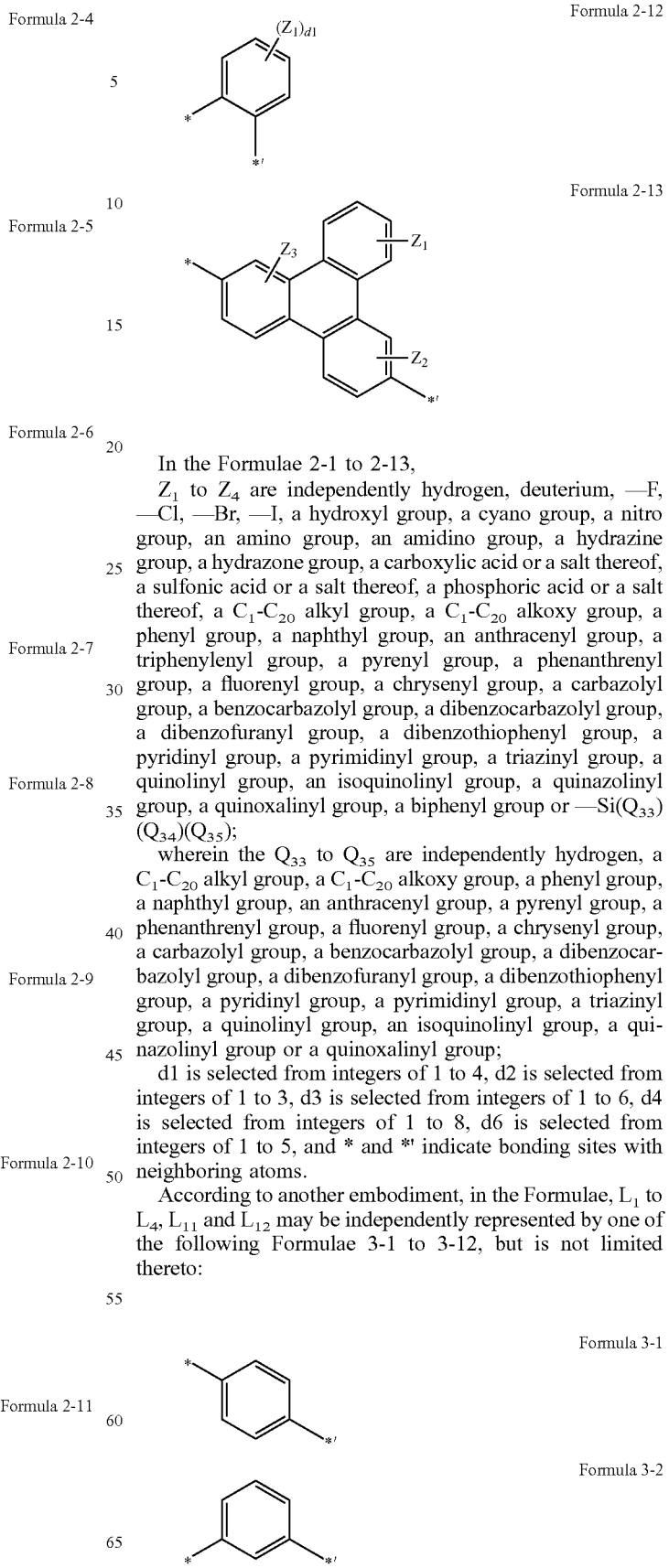

In the Formulae 2-1 to 2-13, $Z_1$ to $Z_4$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group or —Si($Q_{33}$)($Q_{34}$)($Q_{35}$);

wherein the $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group;

d1 is selected from integers of 1 to 4, d2 is selected from integers of 1 to 3, d3 is selected from integers of 1 to 6, d4 is selected from integers of 1 to 8, d6 is selected from integers of 1 to 5, and * and *' indicate bonding sites with neighboring atoms.

According to another embodiment, in the Formulae, $L_1$ to $L_4$, $L_{11}$ and $L_{12}$ may be independently represented by one of the following Formulae 3-1 to 3-12, but is not limited thereto:

-continued

Formula 3-3

Formula 3-4

Formula 3-5

Formula 3-6

Formula 3-7

Formula 3-8

Formula 3-9

Formula 3-10

Formula 3-11

Formula 3-12

In the Formulae 2A to 2F, a1 indicates the number of $L_1$, and selected from integers of 0 to 3. For example, a1 may be 0 or 1. When a1 is 0, $R_1$ is directly linked to N. When a1 is greater than or equal to 2, two or more $L_1$ may be the same or different from each other. The descriptions of a2 to a4, a11 and a12 refer to the descriptions of the a1 and Formula 1 and Formulae 2A to 2F.

According to one embodiment, a1 to a4, a11 and a12 may be independently 0 or 1.

Herein, in the Formulae, $R_1$ to $R_6$, $R_{11}$ to $R_{16}$ and $R_{21}$ to $R_{30}$ are independently one of hydrogen, deuterium, —F (a fluoro group), —Cl (a chloro group), —Br (a bromo group), —I (an iodo group), a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), —B($Q_6$)($Q_7$) or the group represented by the Formula 2A to the group represented by the Formula 2F, provided that the $R_1$ to $R_6$ are not the group represented by the Formula 2A to the group represented by the Formula 2F.

According to one embodiment, the $R_1$ to $R_6$, $R_{11}$ to $R_{16}$ and $R_{21}$ to $R_{30}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group;

—Si($Q_3$)($Q_4$)($Q_5$) (provided that the $R_{13}$ to $R_{16}$ and $R_5$ and $R_6$ are not —Si($Q_3$)($Q_4$)($Q_5$)), or one of the group represented by the Formula 2A to the group represented by the Formula 2F (provided that the $R_1$ to $R_6$ are not the group represented by the Formula 2A to the group represented by the Formula 2F);

wherein the $Q_1$ to $Q_7$ and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group, but are not limited thereto.

According to another embodiment, in the Formulae, $R_1$ to $R_6$, $R_{11}$ to $R_{16}$ and $R_{21}$ to $R_{30}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

one of the following Formulae 4-1 to 4-31;

—Si($Q_3$)($Q_4$)($Q_5$) (provided that the $R_{13}$ to $R_{16}$ and $R_5$ to $R_6$ are not —Si($Q_3$)($Q_4$)($Q_5$)); or one of the group represented by the Formula 2A to the group represented by the Formula 2F (provided that $R_1$ to $R_6$ are not the group represented by the Formula 2A to the group represented by the Formula 2F), but are not limited thereto:

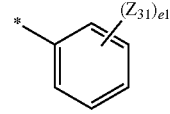

Formula 4-1

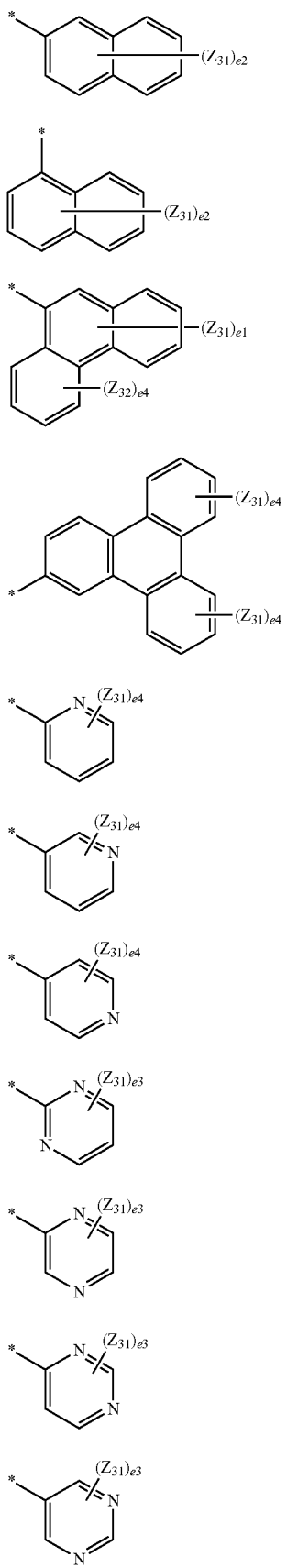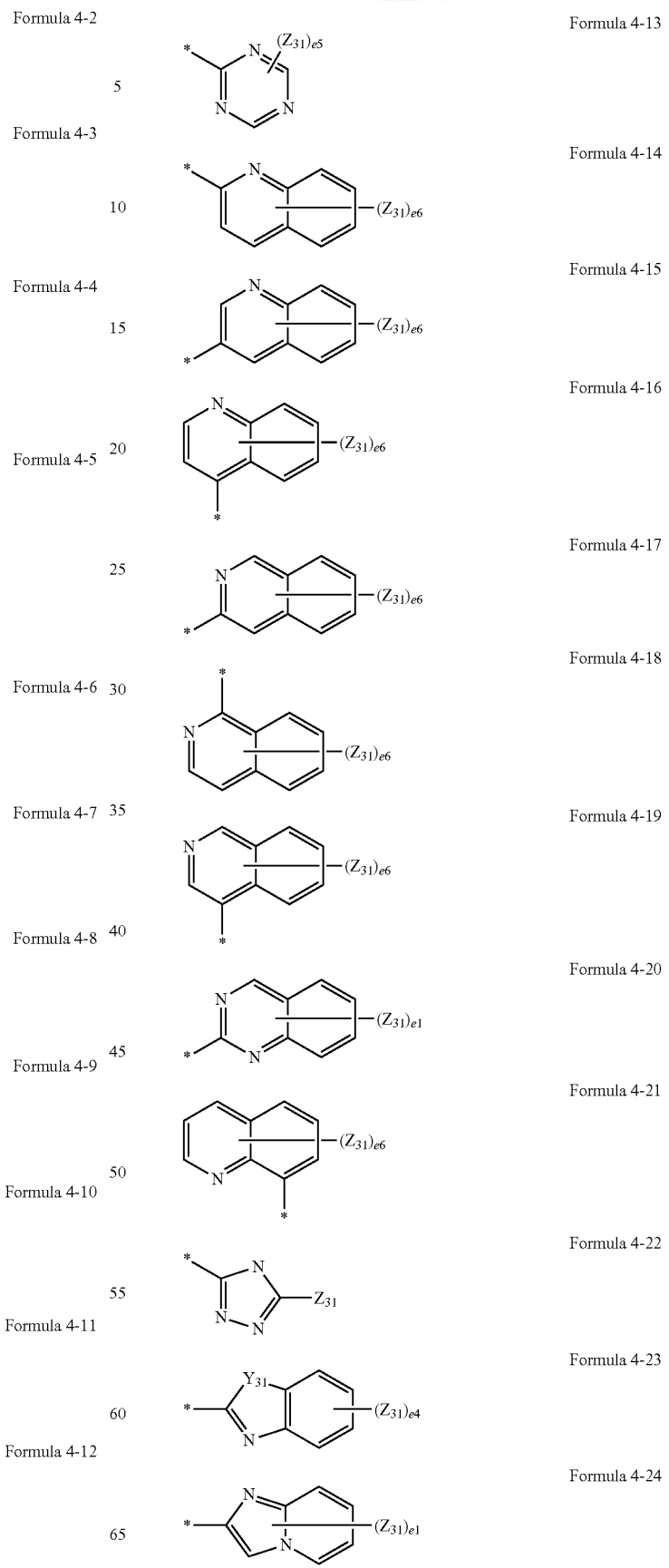

-continued

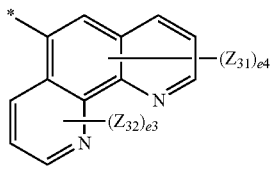
Formula 4-25

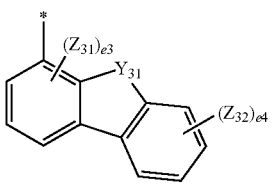
Formula 4-26

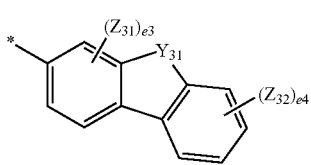
Formula 4-27

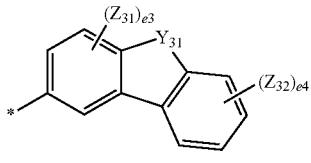
Formula 4-28

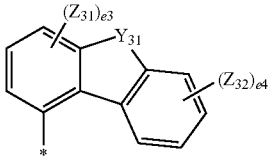
Formula 4-29

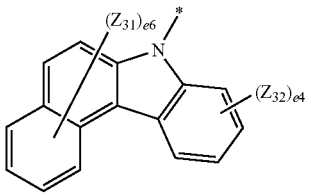
Formula 4-30

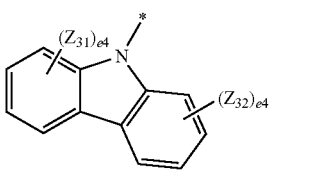
Formula 4-31

In the Formulae 4-1 to 4-31, $Y_{31}$ is O, S, $C(Z_{33})(Z_{34})$, $N(Z_{35})$ or $Si(Z_{36})(Z_{37})$ (provided that in the Formula 4-23, $Y_{31}$ is not NH);

$Z_{31}$ to $Z_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group or —$Si(Q_{33})(Q_{34})(Q_{35})$;

the $Q_3$ to $Q_5$ and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group;

e1 is selected from integers of 1 to 5, e2 is selected from integers of 1 to 7, e3 is selected from integers of 1 to 3, e4 is selected from integers of 1 to 4, e5 is 1 or 2, e6 is selected from integers of 1 to 6, and * indicates a bonding site with a neighboring atom.

According to another embodiment, in the Formulae, $R_1$ to $R_6$, $R_{11}$ to $R_{16}$ and $R_{21}$ to $R_{30}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

one of the following Formulae 5-1 to 5-63;

—$Si(Q_3)(Q_4)(Q_5)$ (provided that the $R_{13}$ to $R_{16}$, $R_5$ and $R_6$ are not —$Si(Q_3)(Q_4)(Q_5)$), or the group represented by the Formula 2A to the group represented by the Formula 2F (provided that the $R_1$ to $R_6$ are not the group represented by the Formula 2A to the group represented by the Formula 2F); but are not limited thereto:

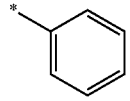
Formula 5-1

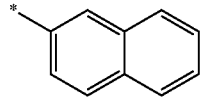
Formula 5-2

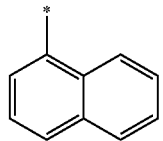
Formula 5-3

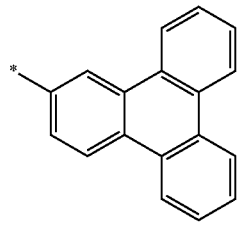
Formula 5-4

-continued
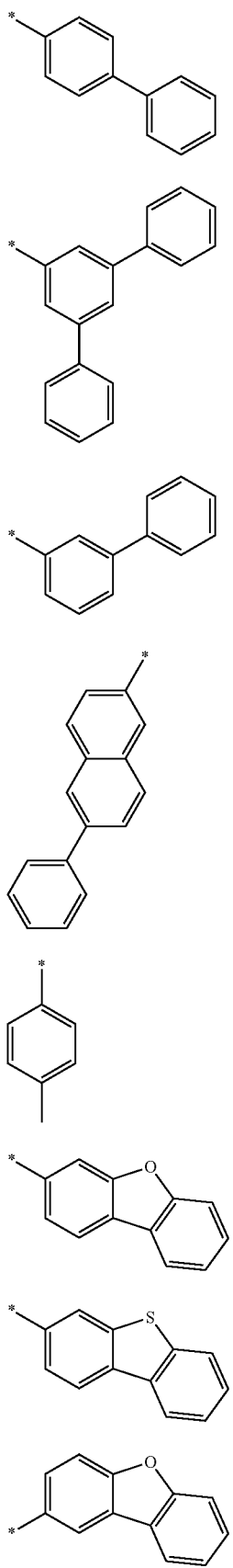
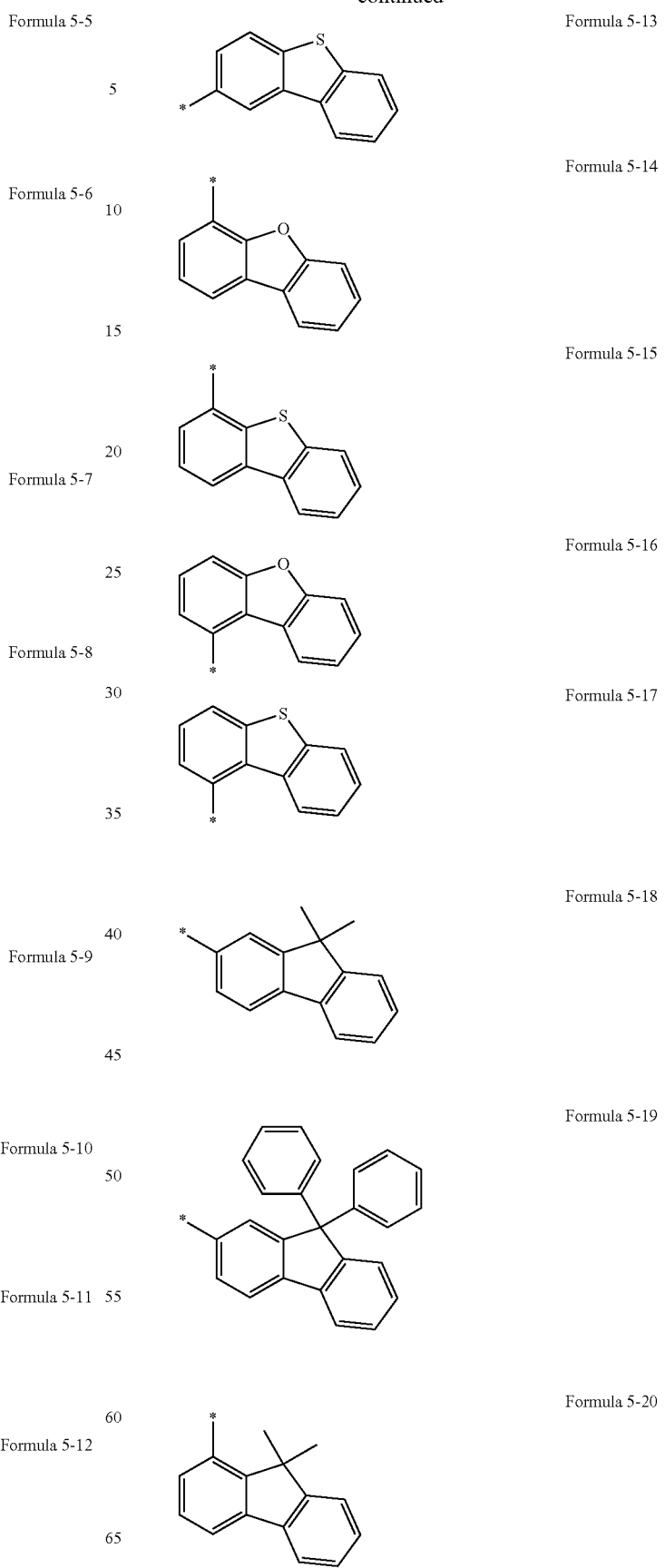

Formula 5-21
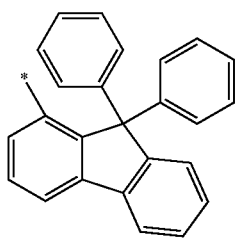
Formula 5-22
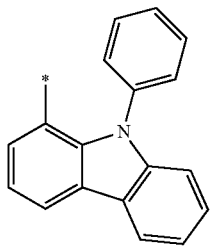
Formula 5-23
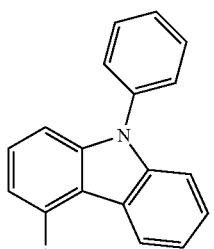
Formula 5-24
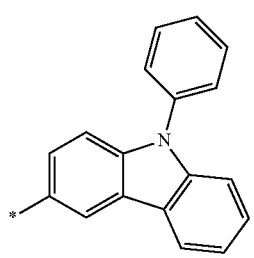
Formula 5-25
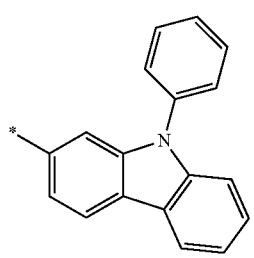
Formula 5-26
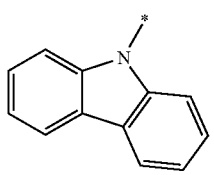
Formula 5-27
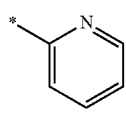
Formula 5-28
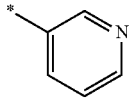
Formula 5-29
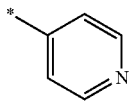
Formula 5-30
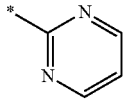
Formula 5-31
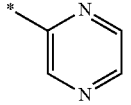
Formula 5-32
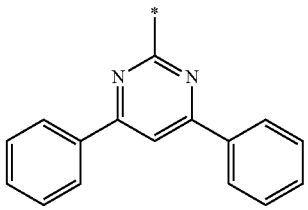
Formula 5-33
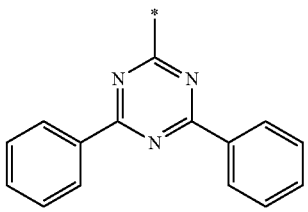
Formula 5-34
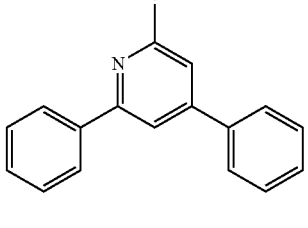
Formula 5-35
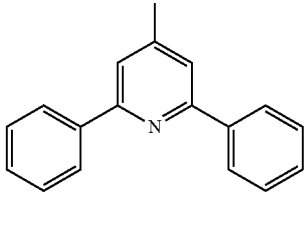
Formula 5-36
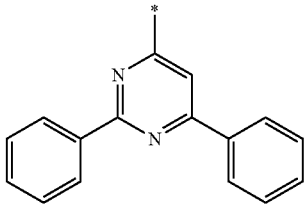

Formula 5-37
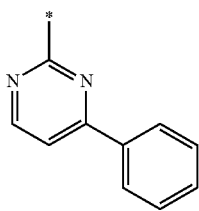
Formula 5-38
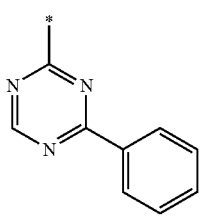
Formula 5-39
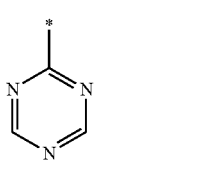
Formula 5-40
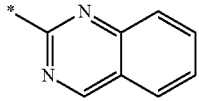
Formula 5-41
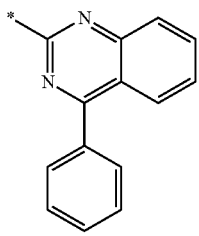
Formula 5-42
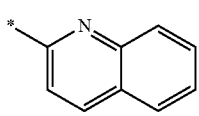
Formula 5-43
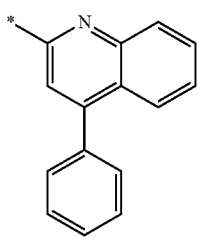
Formula 5-44
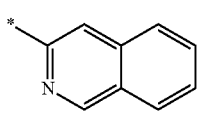
Formula 5-45
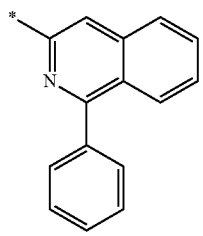
Formula 5-46
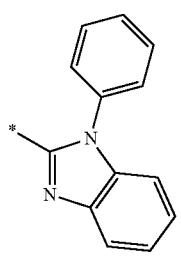
Formula 5-47
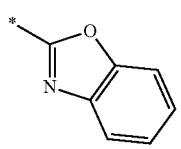
Formula 5-48
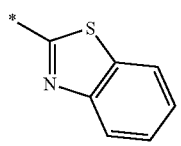
Formula 5-49
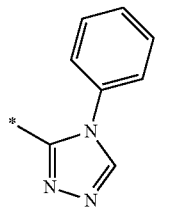
Formula 5-50
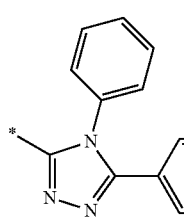
Formula 5-51
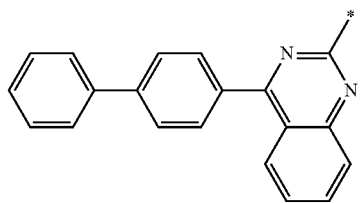
Formula 5-52
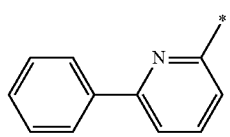

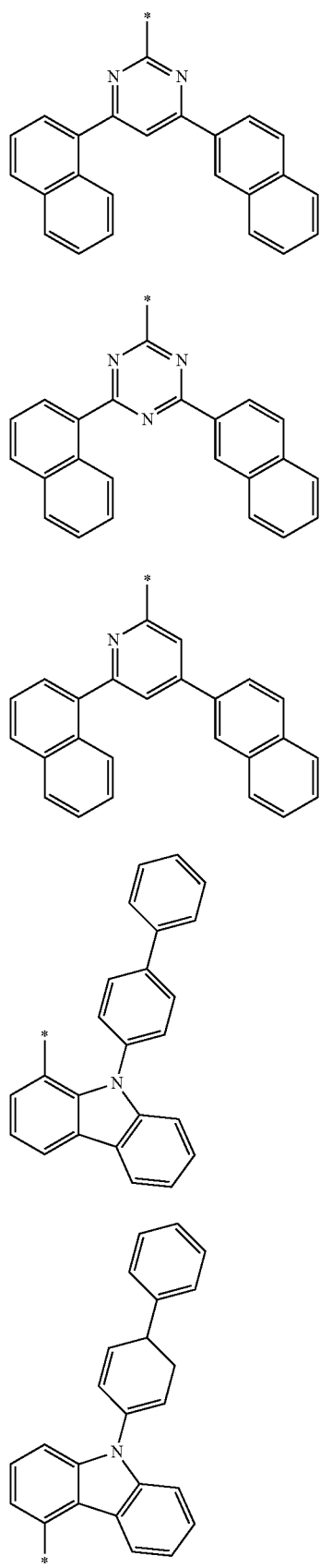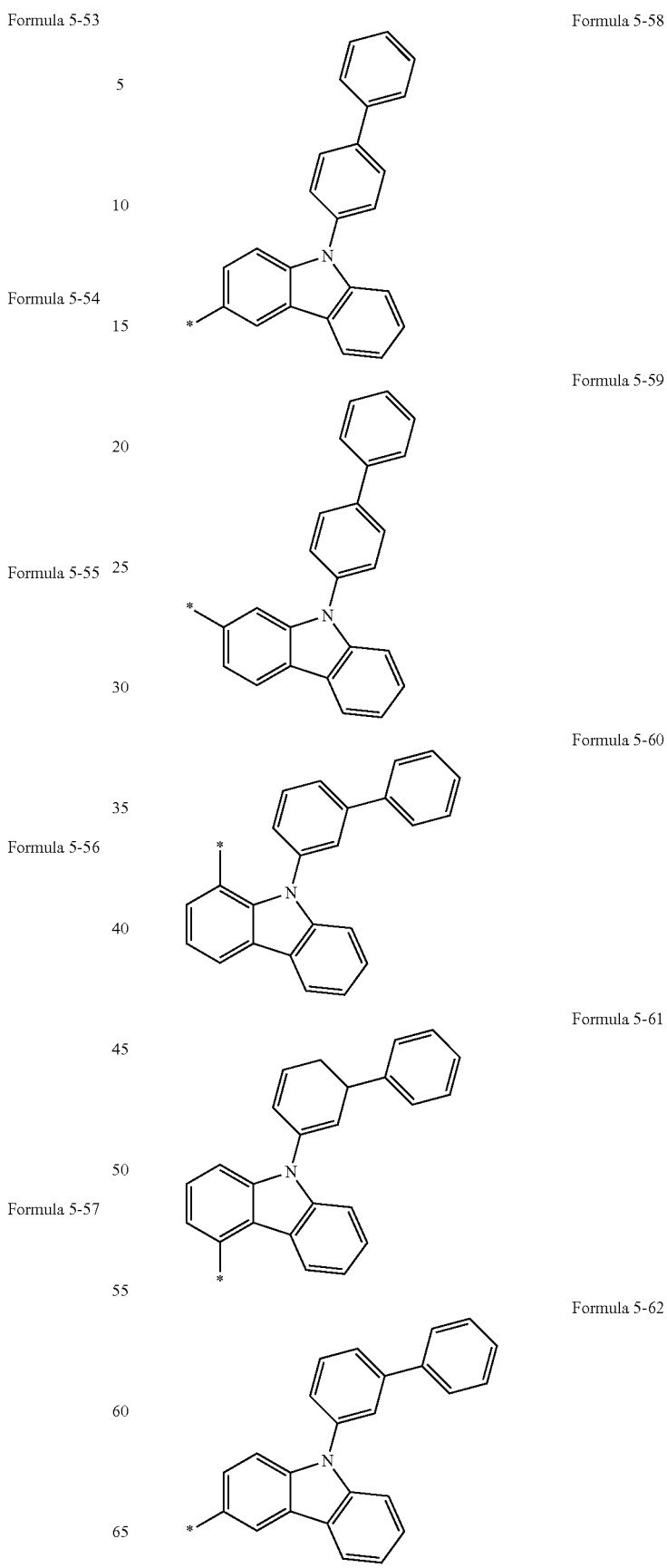
Formula 5-53
Formula 5-54
Formula 5-55
Formula 5-56
Formula 5-57
Formula 5-58
Formula 5-59
Formula 5-60
Formula 5-61
Formula 5-62

Formula 5-63

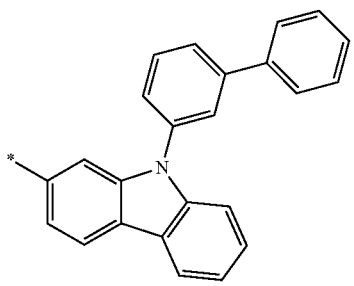

On the other hand, $R_2$ in the Formulae 2A and 2B, $R_3$ in the Formulae 2C and 2D and at least one of $R_2$ and $R_3$ in the Formulae 2E and 2F is, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si$(Q_{33})(Q_{34})(Q_{35})$, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group and a biphenyl group;

wherein the $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group.

For example, $R_2$ in the Formula 2A and 2B, $R_3$ in the Formulae 2C and 2D, and at least one of $R_2$ and $R_3$ in the Formulae 2E and 2F is, a phenyl group, a naphthyl group, a triphenylenyl group, a phenanthrenyl group, a pyridinyl group, a pyrimidinyl group, a pyrazinyl group, a pyridazinyl group or a triazinyl group; or a phenyl group, a naphthyl group, a triphenylenyl group, a phenanthrenyl group, a pyridinyl group, a pyrimidinyl group, a pyrazinyl group, a pyridazinyl group or a triazinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si$(Q_{33})(Q_{34})(Q_{35})$, a phenyl group, a naphthyl group, a triphenylenyl group, a phenanthrenyl group, a pyridinyl group, a pyrimidinyl group, pyrazinyl group, a pyridazinyl group and a triazinyl group;

wherein the $Q_{33}$ to $Q_{35}$ are independently hydrogen, a $C_1$-$C_{20}$ alkyl group, a $C_1$-$C_{20}$ alkoxy group, a phenyl group or a naphthyl group.

According to another embodiment, $R_2$ in the Formulae 2A and 2B, $R_3$ in the Formulae 2C and 2D and at least one of $R_2$ and $R_3$ in the Formulae 2E and 2F may be selected from the Formulae 5-1 to 5-63, but are not limited thereto.

According to another embodiment, $R_1$ of $X_1$ in the Formulae 2A to 2F, $R_{11}$ of $X_{11}$ in the Formula 1, and $R_{12}$ of $X_{12}$ in the Formula 1B are independently one of a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_2$-$C_{20}$ heteroaryl group, a substituted or unsubstituted monovalent non-aromatic condensed polycyclic group, a substituted or unsubstituted monovalent non-aromatic heterocondensed polycyclic group, or the group represented by the Formula 2A to the group represented by the Formula 2F, provided that the $R_1$ is not the group represented by the Formula 2A to the group represented by the Formula 2F.

For example, $R_1$ of $X_1$ in the Formulae 2A to 2F, $R_{11}$ of $X_{11}$ in the Formula 1, and $R_{12}$ of $X_{12}$ in the Formula 1B are independently a phenyl group, a naphthyl group, a triphenylenyl group, a phenanthrenyl group, a pyridinyl group, a pyrimidinyl group, a pyrazinyl group, a pyridazinyl group or a triazinyl group;

a phenyl group, a naphthyl group, a triphenylenyl group, a phenanthrenyl group, a pyridinyl group, a pyrimidinyl group, a pyrazinyl group, a pyridazinyl group or a triazinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, a triphenylenyl group, a phenanthrenyl group, a pyridinyl group, a pyrimidinyl group, a pyrazinyl group, a pyridazinyl group and a triazinyl group; or one of the groups represented by the Formula 2A to the group represented by the Formula 2F; but is not limited thereto. Herein, the $R_1$ is not the group represented by the Formula 2A to the group represented by the Formula 2F.

According to another embodiment, $R_4$ in the Formulae 2A to 2F may be independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or $C_1$-$C_{20}$ alkoxy group, but is not limited thereto.

In the Formulae, b1 indicates the number of $R_1$, and may be selected from integers of 1 to 3. When b1 is greater than or equal to 2, two or more $R_1$'s may be the same or different from each other. Descriptions for b2 to b4, b11 and b12 refer to description for b1 and structures of Formula 1 and Formulae 2A to 2F.

According to another embodiment, the condensed cyclic compound represented by the Formula 1 may be represented by one of the following Formulae 1-1 to 1-6:

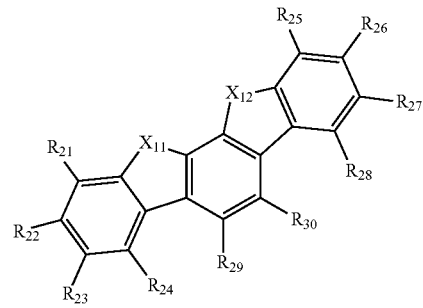

Formula 1-1

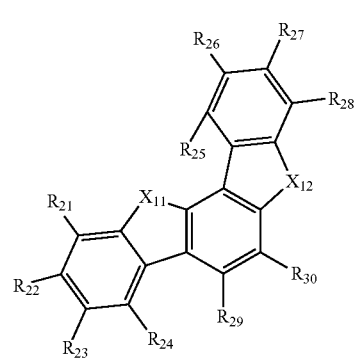

Formula 1-2

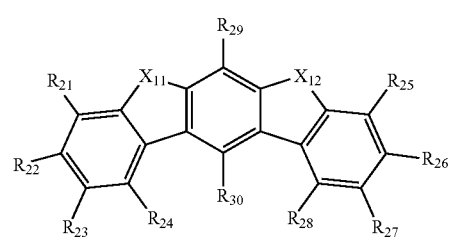

Formula 1-3

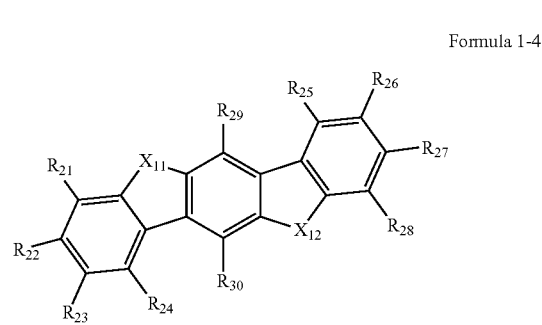

Formula 1-4

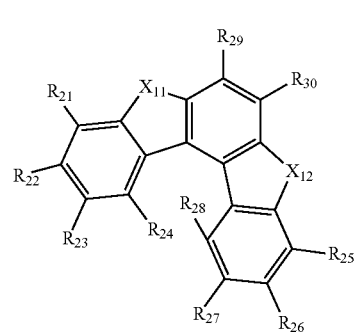

Formula 1-5

Formula 1-6

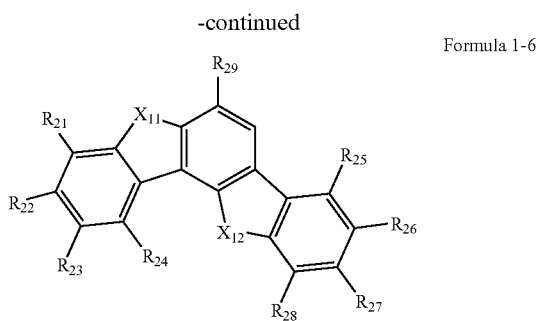

In the Formulae 1-1 to 1-6, descriptions for $X_{11}$, $X_{12}$ and $R_{21}$ to $R_{30}$ are the same as described in the present specification.

For example, in the Formula 1-1 to 1-6, $X_{11}$ is N-[$(L_{11})_{a11}$-$(R_{11})_{b11}$], S or O;

$X_{12}$ is N-[$(L_{12})_{a12}$-$(R_{12})_{b12}$], S or O;

$X_1$ is N-[$(L_1)_{a1}$-$(R_1)_{b1}$], S or O;

i) in the Formulae 1-1 to 1-6, when $X_{11}$ is N-[$(L_{11})_{a11}$-$(R_{11})_{b11}$], $X_{12}$ is not N-[$(L_{12})_{a12}$-$(R_{12})_{b12}$], in the Formula 1, at least one of b11 $R_{11}$'s and $R_{21}$ to $R_{30}$ is selected from the group represented by the Formula 2A to the group represented by the Formula 2F;

ii) in the Formulae 1-1 to 1-6, when $X_{11}$ is not N-[$(L_{11})_{a11}$-$(R_{11})_{b11}$], and $X_{12}$ is N-[$(L_{12})_{a12}$-$(R_{12})_{b12}$], in the Formula 1, at least one of b12 $R_{12}$'s and $R_{21}$ to $R_{30}$ is selected from the group represented by the Formula 2A to the group represented by the Formula 2F; and iii) in the Formulae 1-1 to 1-6, when $X_{11}$ is N-[$(L_{11})_{a11}$-$(R_{11})_{b11}$], and $X_{12}$ is N-[$(L_{12})_{a12}$-$(R_{12})_{b12}$], in the Formula 1, at least one of b11 $R_{11}$'s, and b12 $R_{12}$'s and $R_{21}$ to $R_{30}$ is selected from the group represented by the Formula 2A to the group represented by the Formula 2F;

the $L_1$ to $L_4$, $L_{11}$ and $L_{12}$ are independently selected from the Formulae 2-1 to 2-13 (for example, the Formulae 3-1 to 3-12);

the a1 to a4, a11 and a12 are independently 0 or 1;

the $R_1$, $R_{11}$ and $R_{12}$ are independently a phenyl group, a naphthyl group, a triphenylenyl group, a phenanthrenyl group, a pyridinyl group, a pyrimidinyl group, a pyrazinyl group, a pyridazinyl group or a triazinyl group;

a phenyl group, a naphthyl group, a triphenylenyl group, a phenanthrenyl group, a pyridinyl group, a pyrimidinyl group, a pyrazinyl group, a pyridazinyl group or a triazinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, a triphenylenyl group, a phenanthrenyl group, a pyridinyl group, a pyrimidinyl group, a pyrazinyl group, a pyridazinyl group and a triazinyl group; or the group represented by the Formula 2A to the group represented by the Formula 2F (provided that $R_1$ is not the group represented by the Formula 2A to the group represented by the Formula 2F);

at least one of the $R_2$ and $R_3$ is a phenyl group, a naphthyl group, a triphenylenyl group, a phenanthrenyl group, a pyridinyl group, a pyrimidinyl group, a pyrazinyl group, a pyridazinyl group or a triazinyl group; or a phenyl group, a naphthyl group, a triphenylenyl group, a phenanthrenyl group, a pyridinyl group, a pyrimidinyl group, a pyrazinyl group, a pyridazinyl group or a triazinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a naphthyl group, a triphenylenyl group, a phenanthrenyl group, a pyridinyl group, a pyrimidinyl group, a pyrazinyl group, a pyridazinyl group and a triazinyl group;

the $R_4$ is hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

$R_{21}$ to $R_{30}$ are independently one of hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof; and the Formulae 4-1 to 4-31 (for example, one of the Formulae 5-1 to 5-63);

—Si($Q_3$)($Q_4$)($Q_5$), or the group represented by the Formula 2A to the group represented by the Formula 2F (provided that the $R_1$ to $R_6$ are not the group represented by the Formula 2A to the group represented by the Formula 2F), but are not limited thereto.

According to one embodiment, the condensed cyclic compound represented by the Formula 1 may be, i) represented by the Formula 1-1 or 1-2, wherein in the Formulae 1-1 and 1-2, $R_{21}$ may be selected from the groups represented by the Formula 2A to Formula 2F, or ii) represented by the Formula 1-1 or 1-6, wherein in the Formulae 1-1 and 1-6, $X_{11}$ may be N-[$(L_{11})_{a11}$-$(R_{11})_{b11}$], and $R_{11}$ may be selected from the groups represented by the Formulae 2A to Formula 2F.

According to another embodiment, in the condensed cyclic compound, i) in the Formula 1, when $X_{11}$ is N-[$(L_{11})_{a11}$-$(R_{11})_{b11}$], and $X_{12}$ is not N-[$(L_{12})_{a12}$-$(R_{12})_{b12}$], in the Formula 1, at least one of b11 $R_{11}$'s and $R_{21}$ to $R_{30}$ is selected from the group represented by the Formula 2A, the group represented by the Formula 2B, the group represented by the Formula 2D, and the group represented by the following Formula 2F-1;

ii) in the Formula 1, when $X_{11}$ is not N-[$(L_{11})_{a11}$-$(R_{11})_{b11}$], and $X_{12}$ is N-[$(L_{12})_{a12}$-$(R_{12})_{b12}$], in the Formula 1, at least one of b12 $R_{12}$'s and $R_{21}$ to $R_{30}$ is selected from the group represented by the Formula 2A, the group represented by the Formula 2B, the group represented by the Formula 2D, and the group represented by the following Formula 2F-1; and iii) in the Formula 1, when $X_{11}$ is N-[$(L_{11})_{a11}$-$(R_{11})_{b11}$] and $X_{12}$ is N-[$(L_{12})_{a12}$-$(R_{12})_{b12}$], in the Formula 1, at least one of b11 and b12 $R_{12}$'s and $R_{21}$ to $R_{30}$ is selected from the group represented by the Formula 2A, the group represented by the Formula 2B, the group represented by the Formula 2D, and the group represented by the following Formula 2F-1:

<Formula 2F-1>

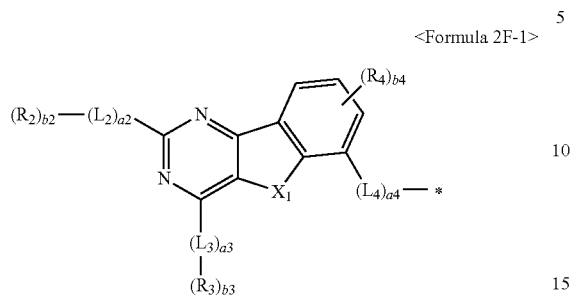

The descriptions for the Formula 2F-1 refer to the descriptions for the Formula 2F.

The condensed cyclic compound represented by the Formula 1 may be one of the following compounds 1 to 40, but is not limited thereto.

1

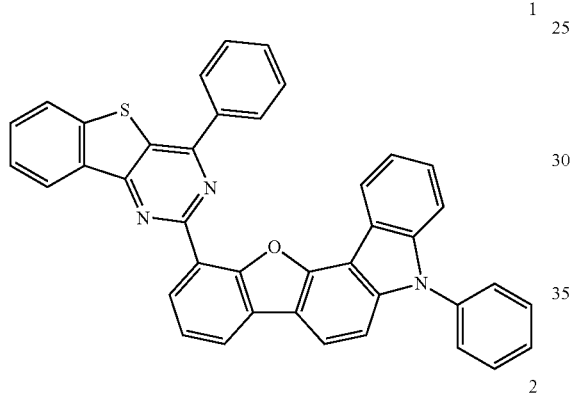

2

3

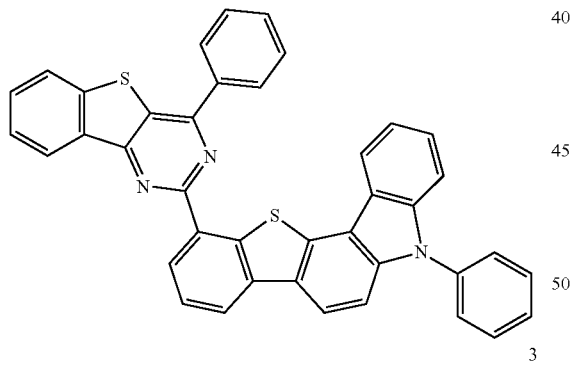

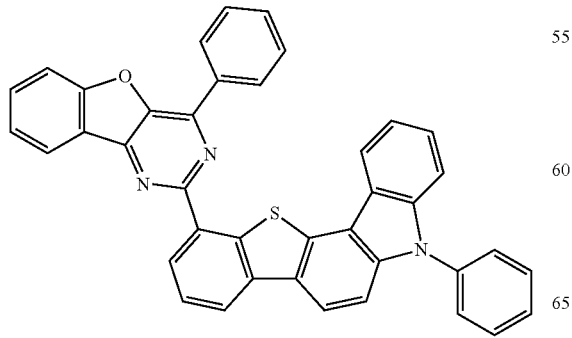

4

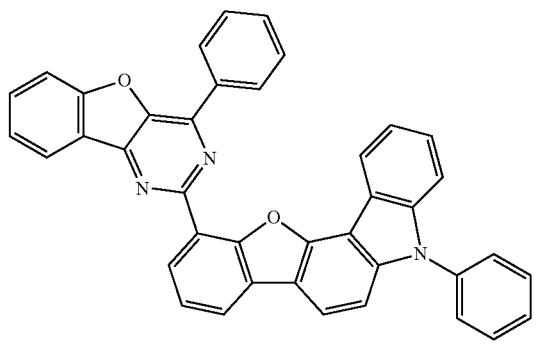

5

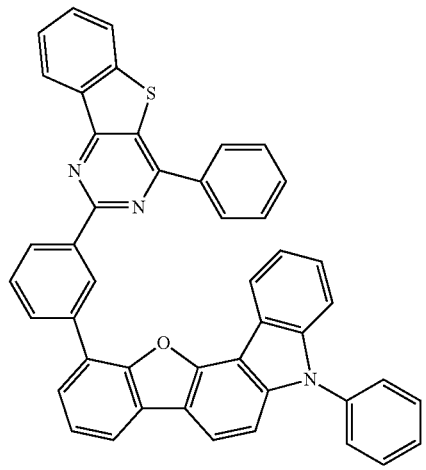

6

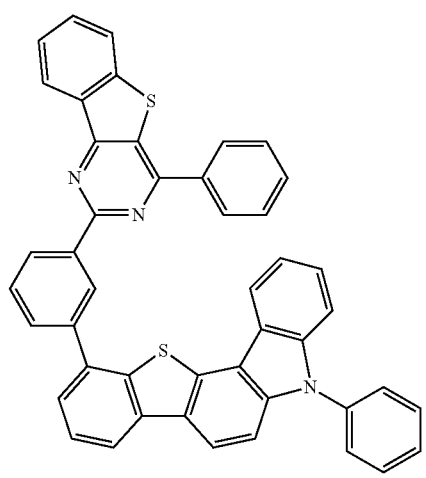

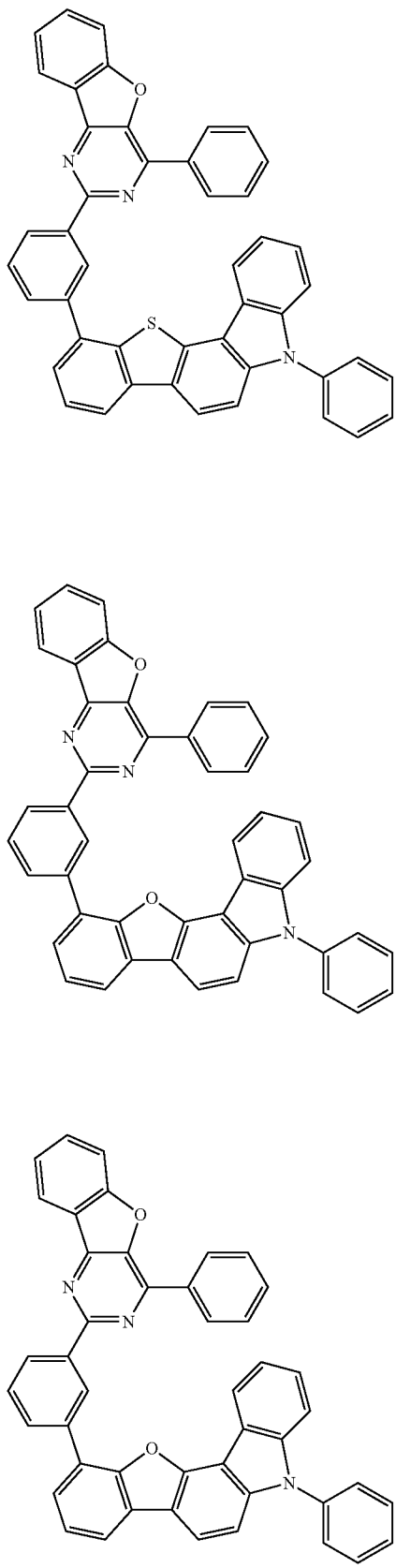
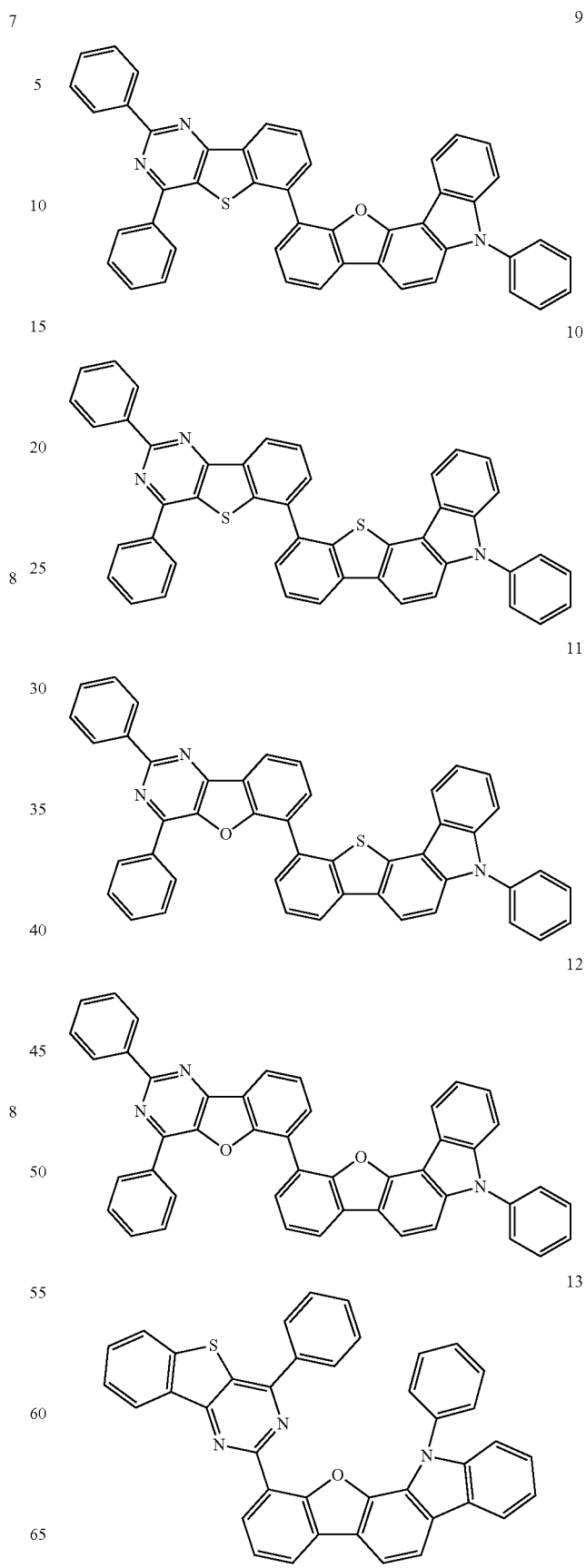

14
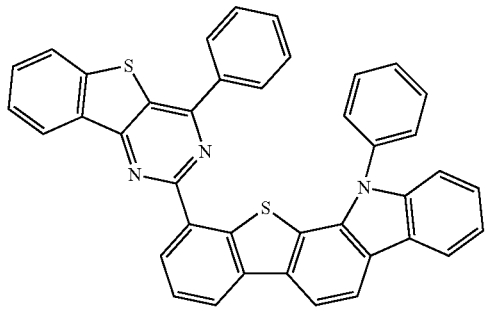
15
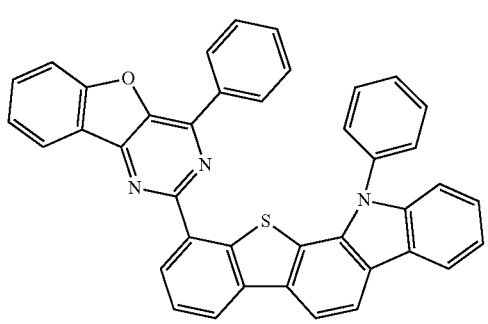
16
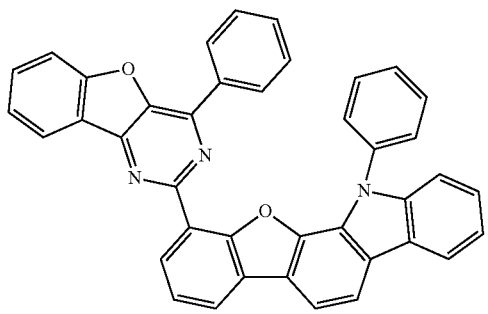
17
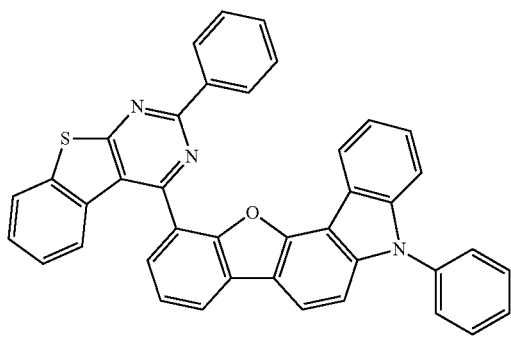
18
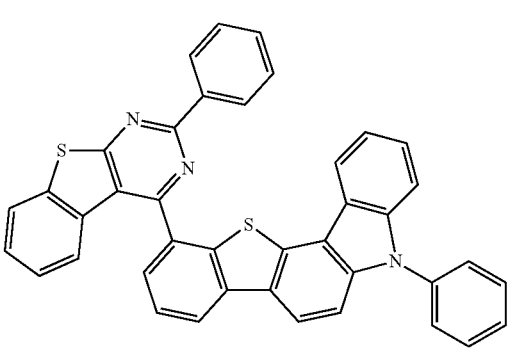
19
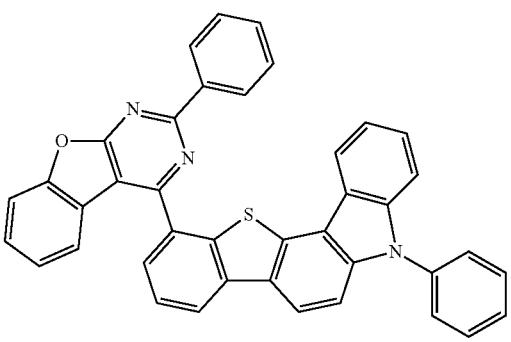
20
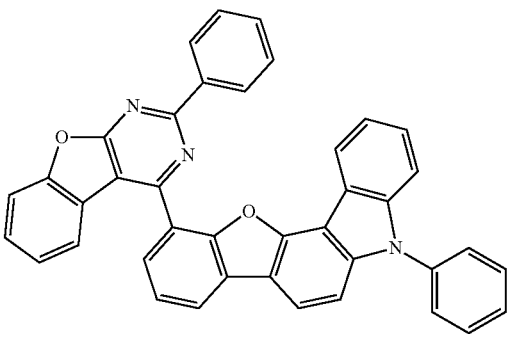
21
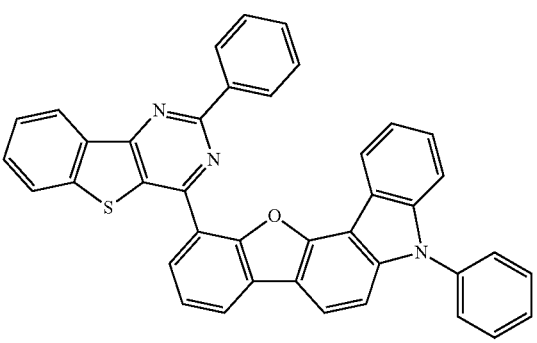

22
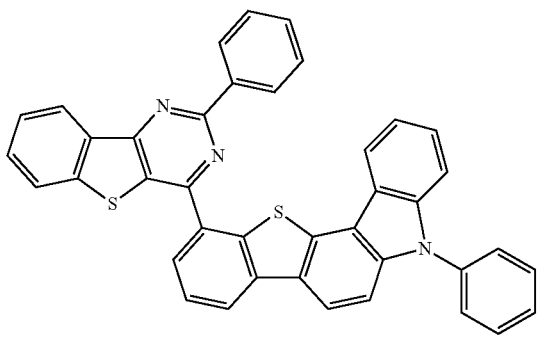
23
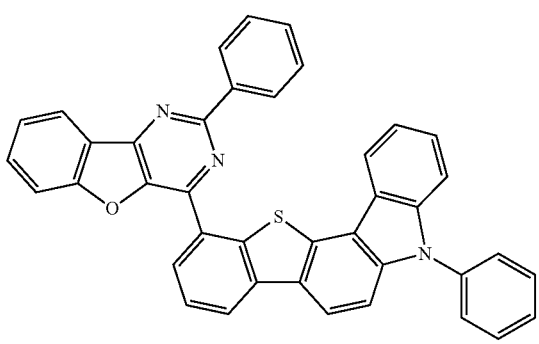
24
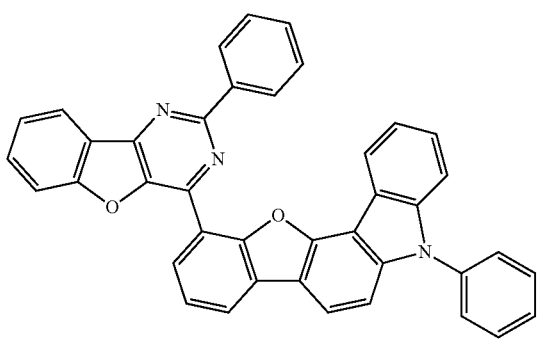
25
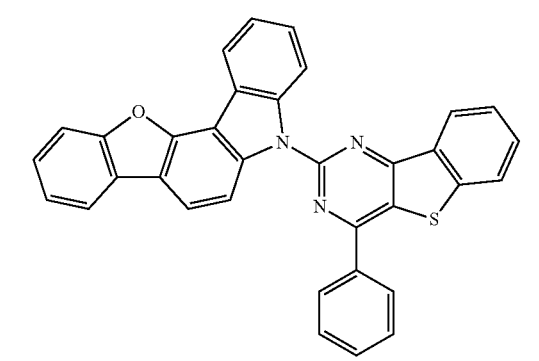
26
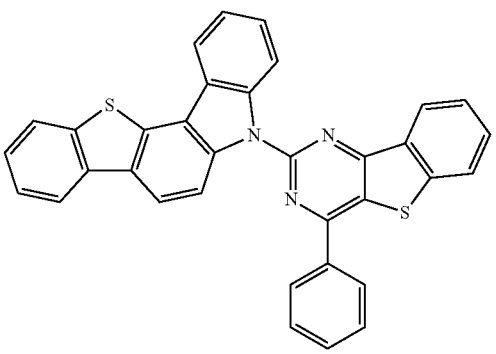
27
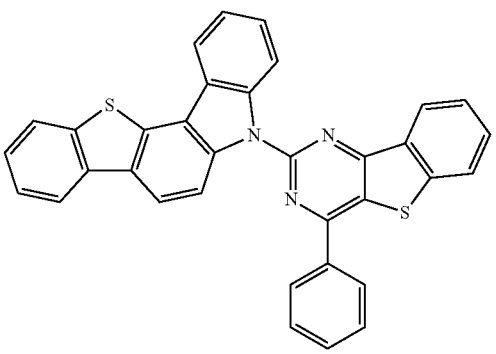
28
29
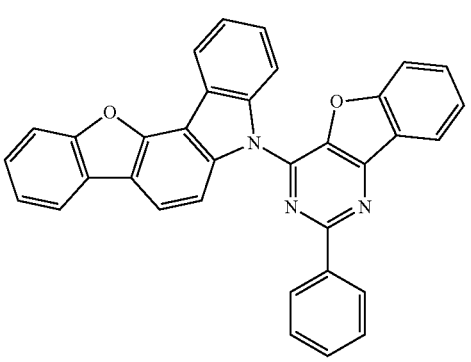

30
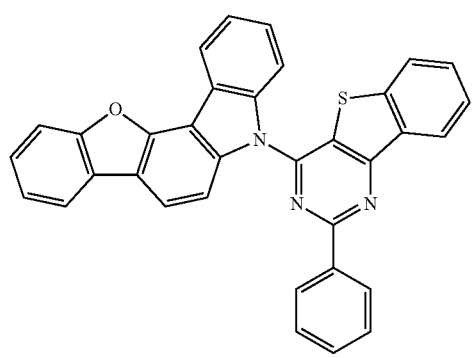
31
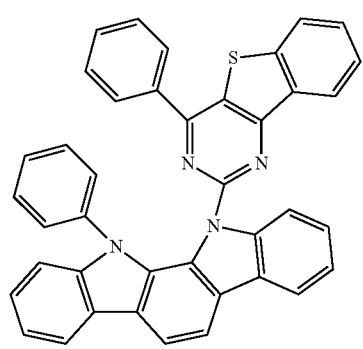
32
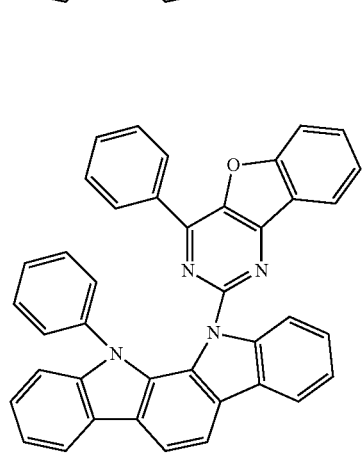
33
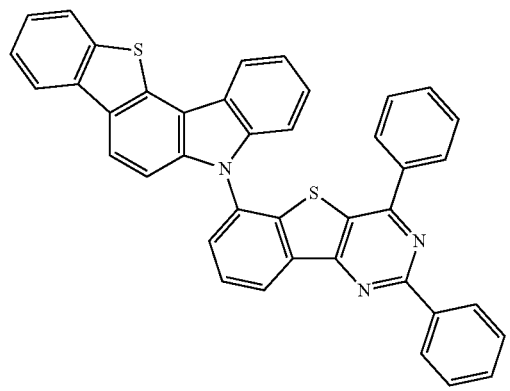
34
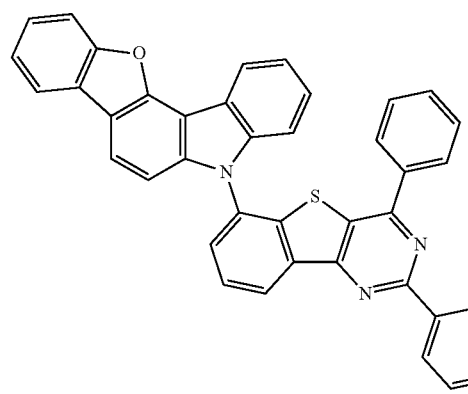
35
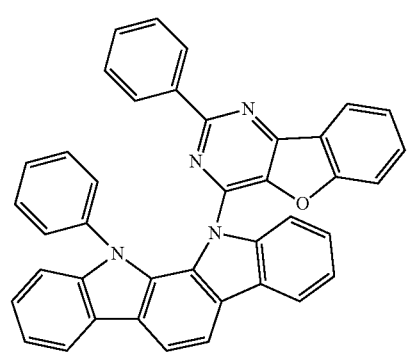
36
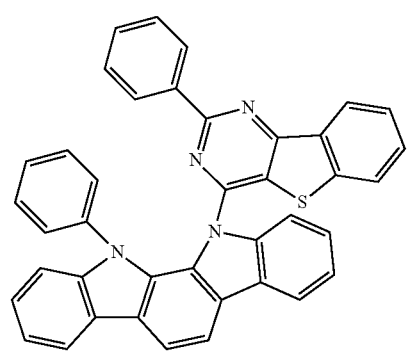
37
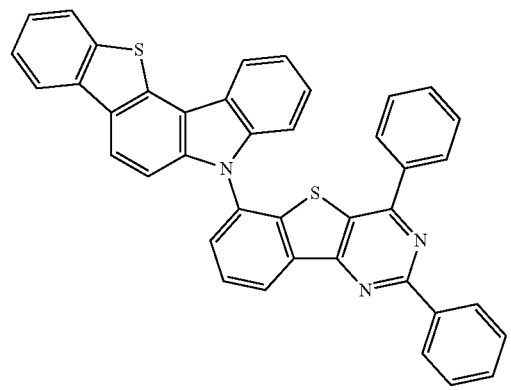

38

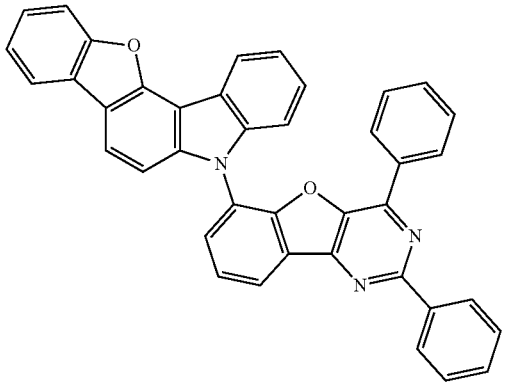

39

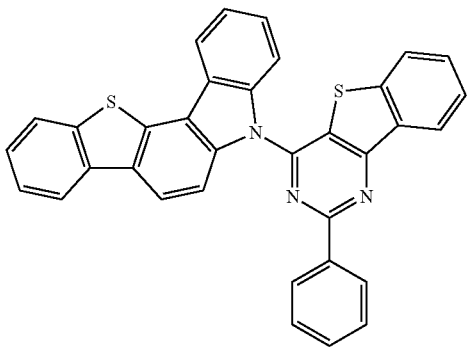

40

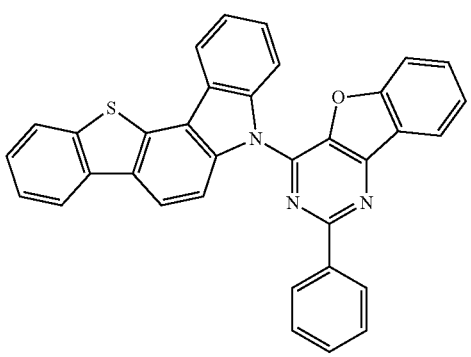

The condensed cyclic compound represented by the Formula 1 necessarily includes at least one of the groups represented by the Formulae 2A to 2F. The groups represented by the Formulas 2A to 2F has a core that "pyrimidine" is fused at one side of a 5-membered ring, and the "pyrimidine" as an electron withdrawing group may improve electron injection and transport characteristics of the condensed cyclic compound represented by the Formula 1.

The following Table 1 shows the HOMO energy level, LUMO energy level and T1 energy level data of the compounds 1, 2, 21, 22, 25, 4, 3, 24, 23, 27, 28 and 35 and the following compound A evaluated by using Gaussian. The following compound A has a group in which "pyridine" is fused at one side of a thiophene ring.

TABLE 1

| Compound No. | HOMO (eV) (calculation value) | LUMO (eV) (calculation value) | T1 energy level (eV) (calculation value) |
|---|---|---|---|
| Compound 1 | −5.157 | −1.756 | 2.713 |
| Compound 2 | −5.163 | −1.814 | 2.651 |
| Compound 21 | −5.319 | −1.693 | 2.796 |
| Compound 22 | −5.288 | −1.816 | 2.670 |
| Compound 25 | −5.297 | −1.996 | 2.541 |
| Compound 4 | −5.160 | −1.826 | 2.744 |
| Compound 3 | −5.165 | −1.906 | 2.723 |
| Compound 24 | −5.317 | −1.769 | 2.740 |
| Compound 23 | −5.256 | −1.881 | 2.586 |
| Compound 27 | −5.235 | −1.889 | 2.796 |
| Compound 28 | −5.253 | −1.977 | 2.719 |
| Compound 35 | −5.219 | −1.711 | 2.781 |
| Compound A | −5.047 | −1.640 | 2.733 |

<Compound A>

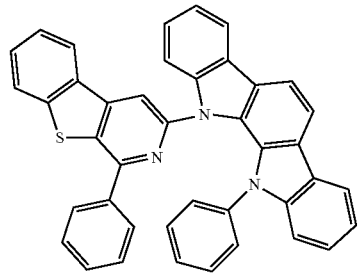 [SMILES: c1ccc(-c2nc(-n3c4ccccc4c4ccc5c6ccccc6n(-c6ccccc6)c5c43)cc3c2sc2ccccc23)cc1]

Referring to the Table 1, the compound A has a higher LUMO level than the compounds 1, 2, 21, 22, 25, 4, 3, 24, 23, 27, 28 and 35 (i.e., the compound A has a smaller LUMO level absolute value than the compounds 1, 2, 21, 22, 25, 4, 3, 24, 23, 27, 28 and 35), and thus, a condensed cyclic compound represented by the Formula 1 such as the compounds 1, 2, 21, 22, 25, 4, 3, 24, 23, 27, 28 and 35 turns out to have excellent electron transport characteristics compared with the compound A.

Accordingly, when the condensed cyclic compound represented by the Formula 1 is used as an organic layer material for an organic light emitting device, for example, an emission layer material for an organic light emitting device (for example, a host in the emission layer for an organic light emitting device), an organic light emitting device may have improved luminous efficiency due to an effective charge transport balance.

A method of synthesizing the condensed cyclic compound represented by the Formula 1 may be easily understood by a person of an ordinary skill in the art with a reference to the post-described Synthesis Examples.

Accordingly, the condensed cyclic compound represented by the Formula 1 may be appropriately applied to an organic layer for an organic light emitting device, for example, a host in an emission layer as the organic layer, and another embodiment of the present invention provides an organic light emitting device including a first electrode; a second electrode; and the organic layer interposed between the first electrode and the second electrode, including an emission layer, and including at least one condensed cyclic compound represented by the Formula 1.

The organic light emitting device includes the organic layer including the condensed cyclic compound represented by the Formula 1 and thus, may have a low driving voltage, high efficiency, high luminance and a long life-span.

The condensed cyclic compound represented by the Formula 1 may be used between a pair of electrodes of an organic light emitting device. For example, the condensed cyclic compound may be included in a hole transport region (for example, at least one of a hole injection layer (HIL), a hole transport layer (HTL) and an electron blocking layer) between the emission layer and the first electrode and in an electron transport region (for example, at least one of a hole blocking layer, an electron transport layer (ETL) and an electron injection layer (EIL)) between the emission layer and the second electrode. For example, the condensed cyclic compound represented by the Formula 1 may be included in the emission layer. Herein, the emission layer may further include a dopant, and the condensed cyclic compound included in the emission layer may play a role of a host. The emission layer may be a blue emission layer emitting blue light or a green emission layer emitting green light, and the dopant may be a phosphorescent dopant.

In the present specification, "(an organic layer) includes at least one condensed cyclic compound" may be understood as "(the organic layer) may include one kind of condensed cyclic compound belonging to the Formula 1 or more than two condensed cyclic compounds belonging to the Formula 1."

For example, the organic layer may include only the compound 1 as the condensed cyclic compound. Herein, the compound 1 may be present in the emission layer of an organic light emitting device. In addition, the organic layer may include the compounds 1 and 2 as the condensed cyclic compound. Herein, the compounds 1 and 2 may be present in the same layer (for example, the compounds 1 and 2 may be present in the emission layer) or in different layers.

The first electrode is an anode of a hole injection electrode, while the second electrode is a cathode of an electron injection electrode, or the first electrode is a cathode of an electron injection electrode, while the second electrode is a cathode of a hole injection electrode.

For example, the first electrode is an anode, the second electrode is a cathode, and the organic layer may include i) a hole transport region interposed between the first electrode and the emission layer and including at least one of a hole injection layer (HIL), a hole transport layer (HTL) and electron blocking layer; and ii) an electron transport region interposed between the emission layer and the second electrode and including at least one of a hole blocking layer, an electron transport layer (ETL) and an electron injection layer (EIL).

In the present specification, the "organic layer" is a term indicating a single layer and/or a plurality of layers interposed between first and second electrodes in an organic light emitting device. The "organic layer" may include an organic metal complex including a metal and the like as well as an organic compound.

FIG. 1 is a schematic cross-sectional view of an organic light emitting device 10 according to one embodiment of the present invention. Hereinafter, referring to FIG. 1, a structure and a manufacturing method an organic light emitting device according to one embodiment of the present invention are described as follows. An organic light emitting device 10 has a structure where a first electrode 11, an organic layer 15 and a second electrode 19 are sequentially stacked.

A substrate may be additionally disposed beneath the first electrode 11 or on the second electrode 19. The substrate may be any substrate used in an organic light emitting device and for example, include a glass substrate or a transparent plastic substrate having excellent mechanical strength, thermal stability, transparency, surface flatness, easy handling and waterproof.

The first electrode 11 may be fabricated by depositing, for example, a material for the first electrode on the substrate in a deposition method, a sputtering method or the like. The first electrode 11 may be an anode. The material for the first electrode may be selected from the materials having a high work function to facilitate a hole injection. The first electrode 11 may be a reflective electrode, a transflective electrode or a transmissive electrode. The material for the first electrode may be indium tin oxide (ITO), indiumzinc oxide (IZO), tin oxide ($SnO_2$), zinc oxide (ZnO) and the like. In addition, a metal such as magnesium (Mg), aluminum (Al), aluminum-lithium (Al—Li), calcium (Ca), magnesium-indium (Mg—In), magnesium-silver (Mg—Ag) and the like may be used.

The first electrode 11 may have a monolayer structure or a multi-layer structure including more than two layers.

On the first electrode 11, an organic layer 15 is disposed.

The organic layer 15 may include a hole transport region; an emission layer; and an electron transport region.

The hole transport region may be disposed between the first electrode 11 and the emission layer.

The hole transport region may include at least one of a hole injection layer (HIL), a hole transport layer (HTL), an electron blocking layer and a buffer layer.

The hole transport region includes only the hole injection layer (HIL) or the hole transport layer (HTL). Or, the hole transport region may have a structure of hole injection layer (HIL)/hole transport layer (HTL) or hole injection layer (HIL)/hole transport layer (HTL)/electron blocking layer sequentially stacked from the first electrode 11.

When the hole transport region includes the hole injection layer (HIL), the hole injection layer (HIL) may be formed on the first electrode 11 in a vacuum deposition method, a spin coating method, a cast method, a LB method and the like.

When the vacuum deposition method is used to form the hole injection layer (HIL), the deposition may be performed under various conditions depending on a compound as a material for the hole injection layer (HIL), its structure and thermal characteristics and the like of the hole injection layer (HIL) but, for example, at a temperature of about 100 to about 500° C., a vacuum degree of about $10^{-8}$ to about $10^{-3}$ torr, at a deposit speed of about 0.01 to about 100 Å/sec but is not limited thereto.

The spin coating method of forming the hole injection layer (HIL) may be performed under various conditions depending on a compound as a material for the hole injection layer (HIL), its structure and thermal characteristics and the like of the hole injection layer (HIL) but, for example, at a coating speed of about 2000 rpm to about 5000 rpm and a heat treatment temperature of about 80° C. to 200° C. for removing a solvent after the coating, but is not limited thereto.

The hole transport layer (HTL) and the electron blocking layer are formed referring to the conditions for forming the hole injection layer (HIL).

The hole transport region may include, for example, at least one of m-MTDATA, TDATA, 2-TNATA, NPB, β-NPB, TPD, Spiro-TPD, Spiro-NPB, α-NPB, TAPC, HMTPD, TCTA (4,4',4"-tris(N-carbazolyl)triphenylamine), Pani/DBSA (polyaniline/dodecylbenzenesulfonic acid), PEDOT/PSS (poly (3,4-ethylenedioxythiophene)/poly(4-styrenesulfonate)), Pani/CSA (polyaniline/camphor sulfonic acid), PANI/PSS (polyaniline/poly (4-styrenesulfonate)), a compound represented by the following Formula 201 and a compound represented by the following Formula 202:

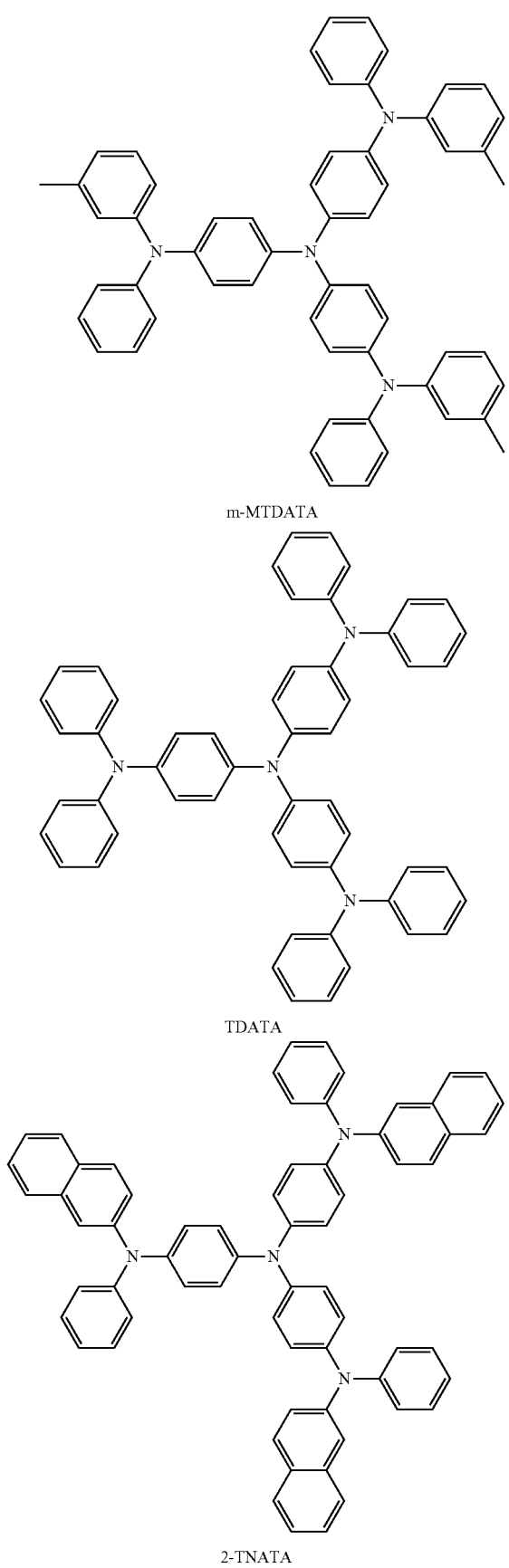
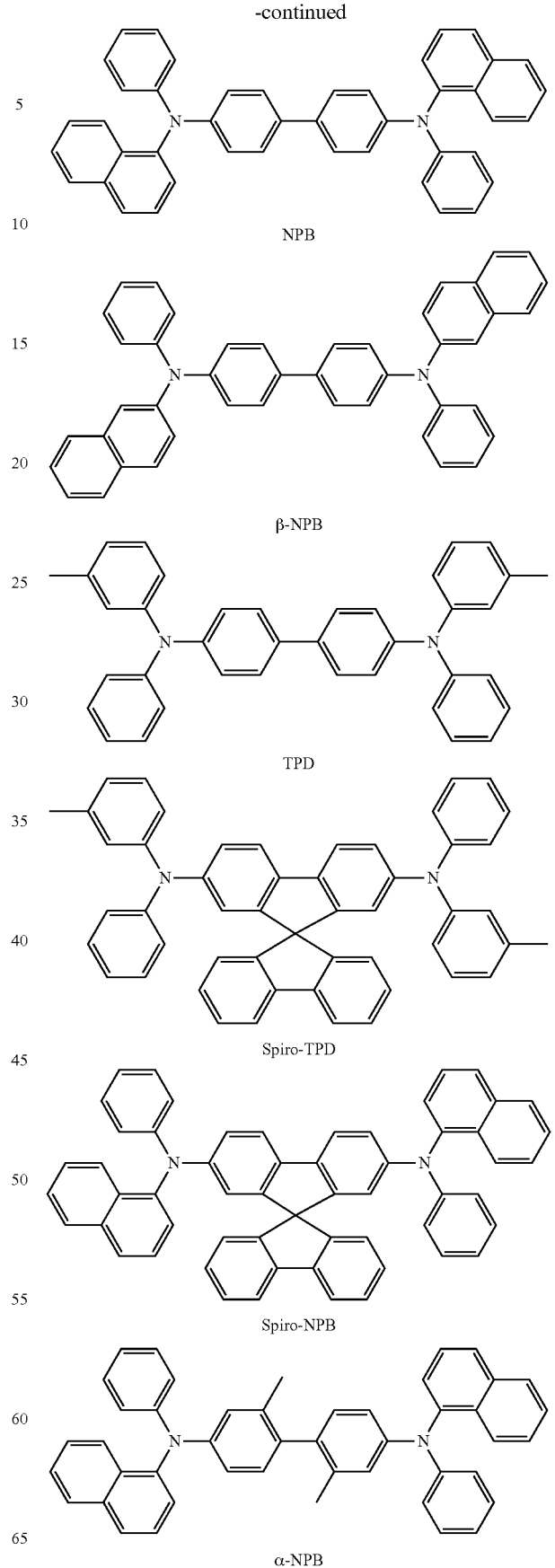

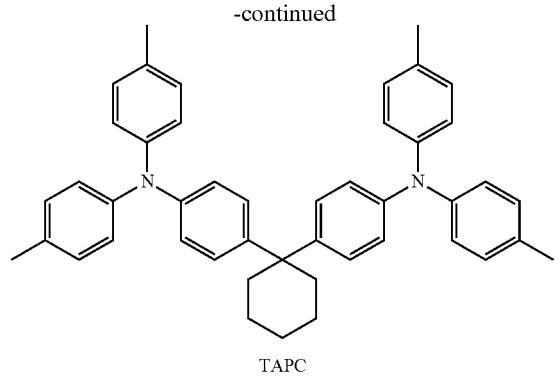

TAPC

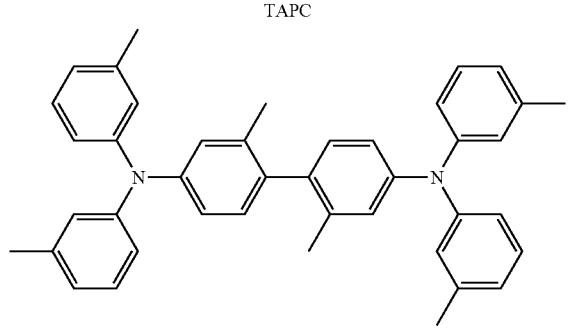

HMTPD

<Formula 201>

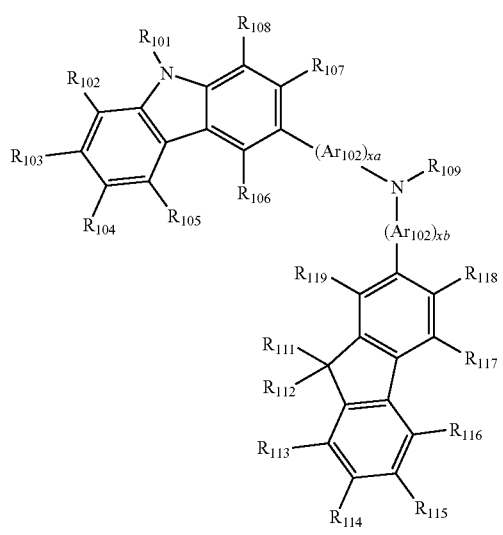

<Formula 202>

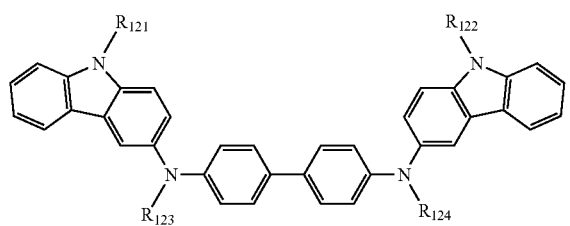

In the Formula 201, $Ar_{101}$ and $Ar_{102}$ are independently a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group or a pentacenylene group; or a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group or a pentacenylene group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic heterocondensed polycyclic group.

In the Formula 201, the xa and xb may be independently integers of 0 to 5, or 0, 1 or 2. For example, the xa may be 1, xa and xb may be 0, but are not limited thereto.

In the Formulae 201 and 202, the $R_{101}$ to $R_{108}$, $R_{111}$ to $R_{119}$ and $R_{121}$ to $R_{124}$ may be independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and the like) or a $C_1$-$C_{10}$ alkoxy group (for example, a methoxy group, an ethoxy group, a propoxy group, a butoxy group, a pentoxy group, and the like);

a $C_1$-$C_{10}$ alkyl group or a $C_1$-$C_{10}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;

a phenyl group, a naphthyl group, an anthracenyl group, a fluorenyl group or a pyrenyl group; or a phenyl group, a naphthyl group, an anthracenyl group, a fluorenyl group or a pyrenyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but is not limited thereto.

In the Formula 201, $R_{109}$ is a phenyl group, a naphthyl group, an anthracenyl group or a pyridinyl group; or a phenyl group, a naphthyl group, an anthracenyl group or a pyridinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group and a $C_1$-$C_{20}$ alkoxy group.

According to one embodiment, the compound represented by the Formula 201 may be represented by the following Formula 201A, but is not limited thereto:

<Formula 201A>

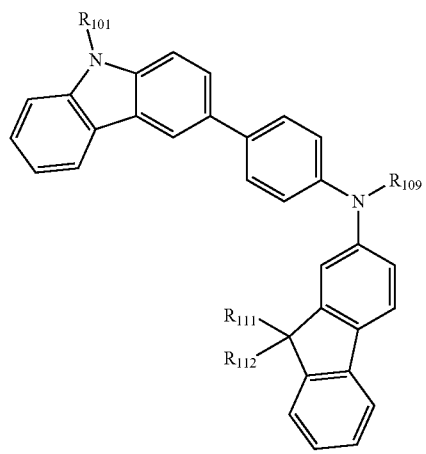

In the Formula 201A, the decreiptions for $R_{101}$, $R_{111}$, $R_{112}$ and $R_{109}$ refer to the

DETAILED DESCRIPTION

For example, the compound represented by the Formula 201 and the compound represented by the Formula 202 may include the following compounds HT1 to HT20, but are not limited thereto:

HT1

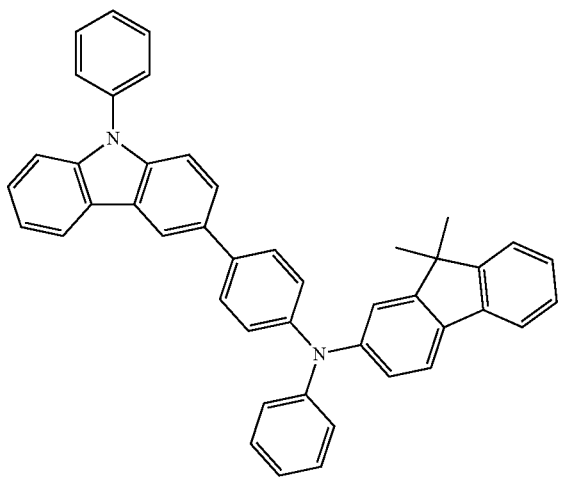

HT2

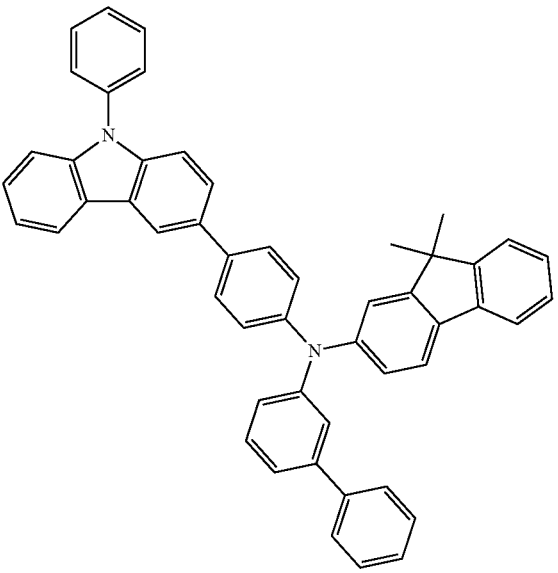

HT3

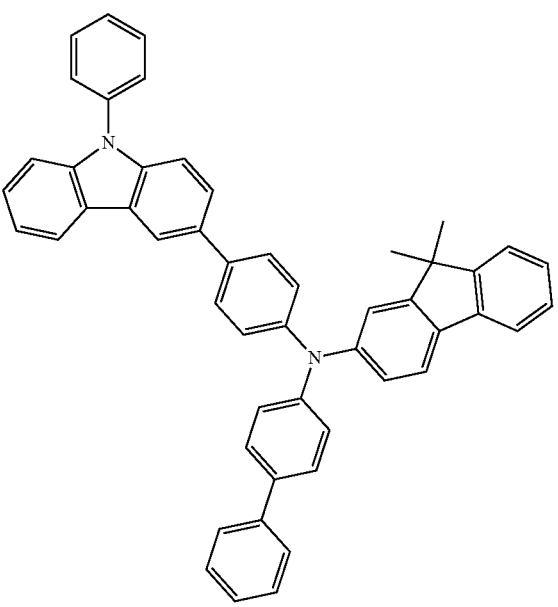

HT4
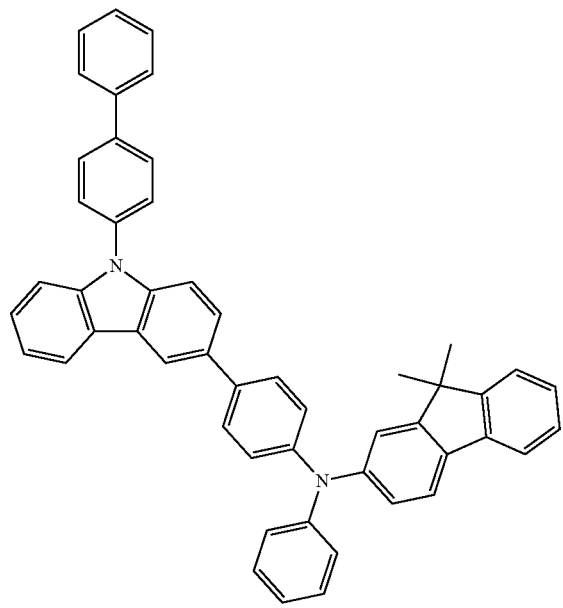
HT6
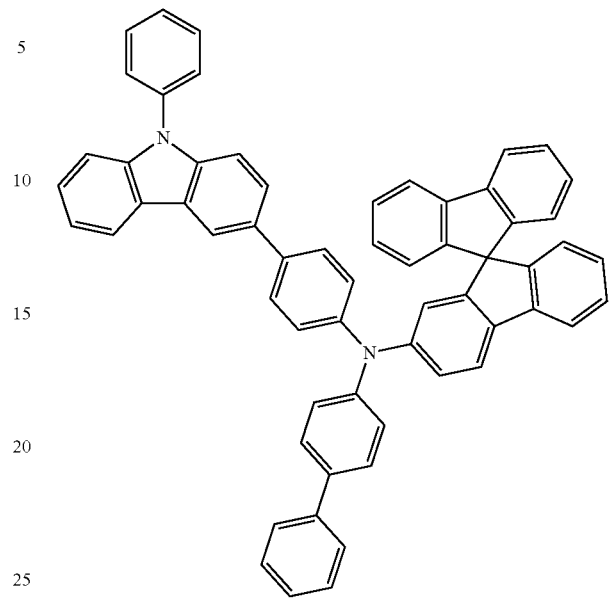
HT5
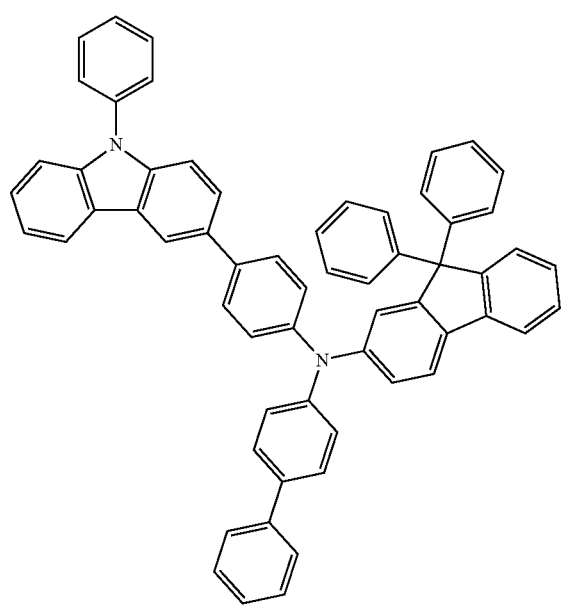
HT7
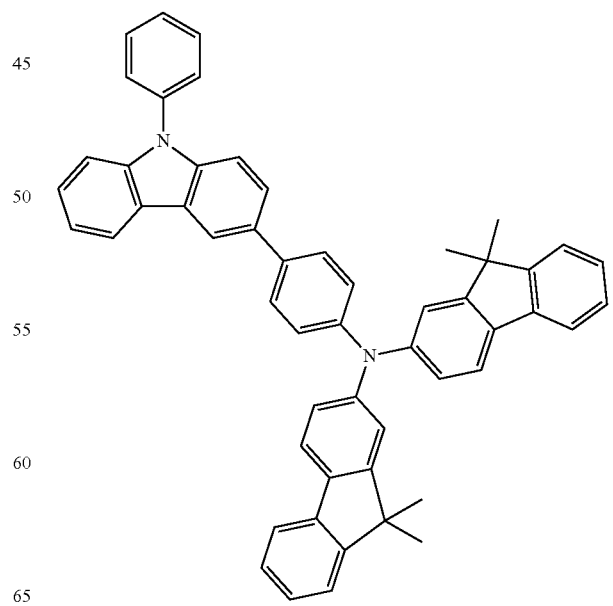

HT8
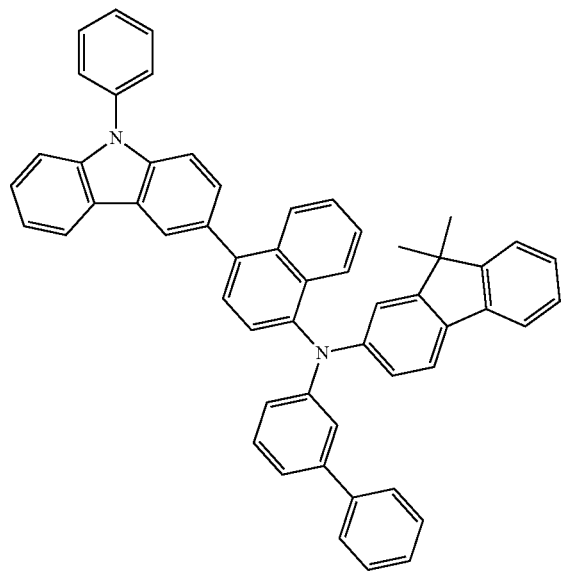
HT10
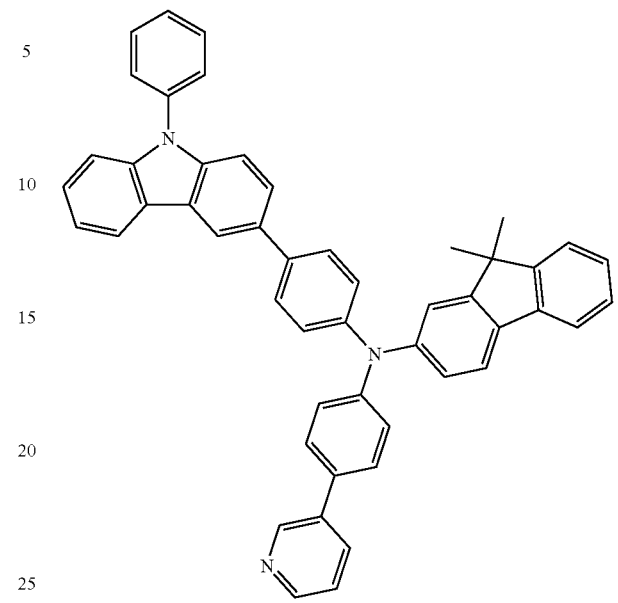
HT9
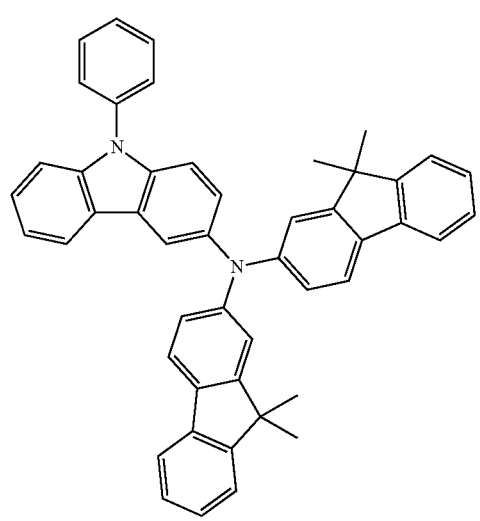
HT11

HT12
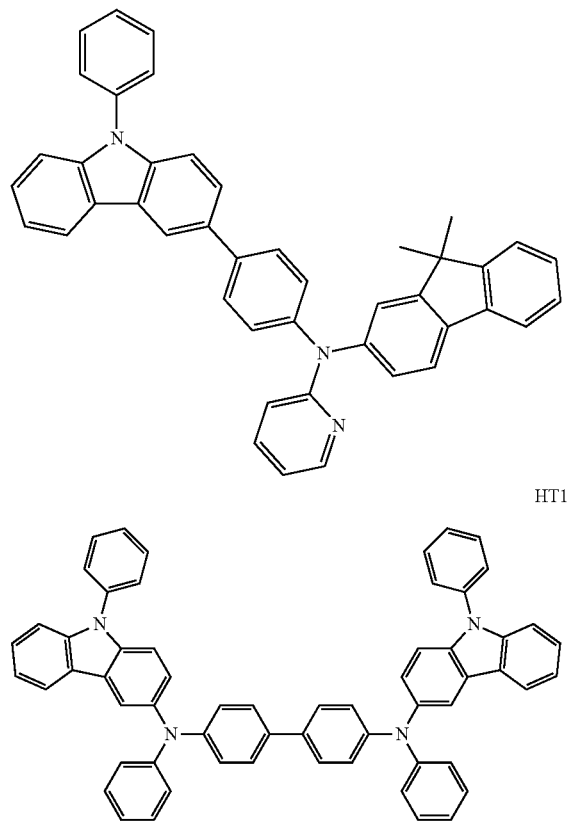
HT13
HT14
HT15
HT16
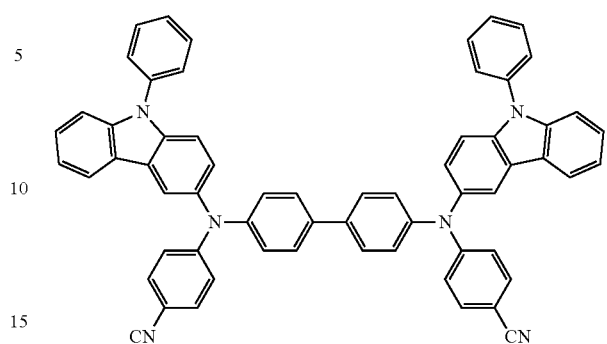
HT17
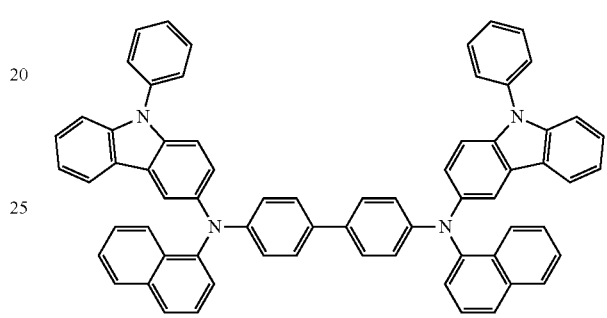
HT18
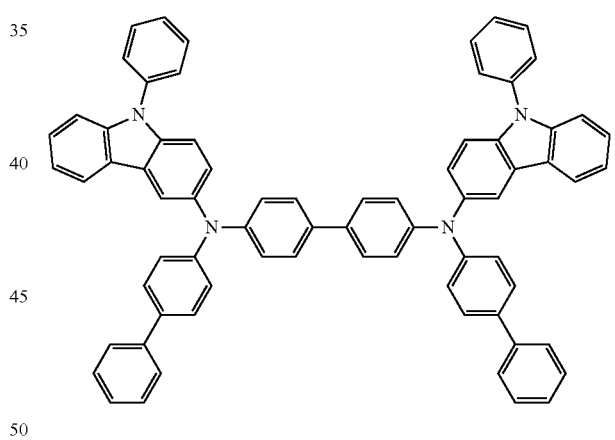
HT19
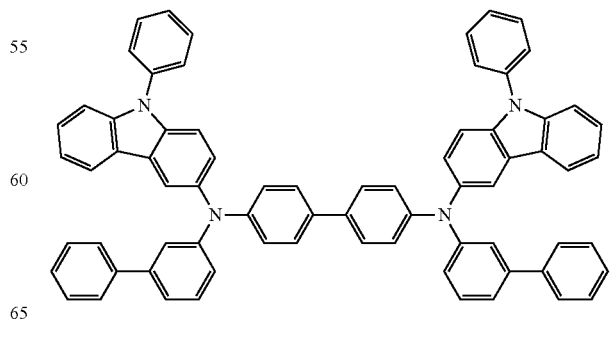

-continued

HT20

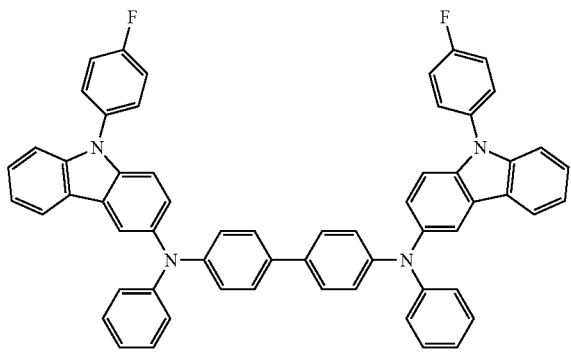

<F4-TCNQ>

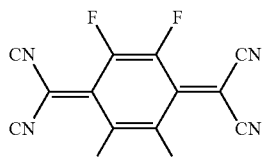

The hole transport region may be about 100 Å to about 10000 Å thick, for example, about 100 Å to about 1000 Å thick. When the hole transport region includes the hole injection layer (HIL) and the hole transport layer (HTL), the hole injection layer (HIL) may be about 100 Å to about 10000 Å thick, for example, about 100 Å to about 1000 Å thick, while the hole transport layer (HTL) may be about 50 Å to about 2000 Å thick, for example, about 100 Å to about 1500 Å thick. When the hole transport region, the hole injection layer (HIL) and the hole transport layer (HTL) have a thickness within the ranges, satisfactory hole transport characteristics may be obtained without substantially increasing a driving voltage.

The hole transport region may further include a charge-producing material other than the material to improve conductivity. The charge-producing material may be uniformly or non-uniformly dispersed in the hole transport region.

The charge-producing material may be, for example, a p-dopant. The p-dopant may be one of a quinone derivative, a metal oxide and a cyano group-containing compound but is not limited thereto. For example, non-limiting examples of the p-dopant may be a quinone derivative such as tetracyanoquinonedimethane (TCNQ) and 2,3,5,6-tetrafluoro-tetracyano-1,4-benzoquinonedimethane (F4-TCNQ) and the like; a metal oxide such as tungsten oxide, molybdenum oxide and the like; and a cyano group-containing compound such as the following compound HT-D1 and the like but is not limited thereto.

The hole transport region may further include a buffer layer.

The buffer layer may play a role of compensating an optical resonance distance depending on wavelength of light emitted from the emission layer and thus, increasing efficiency.

On the hole transport region, an emission layer (EML) may be formed in a vacuum deposition method, a spin coating method, a cast method, a LB method and the like. When the vacuum deposition method and the spin coating method are used to form the emission layer, their deposit and coating conditions may vary depending on a compound used therein and in general, may be selected out of almost the same condition range as that of the hole injection layer (HIL).

When the organic light emitting device is a full color organic light emitting device, the emission layer may be patterned in an order of a red emission layer, a green emission layer and a blue emission layer. Or, the emission layer has a structure of stacking the red emission layer, the green emission layer and/or the blue emission layer and thus, may be variously modified, for example, emits white light.

The emission layer may include a host and a dopant. The host may be a condensed cyclic compound represented by the Formula 1. According to one embodiment, the emission layer may be a green emission layer emitting green light.

The dopant in the emission layer is a fluorescent dopant emitting light according to a fluorescence emission mechanism or a phosphorescent dopant emitting light according to a phosphorescence emission mechanism.

According to another embodiment, the host includes a first host and a second host that are different from each other, wherein the first host includes the condensed cyclic compound represented by the Formula 1, the second host includes at least one of a first compound represented by the following Formula 41 and a second compound represented by the following Formula 61:

<Compound HT-D1>

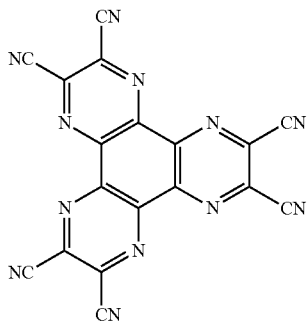

<Formula 41>

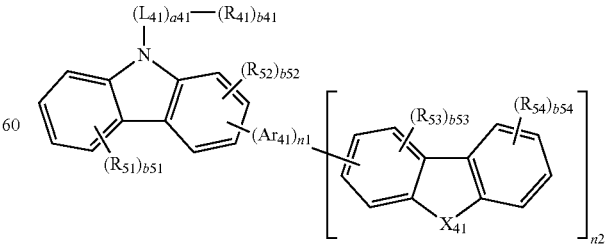

-continued

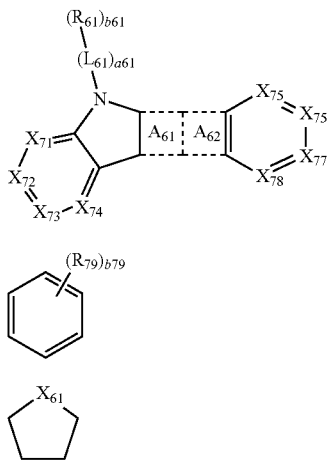

<Formula 61>

<Formula 61A>

<Formula 61B>

In the Formulae 41, 61, 61A and 61B
$X_{41}$ is N-[$(L_{42})_{a42}$-$(R_{42})_{b42}$], S, O, S(=O), S(=O)$_2$, C(=O), C($R_{43}$)($R_{44}$), Si($R_{43}$)($R_{44}$), P($R_{43}$), P(=O)$R_{43}$ or C=N($R_{43}$);

in the Formula 61, the ring $A_{61}$ is represented by the Formula 61A;

in the Formula 61, the ring $A_{62}$ is represented by the Formula 61B;

$X_{61}$ is N-[$(L_{62})_{a62}$-$(R_{62})_{b62}$], S, O, S(=O), S(=O)$_2$, C(=O), C($R_{63}$)($R_{64}$), Si($R_{63}$)($R_{64}$), P($R_{63}$), P(=O)$R_{63}$ or C=N($R_{63}$);

$X_{71}$ is C($R_{71}$) or N, $X_{72}$ is C($R_{72}$) or N, $X_{73}$ is C($R_{73}$) or N, $X_{74}$ is C($R_{74}$) or N, $X_{75}$ is C($R_{78}$) or N, $X_{76}$ is C($R_{76}$) or N, $X_{77}$ is C($R_{77}$) or N, $X_{78}$ is C($R_{78}$) or N;

the descriptions for $Ar_{41}$, $L_{41}$, $L_{42}$, $L_{61}$ and $L_{62}$ refer to description for $L_1$;

n1 and n2 are independently selected from integers of 0 to 3;

a41, a42, a61 and a62 are independently selected from integers of 0 to 3; $R_{41}$ to $R_{44}$, $R_{51}$ to $R_{54}$, $R_{61}$ to $R_{64}$ and $R_{71}$ to $R_{79}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), or —B($Q_6$)($Q_7$); and b41, b42, b51 to b54, b61, b62 and b79 are independently selected from integers of 1 to 3.

At least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_6$ heteroaryl group, the substituted monovalent non-aromatic condensed polycyclic group and substituted monovalent non-aromatic heterocondensed polycyclic group is, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{11}$)($Q_{12}$), —Si($Q_{13}$)($Q_{14}$)($Q_{16}$) and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{21}$)($Q_{22}$), —Si($Q_{23}$)($Q_{24}$)($Q_{25}$) and —B($Q_{26}$)($Q_{27}$); or
—N($Q_{31}$)($Q_{32}$), —Si($Q_{33}$)($Q_{34}$)($Q_{35}$) or —B($Q_{36}$)($Q_{37}$);

wherein the $Q_1$ to $Q_7$, $Q_{11}$ to $Q_{17}$, $Q_{21}$ to $Q_{27}$ and $Q_{31}$ to $Q_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group.

According to one embodiment, the $R_{41}$ to $R_{44}$, $R_{51}$ to $R_{54}$, $R_{61}$ to $R_{64}$ and $R_{71}$ to $R_{79}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with at least one of a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group; or —Si($Q_3$)($Q_4$)($Q_5$) (provided that, the $R_{13}$ to $R_{16}$ and $R_5$ and $R_6$ are not —Si($Q_3$)($Q_4$)($Q_5$));

wherein the $Q_3$ to $Q_5$ and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a Carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group, but are not limited thereto.

For example, the first compound may be represented by one of the following Formulae 41-1 to 41-12, and the second compound may be represented by one of the following Formulae 61-1 to 61-6:

Formula 41-1

Formula 41-2

Formula 41-3

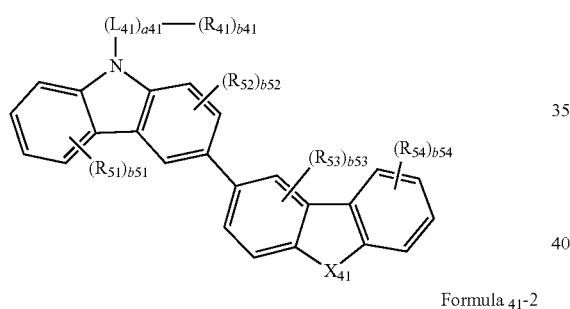

Formula 41-4

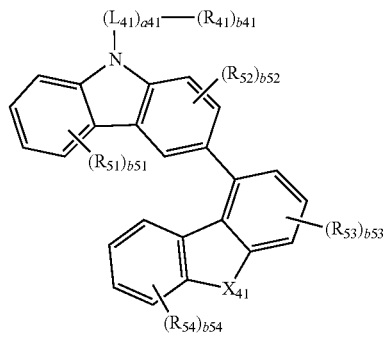

Formula 41-5

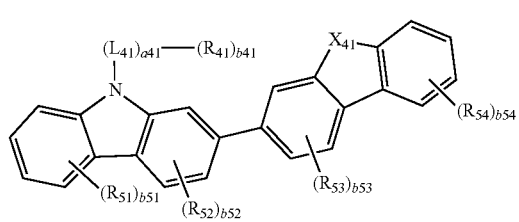

Formula 41-6

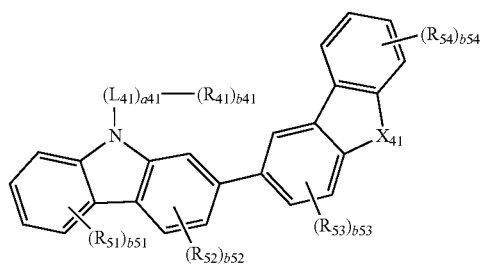

Formula 41-7

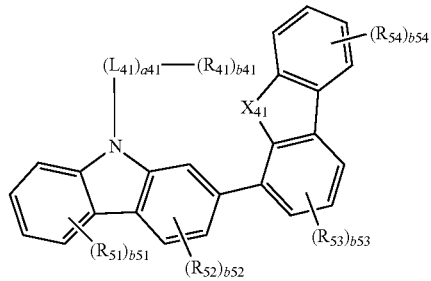

Formula 41-8

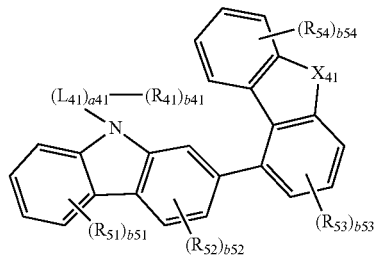

Formula 41-9

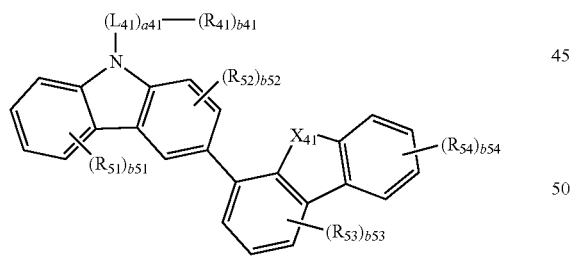

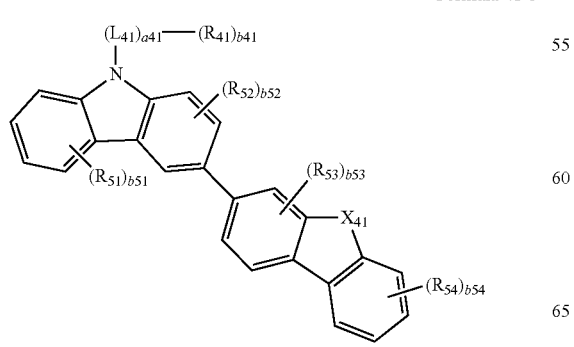

Formula 41-10
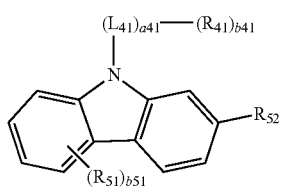

Formula 41-11
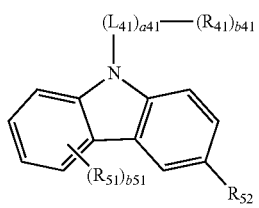

Formula 41-12
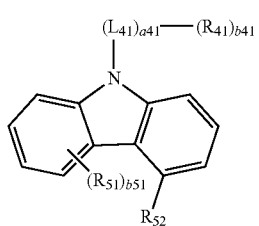

Formula 61-1
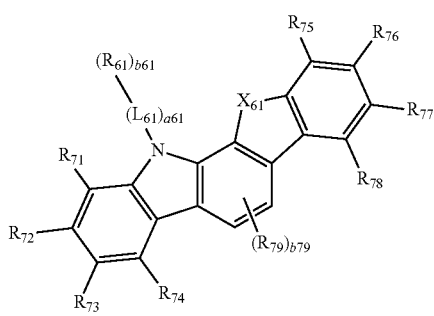

Formula 61-2
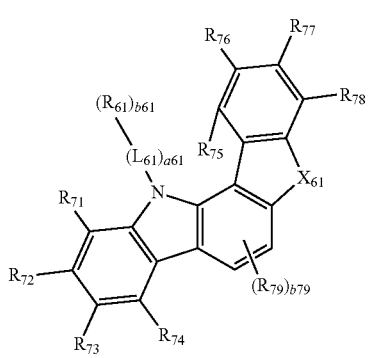

Formula 61-3
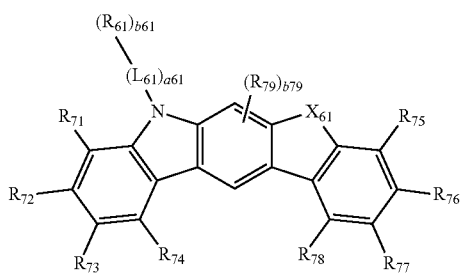

Formula 61-4
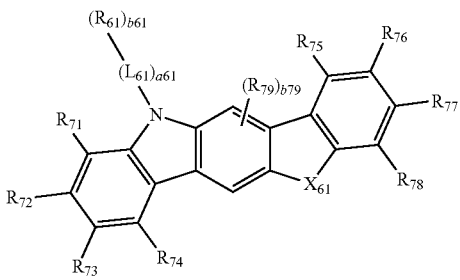

Formula 61-53
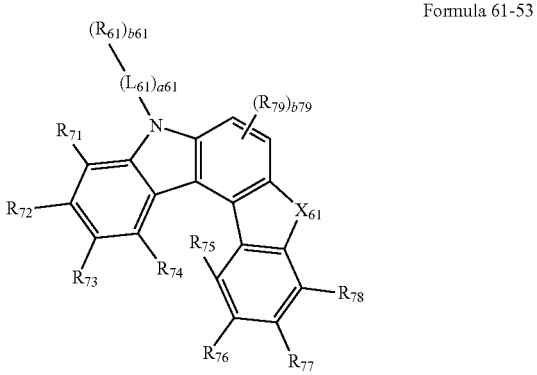

Formula 61-6
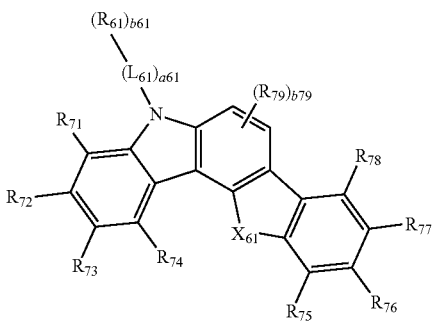

In the Formulae 41-1 to 41-12 and 61-1 to 61-6, descriptions for $X_{41}$, $X_{61}$, $L_{41}$, a41, $L_{61}$, a61, $R_{41}$, b41, $R_{52}$ to $R_{54}$, b52 to b54, $R_{61}$, b61, $R_{71}$ to $R_{79}$ and b79 refer to the above descriptions.

According to one embodiment, the first compound represented by the Formula 41 may include one of the following compounds A1 to A83, and the second compound represented by Formula 61 may include one of the following compounds B1 to B20:

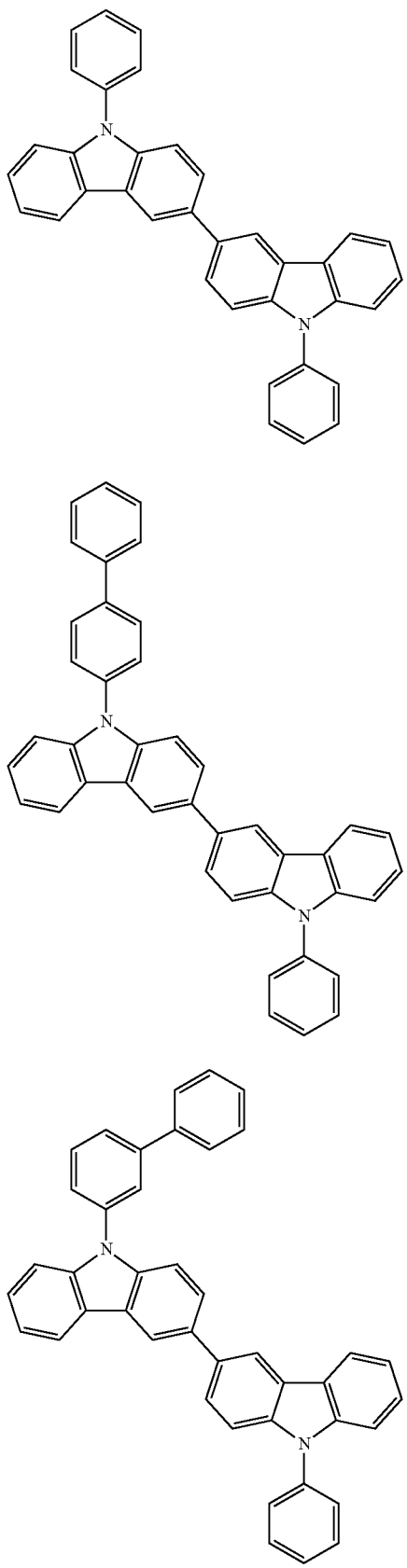
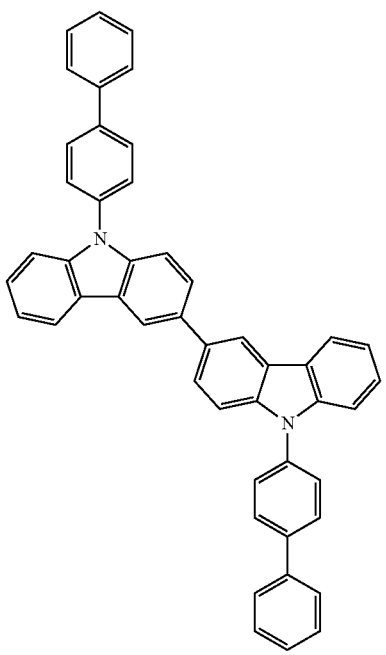
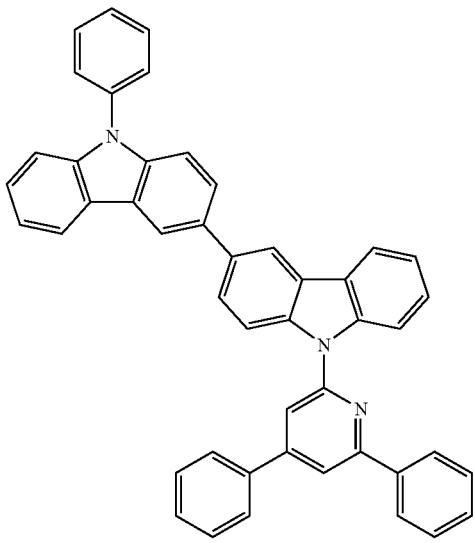

A6
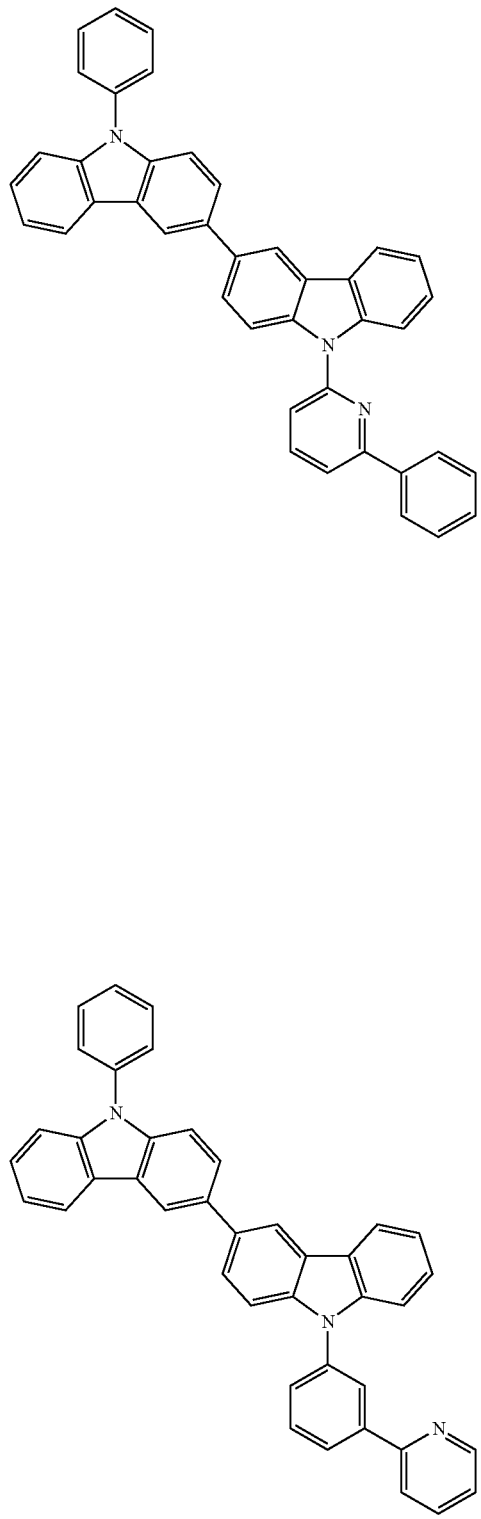
A7
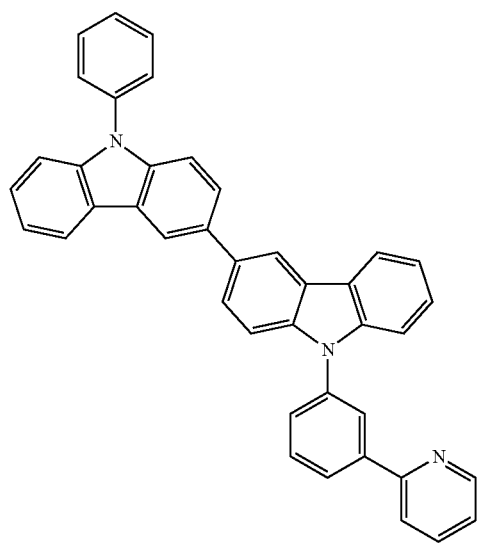
A8
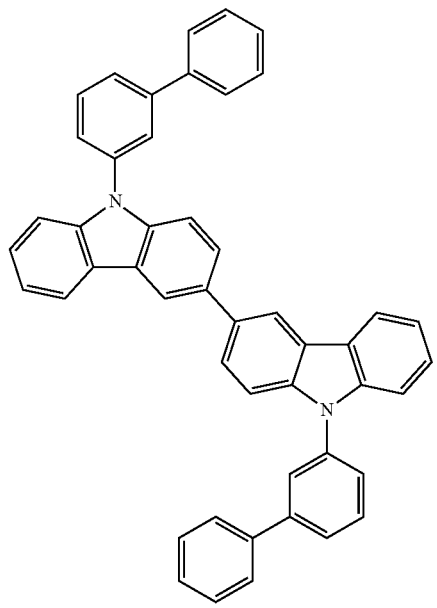
A9
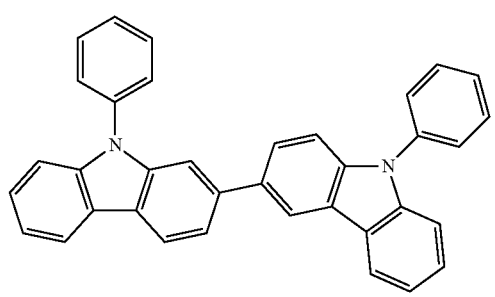
A10
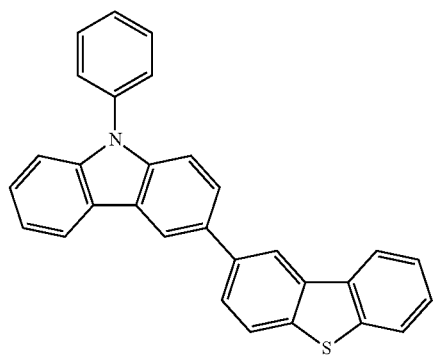
A11
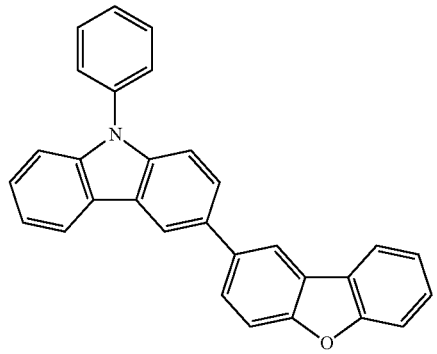

A12
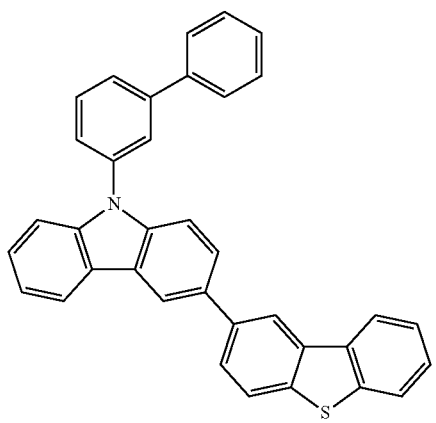
A13
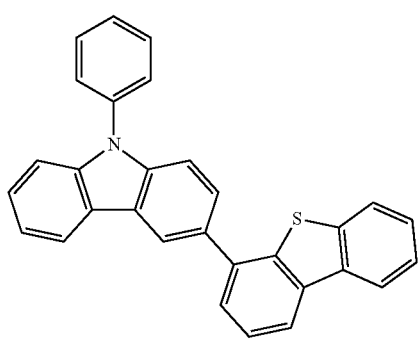
A14
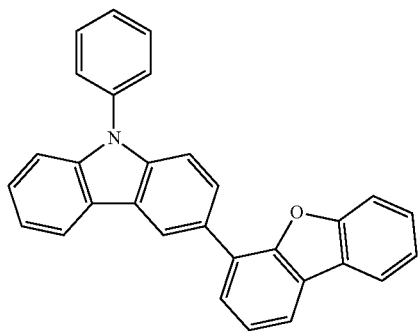
A15
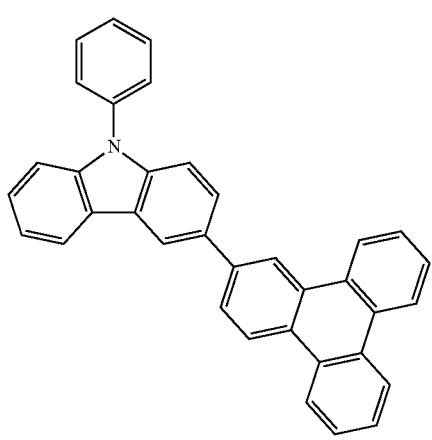
A16
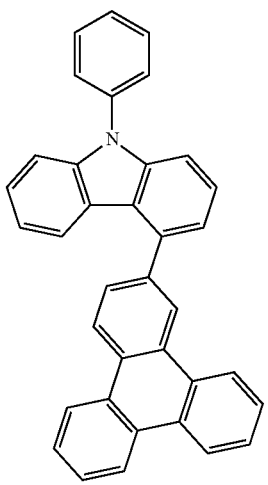
A17
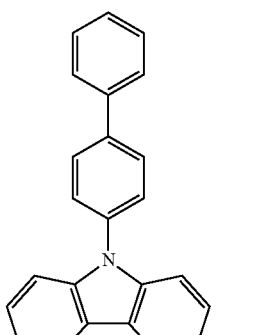
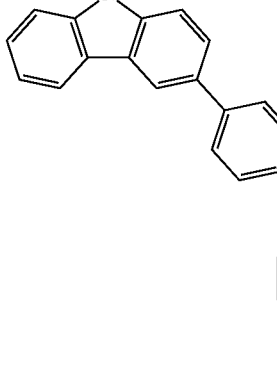
A18
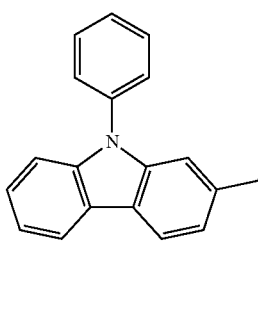

A19
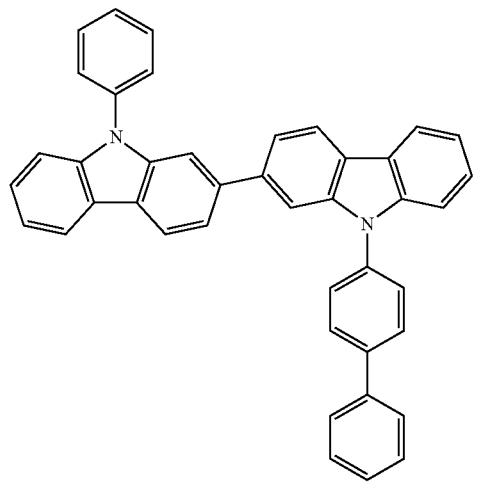
A20
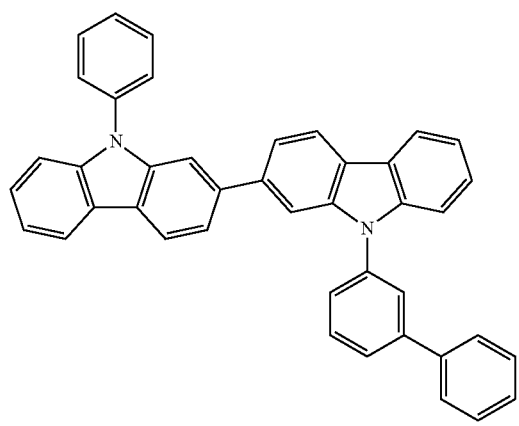
A21
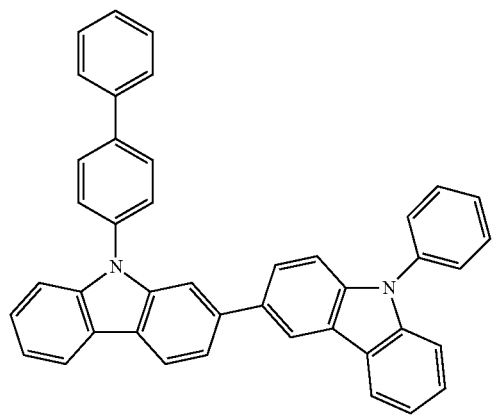
A22
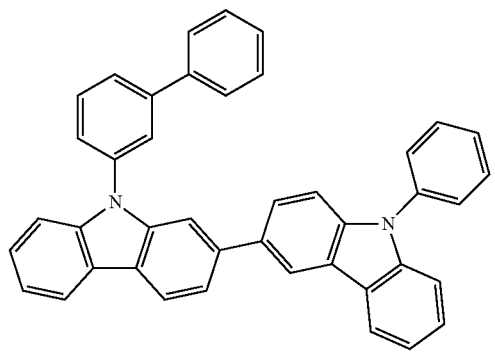
A23
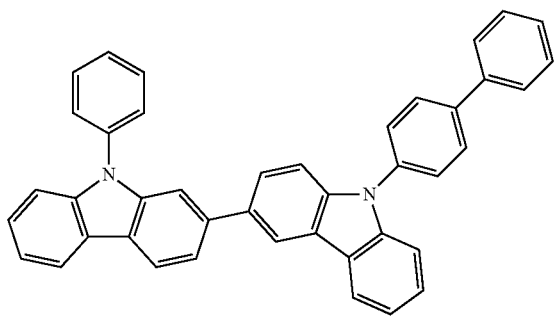
A24
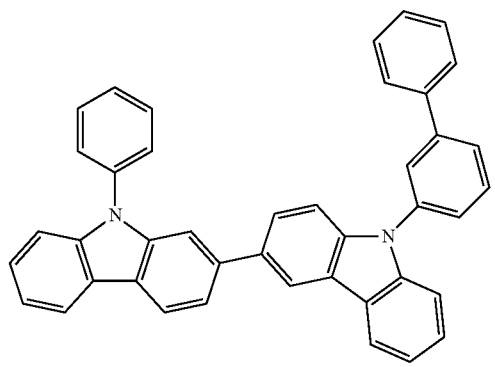
A25
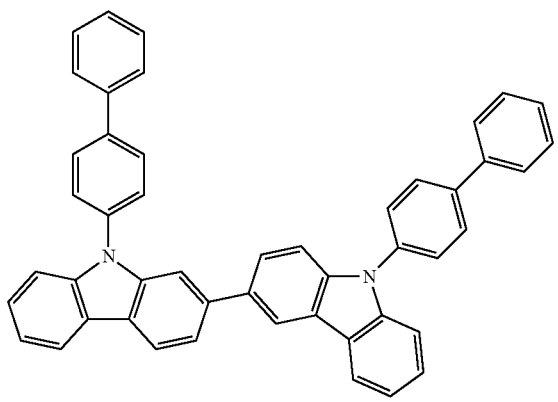

A26
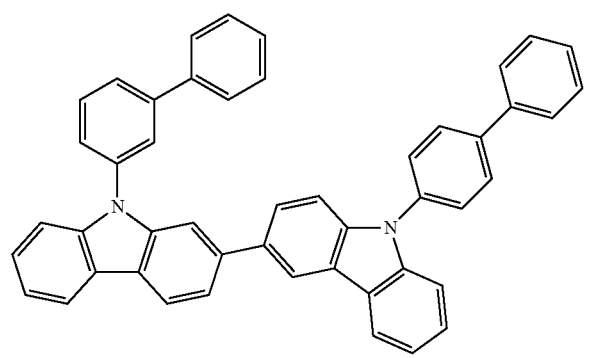
A27
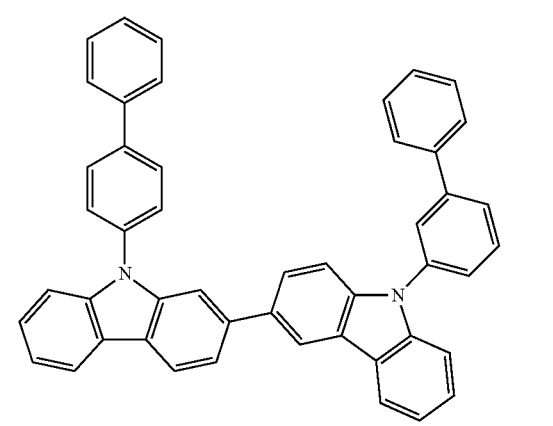
A28
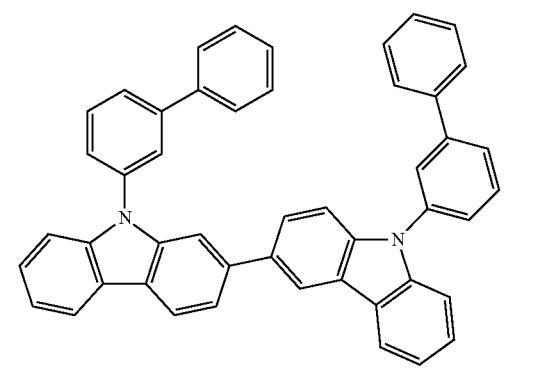
A29
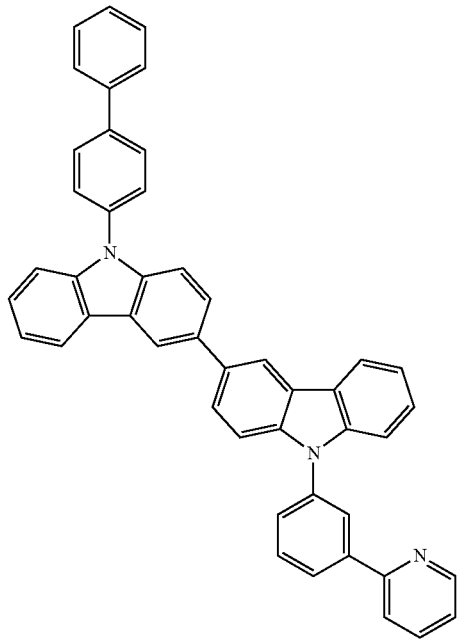
A30
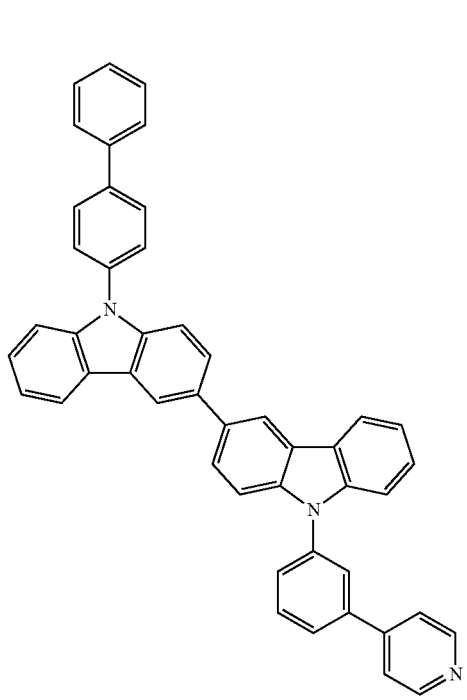

A31
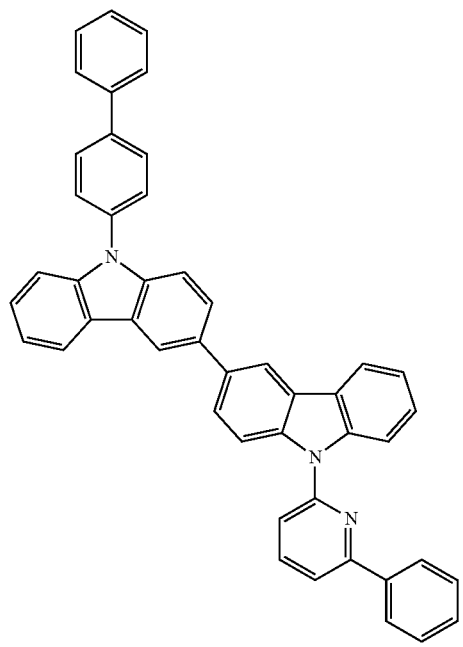
A32
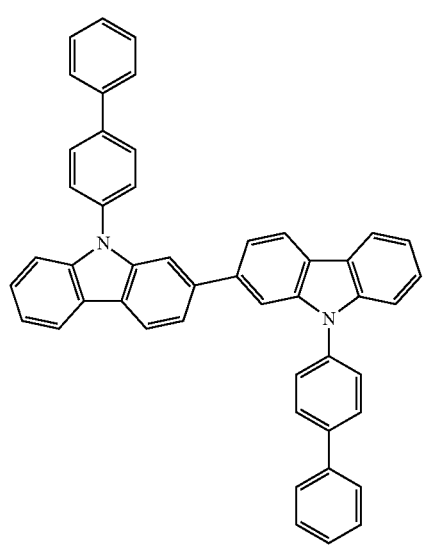
A33
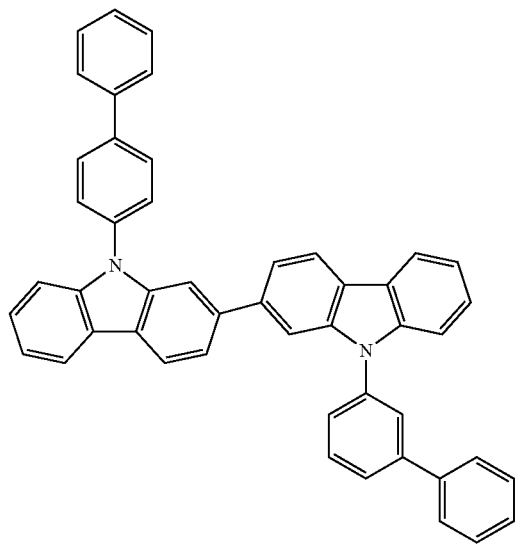
A34
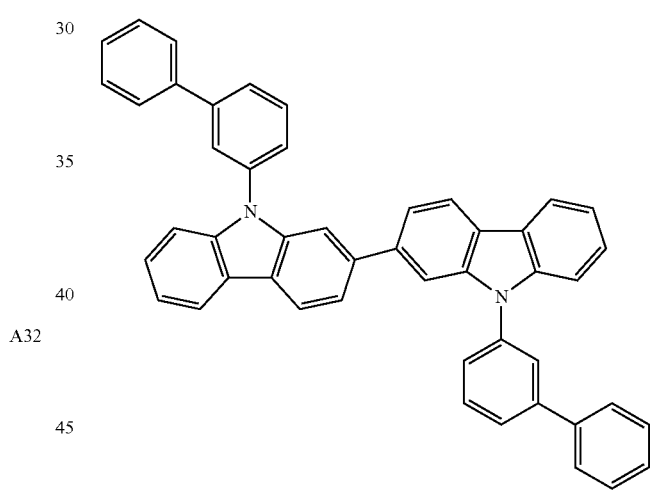
A35
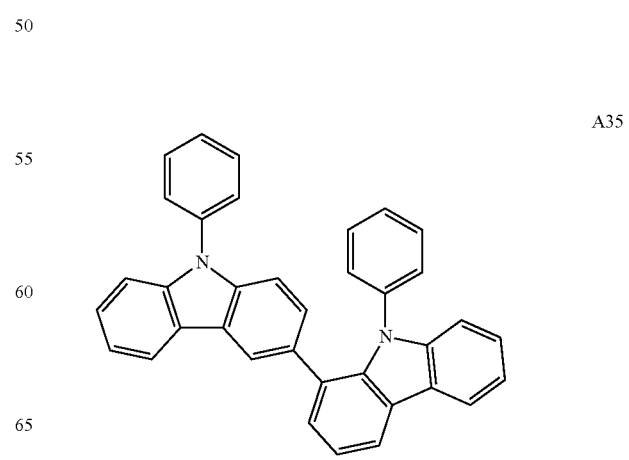

A36
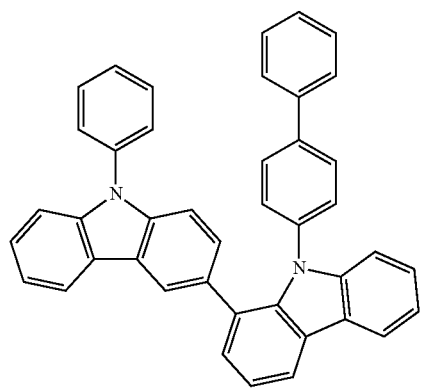
A37
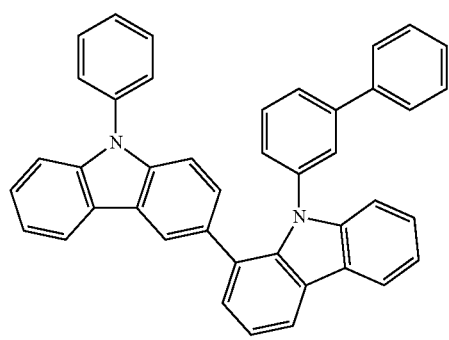
A38
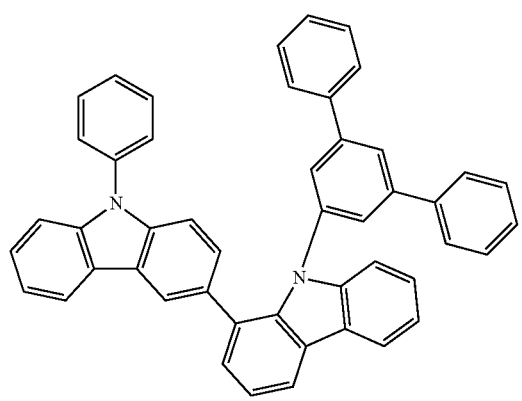
A39
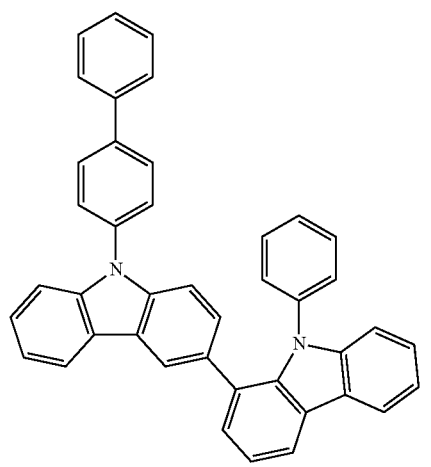
A40
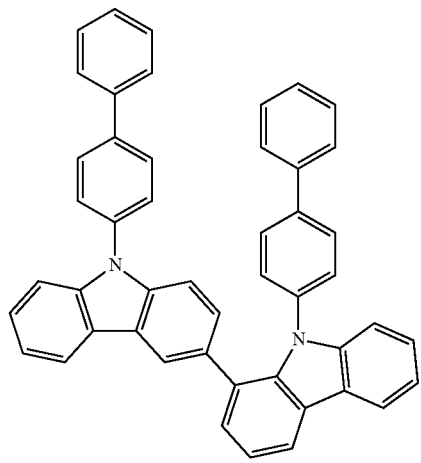
A41
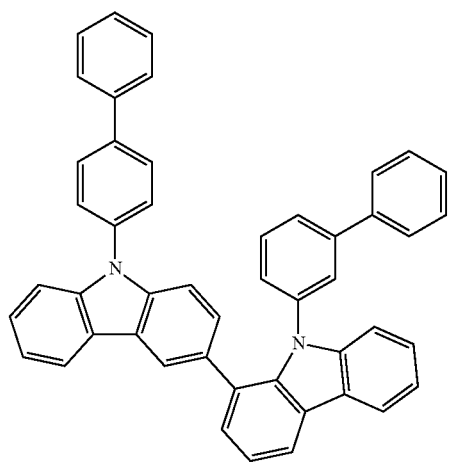
A42
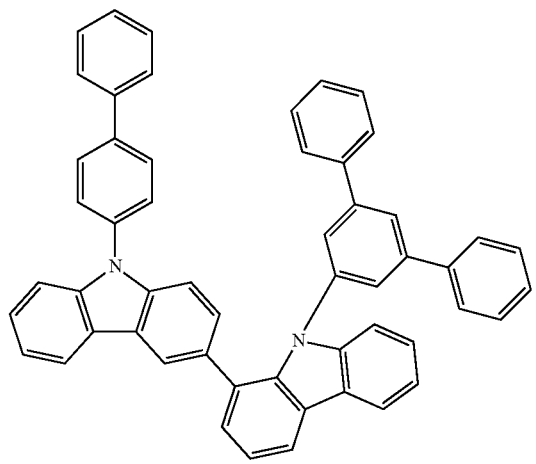

A43
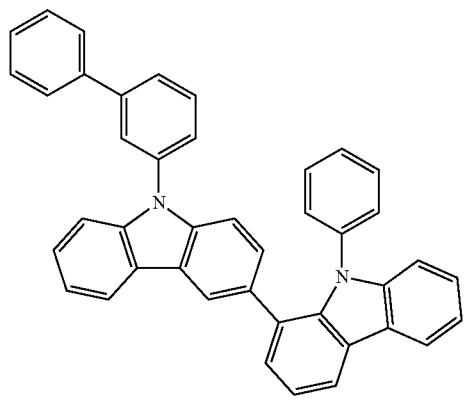
A44
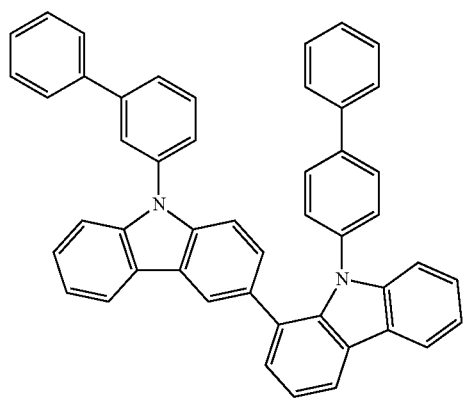
A45
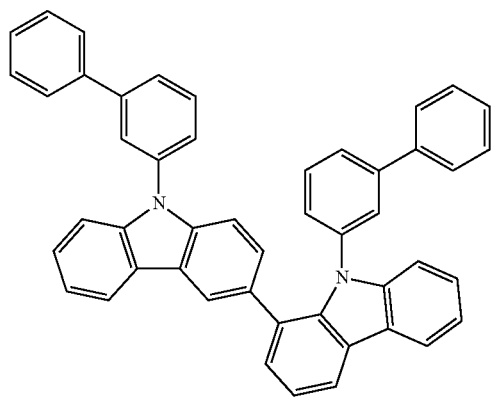
A46
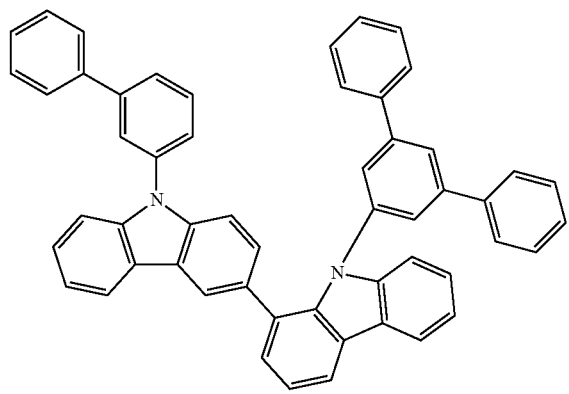
A47
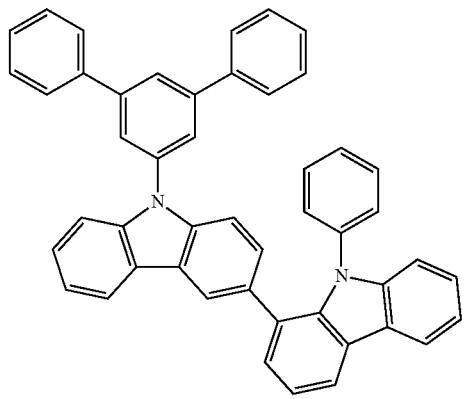
A48
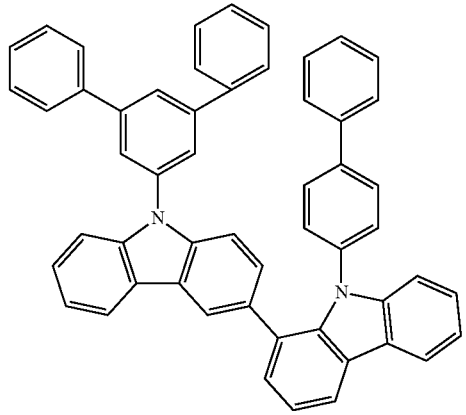
A49
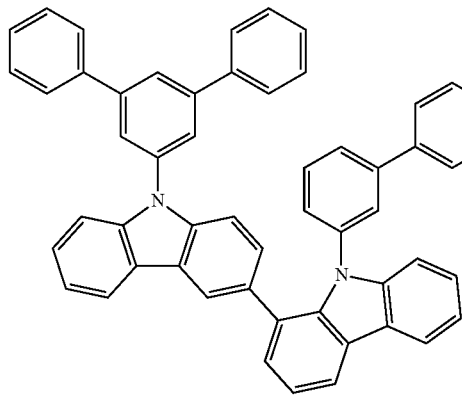
A50
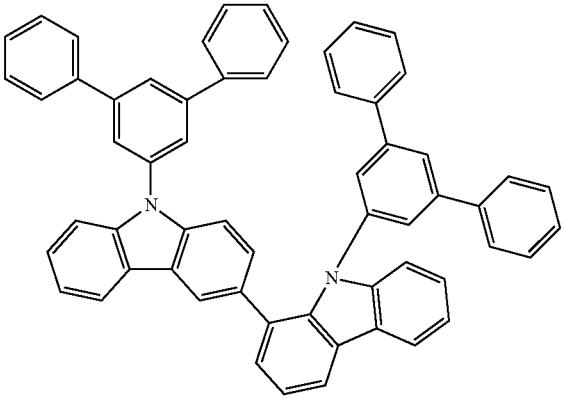

A51
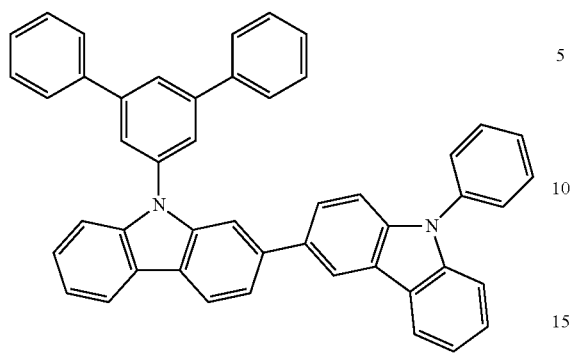
A52
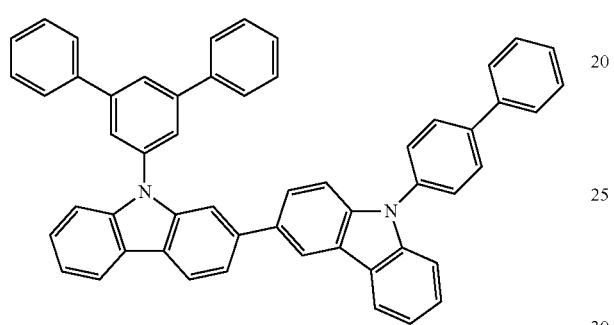
A53
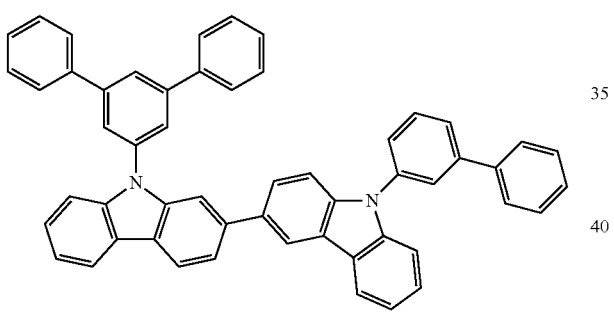
A54
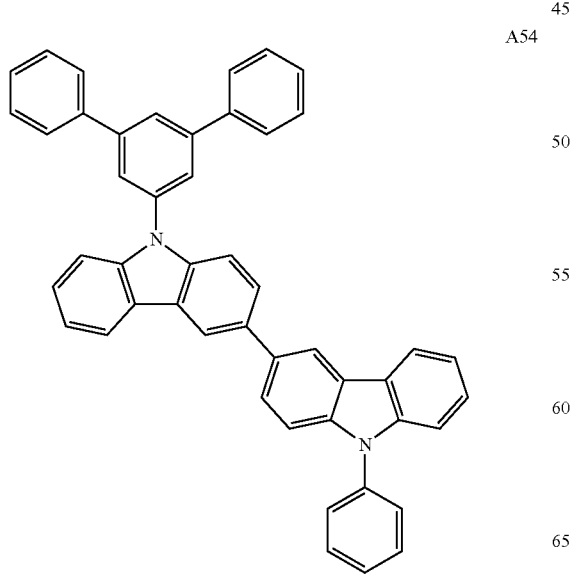
A55
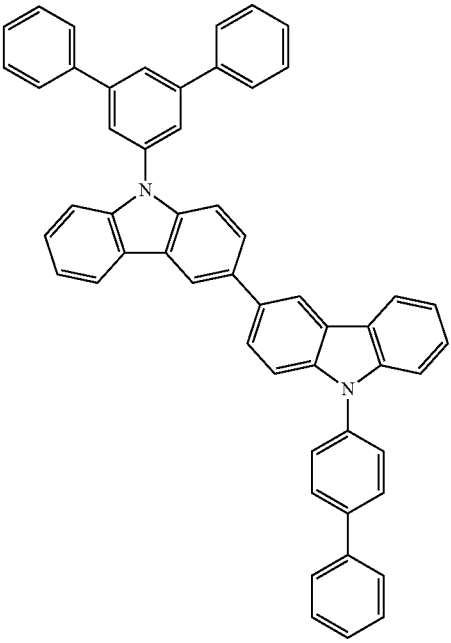
A56
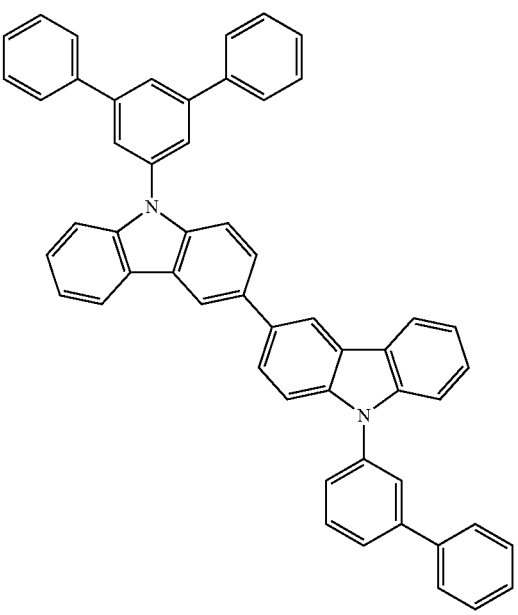

A57
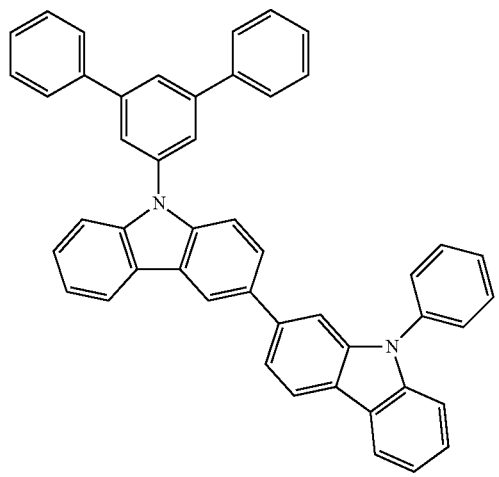
A58
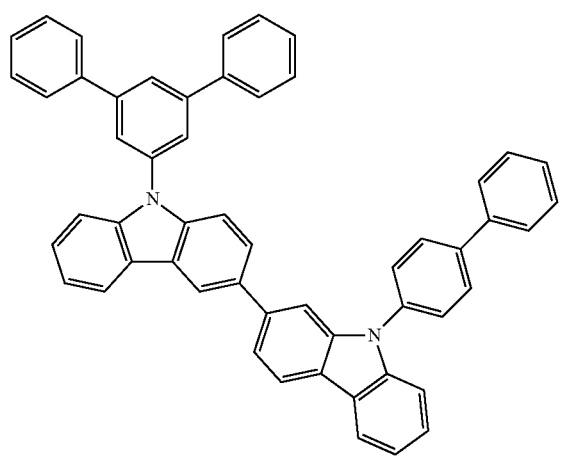
A59
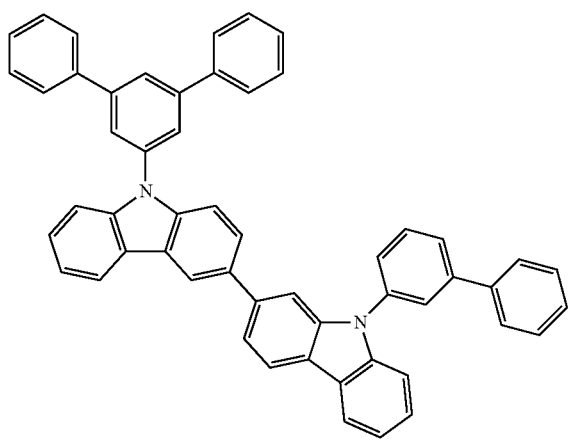
A60
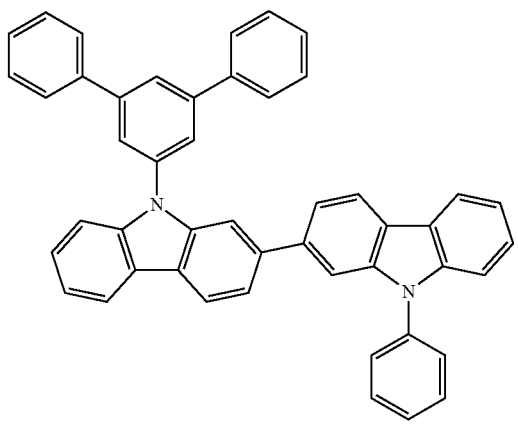
A61
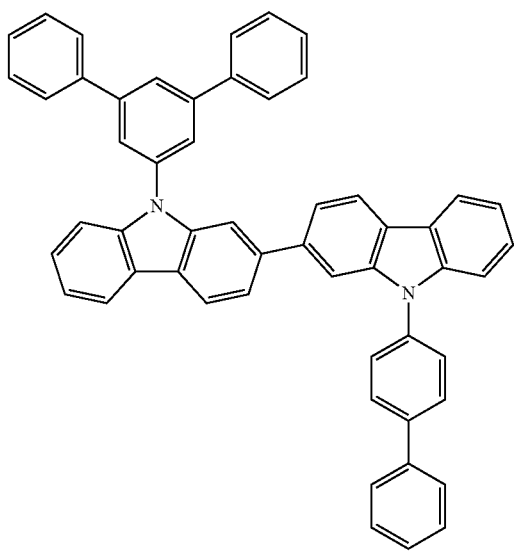
A62
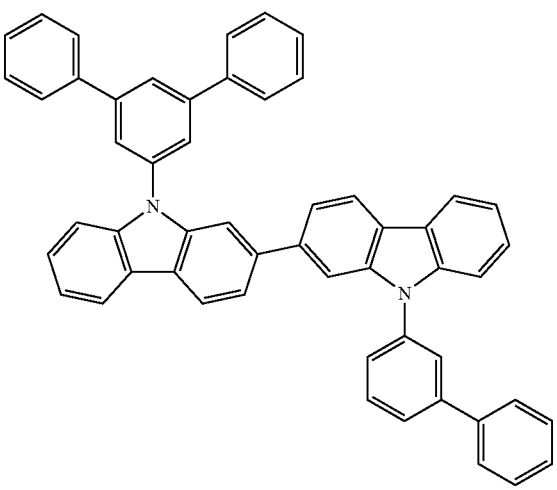

A63 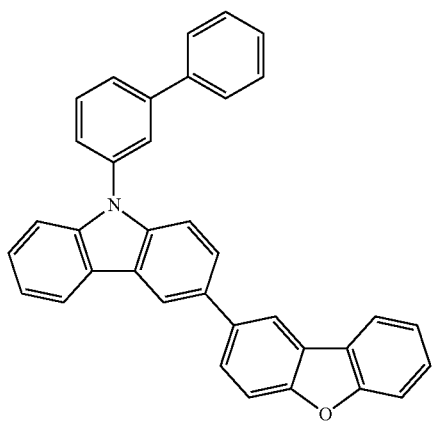
A64 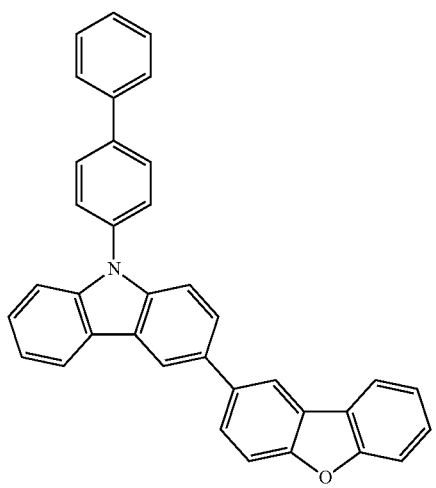
A65 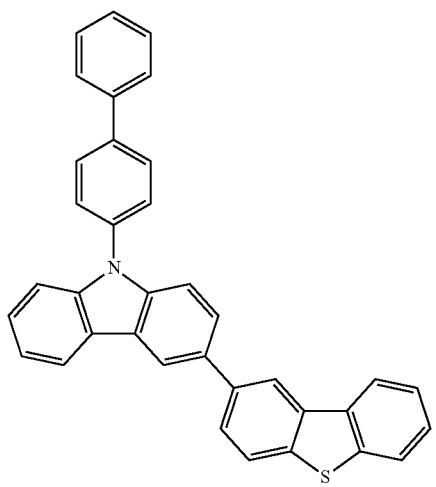
A66 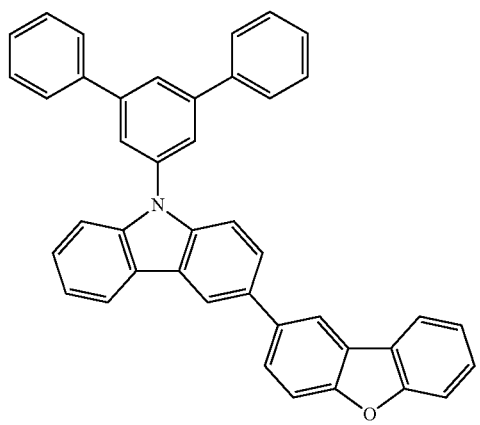
A67 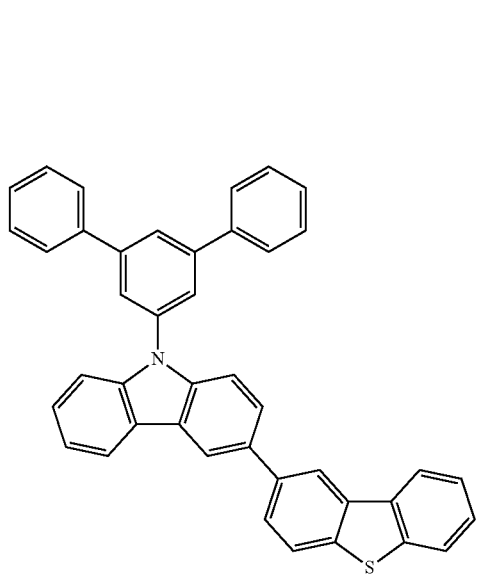
A68 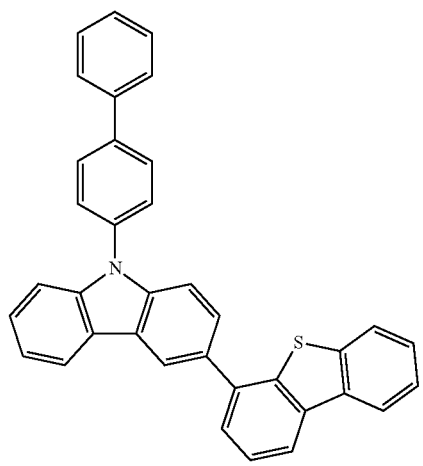

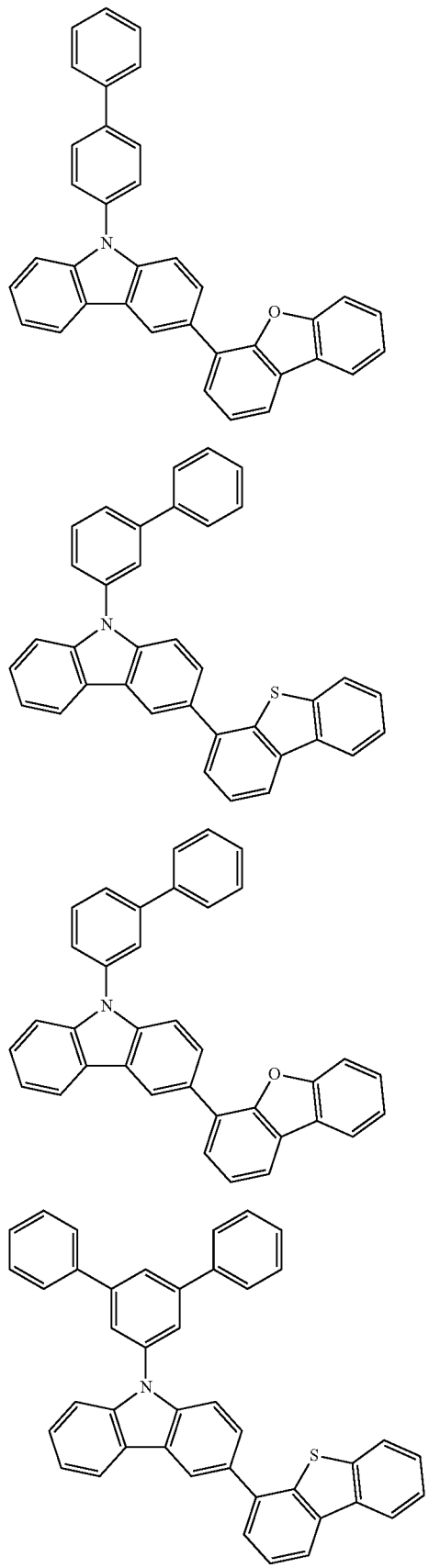
A69
A70
A71
A72
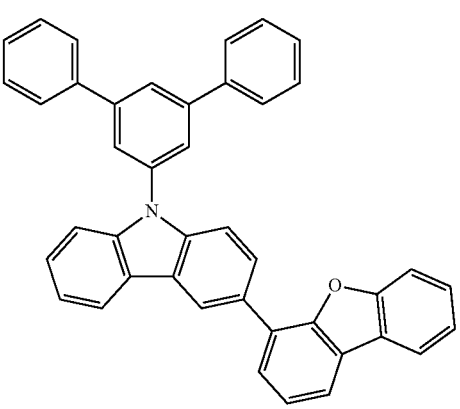
A73
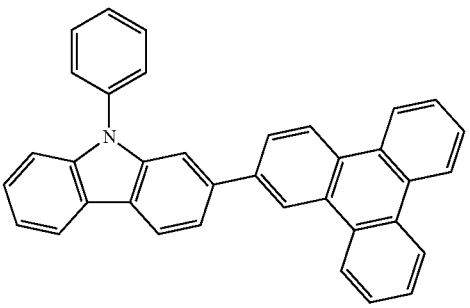
A74
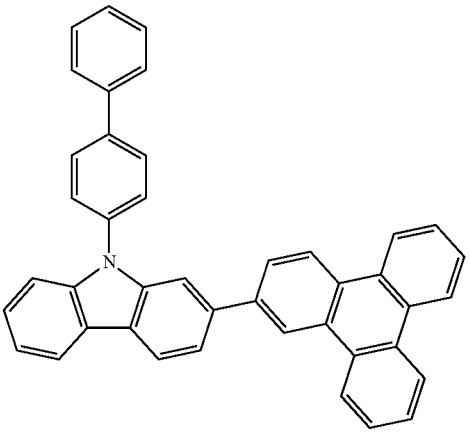
A75

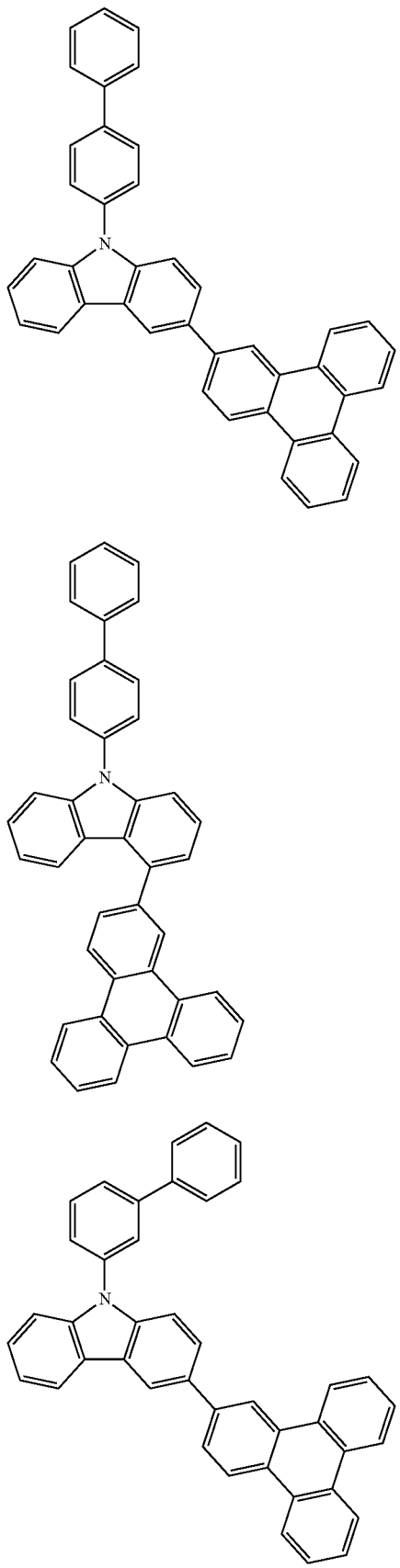
A76
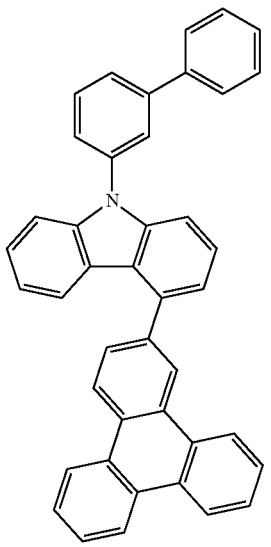
A77
A79
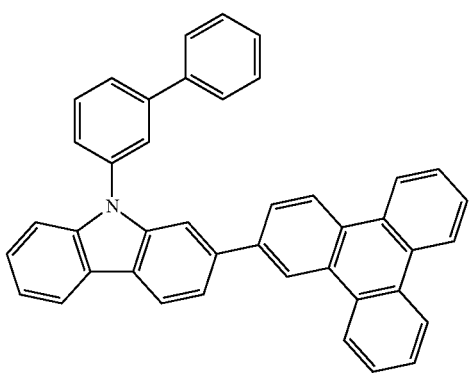
A80
A78
A81
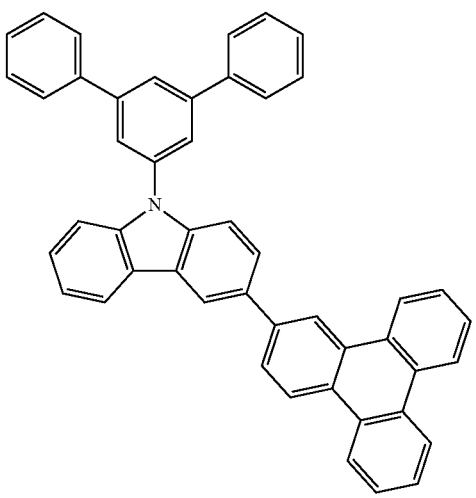

A82 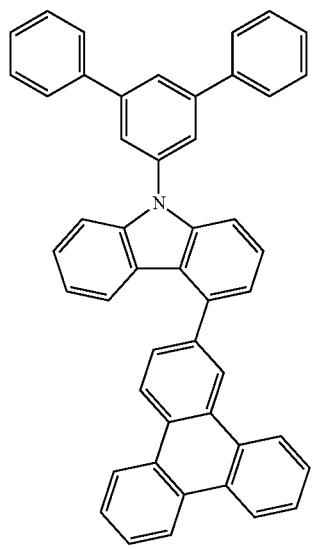
A83 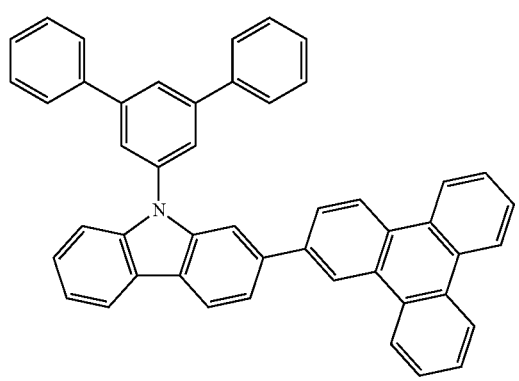
B1 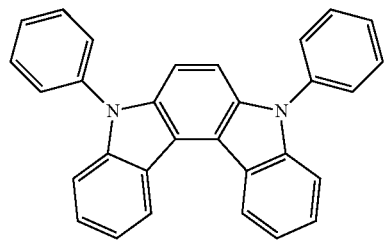
B2 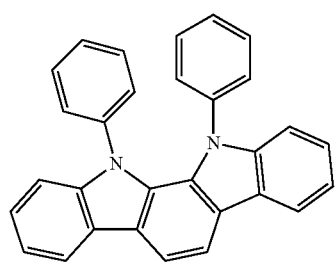
B3 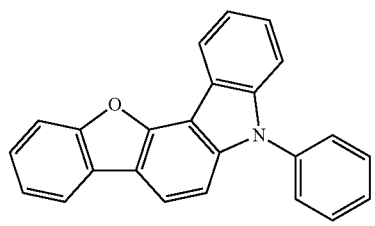
B4 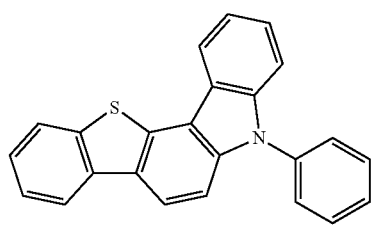
B5 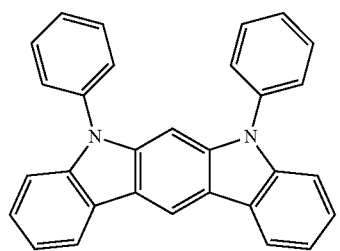
B6 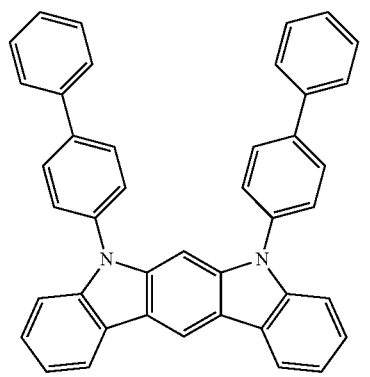
B7 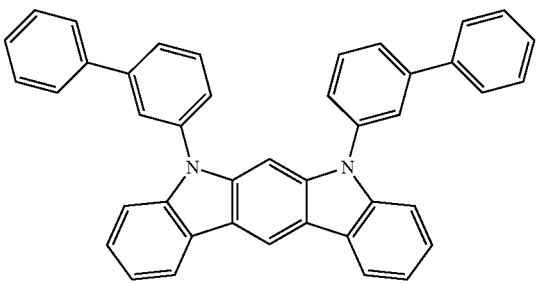

B8
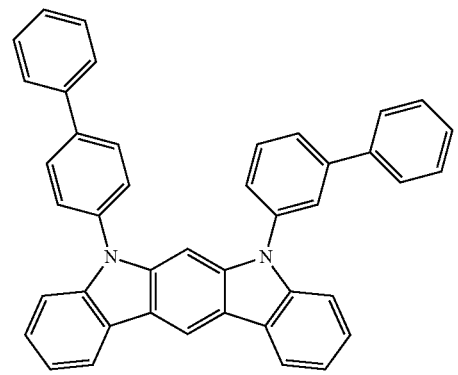
B9
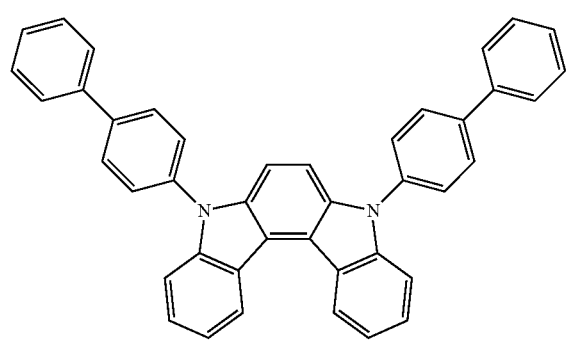
B10
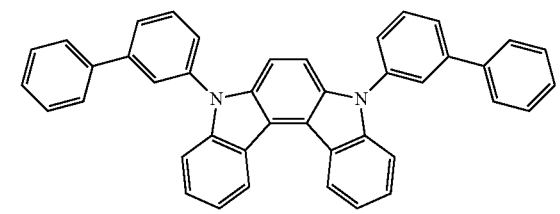
B11
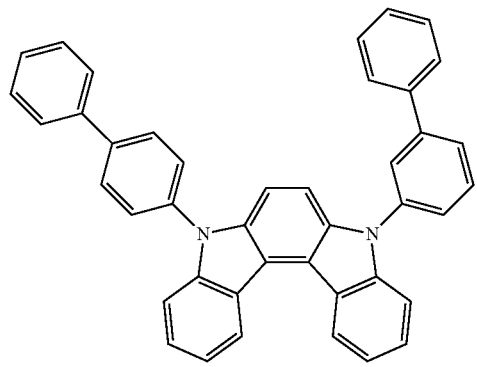
B12
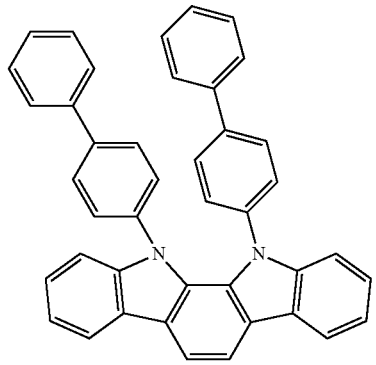
B13
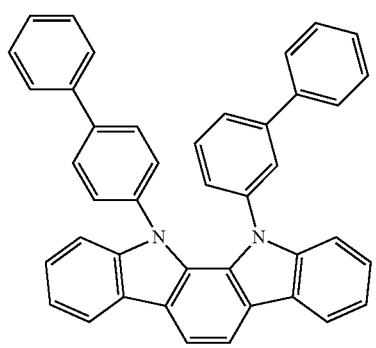
B14
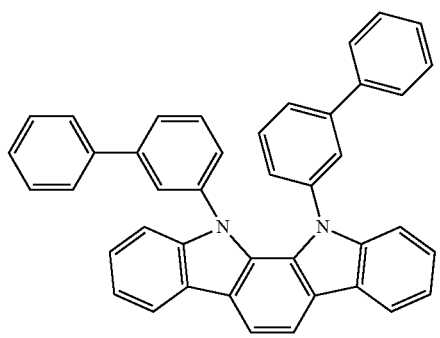
B15
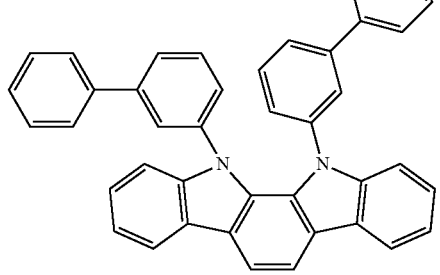
B16
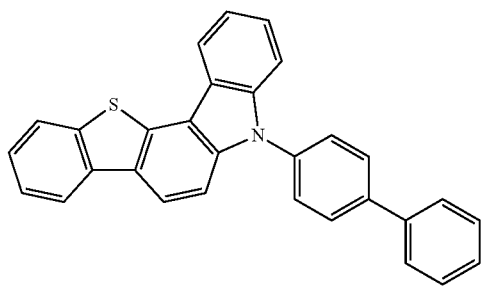

B17

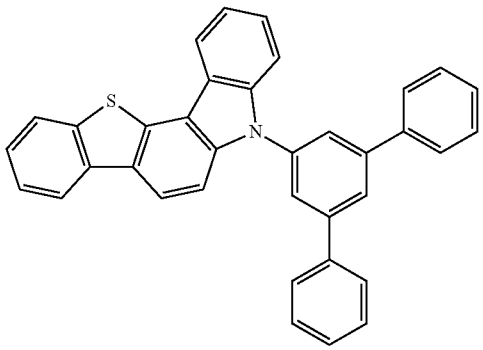

B18

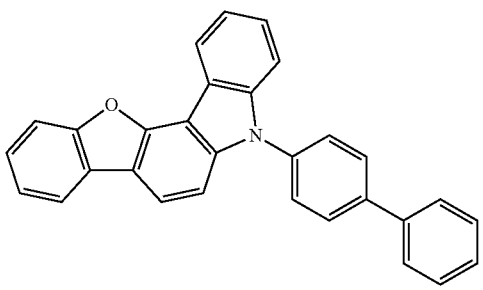

B19

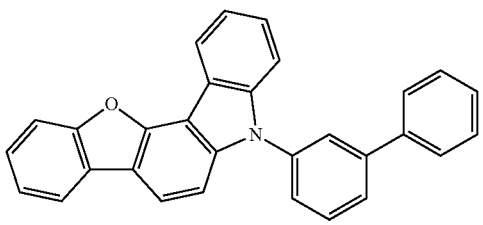

B20

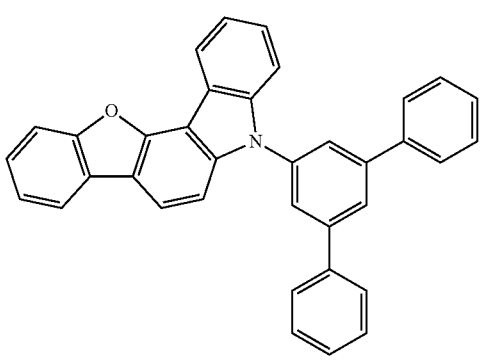

The phosphorescent dopant may include an organometallic compound represented by the following Formula 81:

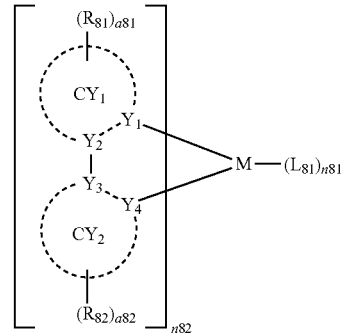

<Formula 81>

In the Formula 81,

M is iridium (Ir), platinum (Pt), osmium (Os), titanium (Ti), zirconium (Zr), hafnium (Hf), europium (Eu), terbium (Tb) or thulium (Tm);

$Y_1$ to $Y_4$ are independently carbon (C) or nitrogen (N);

$Y_1$ and $Y_2$ are linked to each other through a single bond or a double bond, $Y_3$ and $Y_4$ are linked to each other through a single bond or a double bond;

$CY_1$ and $CY_2$ are independently benzene, naphthalene, fluorene, spiro-fluorene, indene, pyrrole, thiophene, furan, imidazole, pyrazole, thiazole, isothiazole, oxazole, isoxazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran or dibenzothiophene, wherein $CY_1$ and $CY_2$ are optionally linked to each other through a single bond or an organic linking group;

$R_{81}$ and $R_{82}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), or —B($Q_6$)($Q_7$);

a81 and a82 are independently selected from integers of 1 to 5;

n81 selected from integers of 0 to 4;

n82 is 1, 2 or 3; and $L_{81}$ is a monovalent organic ligand, a divalent organic ligand or a trivalent organic ligand.

The descriptions for the $R_{81}$ and $R_{82}$ refer to the description for $R_{41}$.

The phosphorescent dopant may include at least one of the following compounds PD1 to PD78, but is not limited thereto (the following compound PD1 is Ir(ppy)$_3$):

PD1
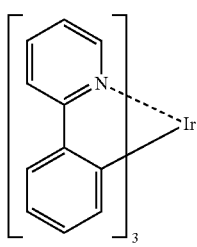
PD2
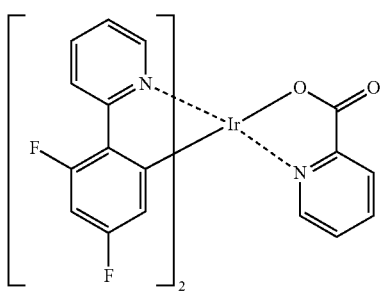
PD3
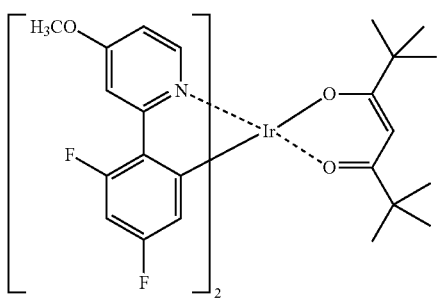
PD4
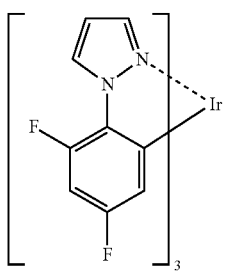
PD5
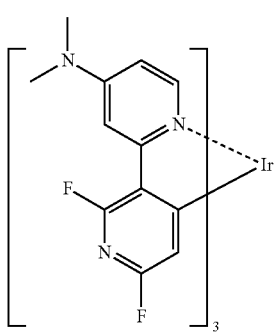
PD6
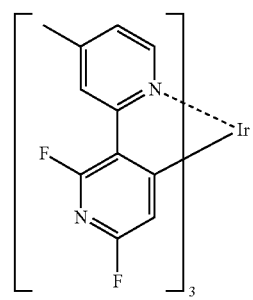
PD7
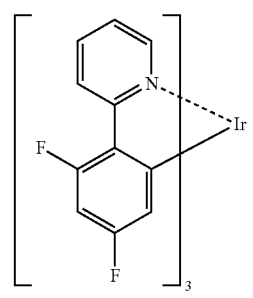
PD8
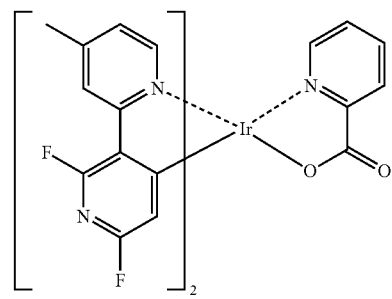
PD9
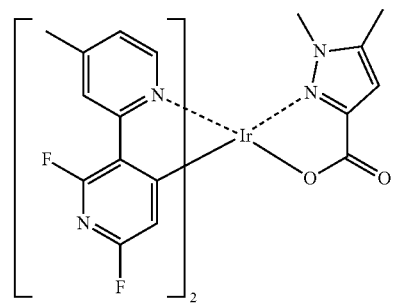
PD10
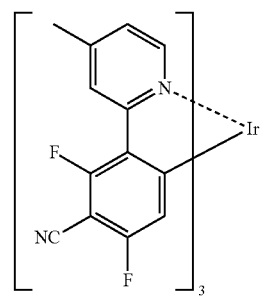

PF11
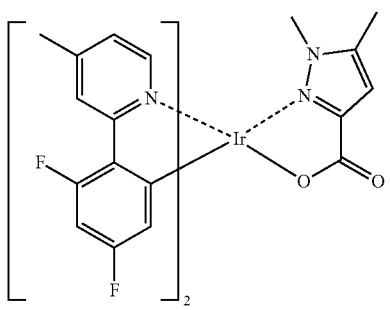
PD12
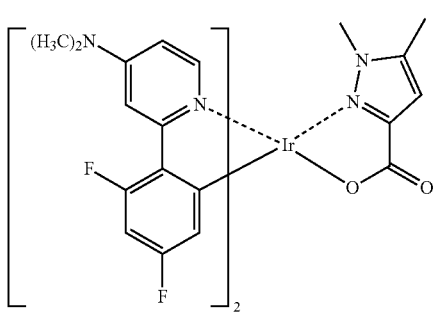
PD13
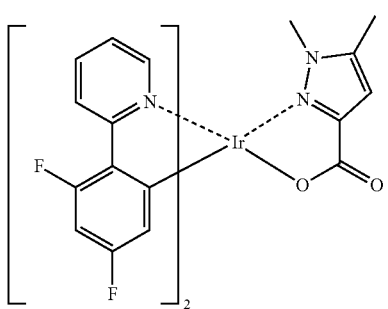
PD14
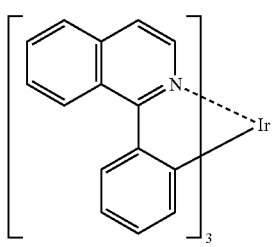
PD15
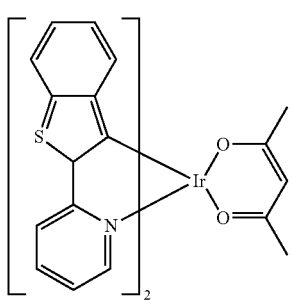
PD16
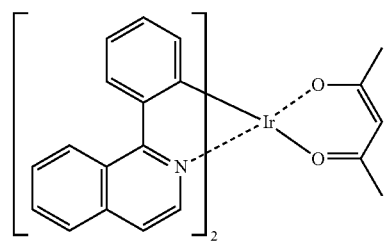
PD17
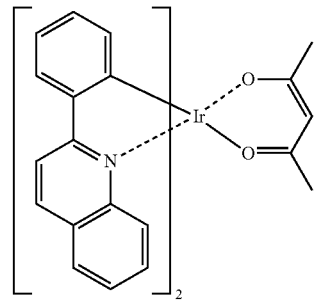
PD18
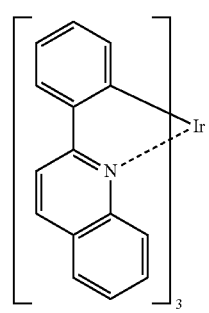
PD19
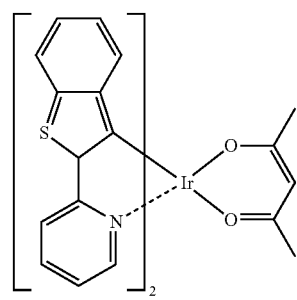
PD20
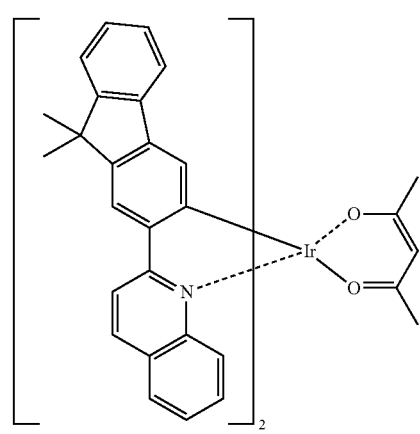

PD21
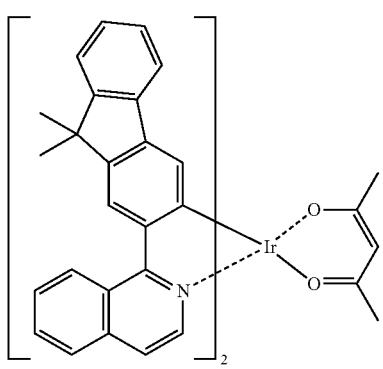
PD22
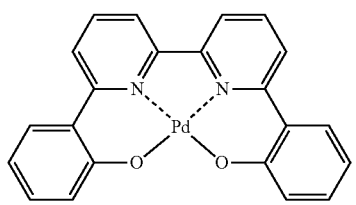
PD23
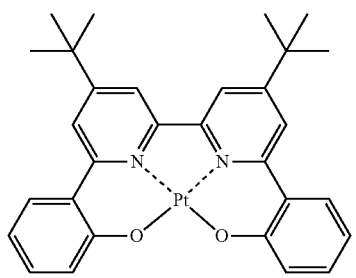
PD24
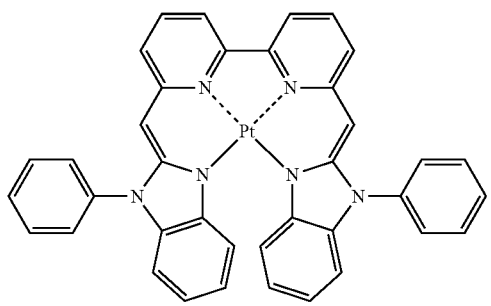
PD25
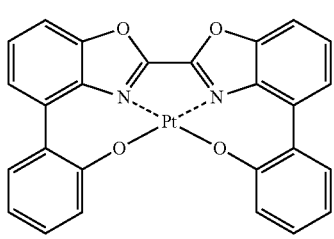
PD26
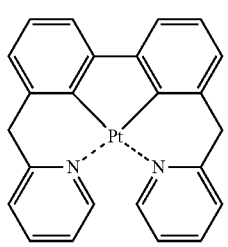
PD27
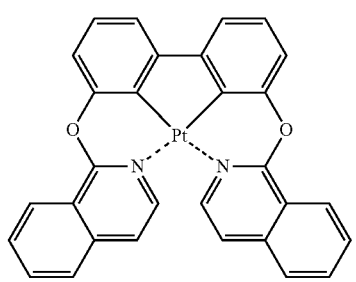
PD28
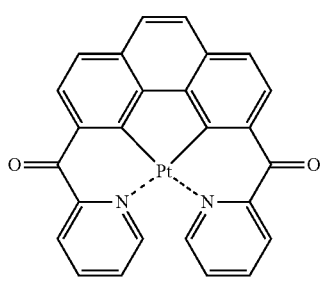
PD29
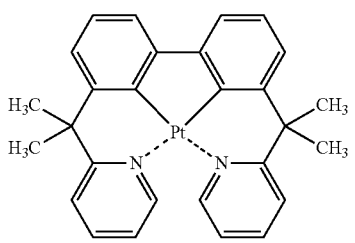
PD30
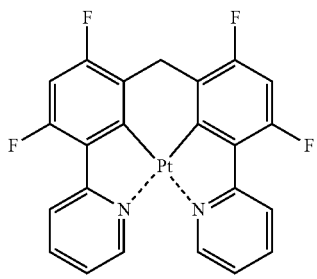
PD31
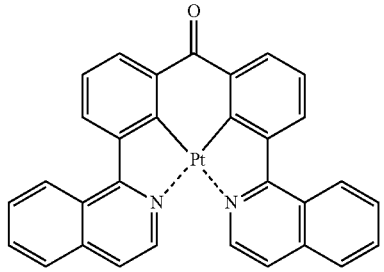
PD32
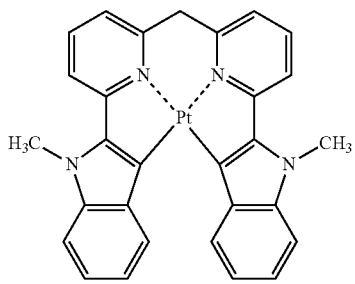

-continued
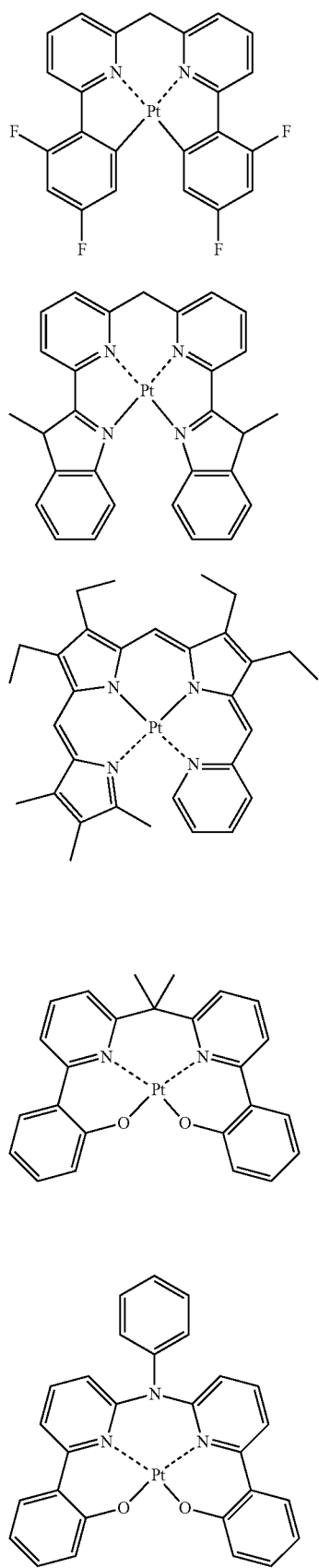
PD33
PD34
PD35
PD36
PD37
-continued
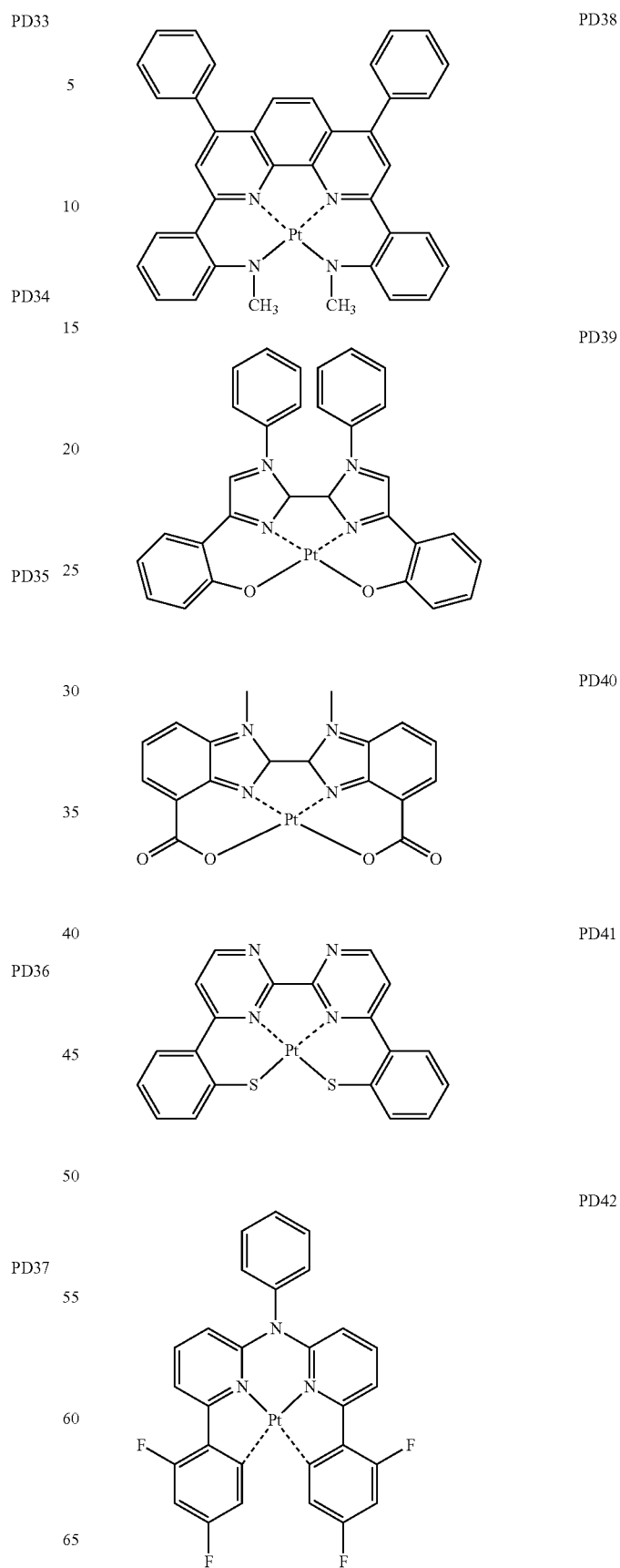
PD38
PD39
PD40
PD41
PD42

PD43
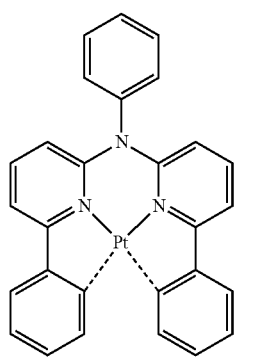
PD44
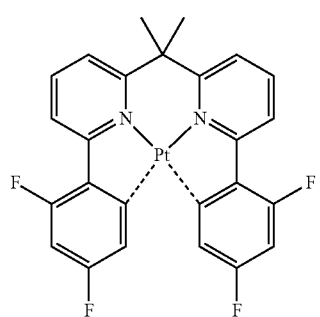
PD45
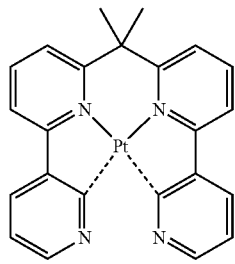
PD46
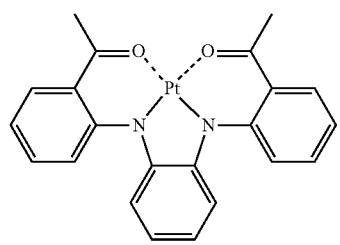
PD47
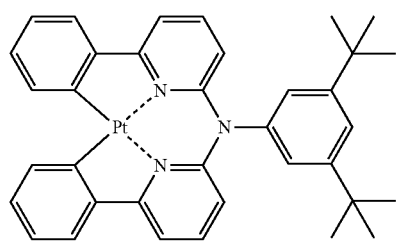
PD48
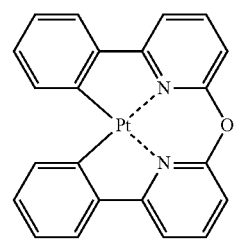
PD49
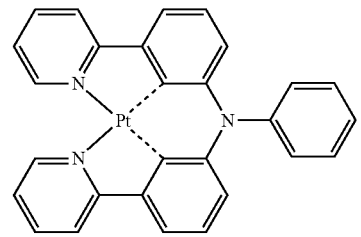
PD50
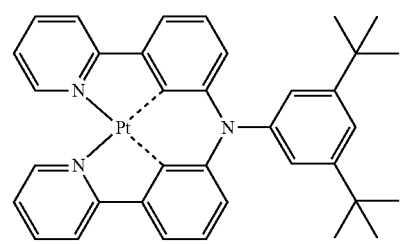
PD51
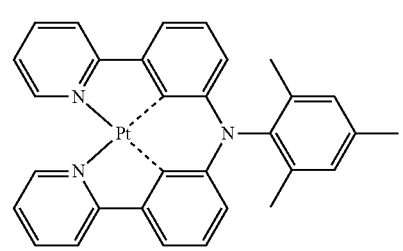
PD52
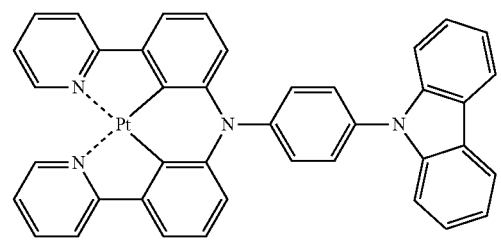
PD53
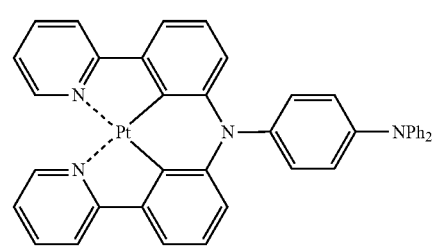

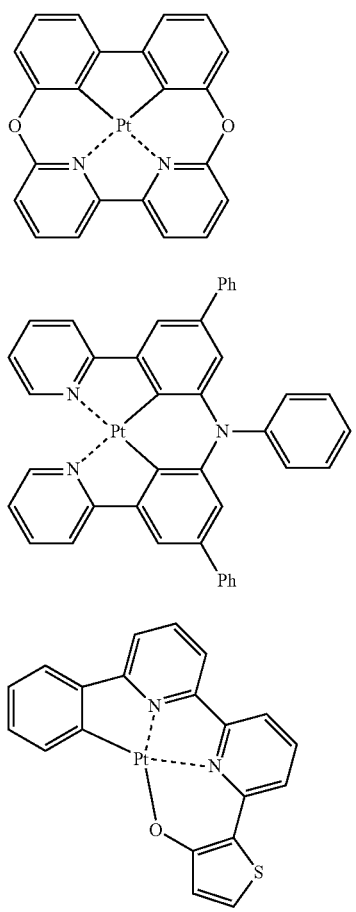
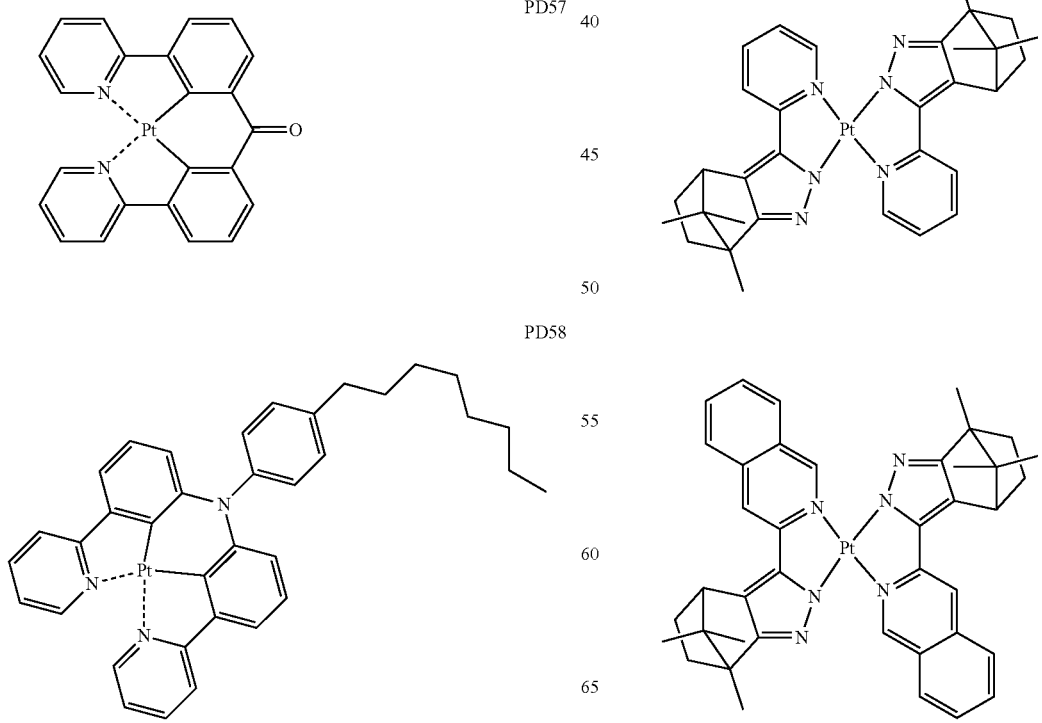

PD64 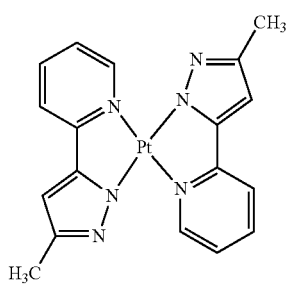
PD65 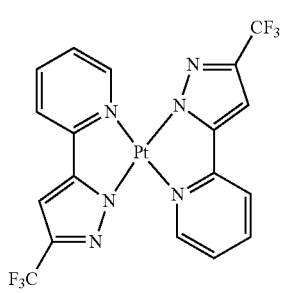
PD66 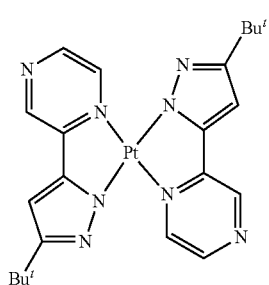
PD67 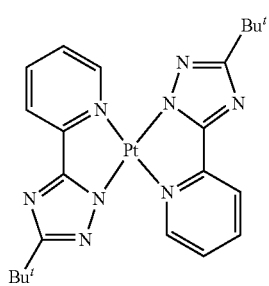
PD68 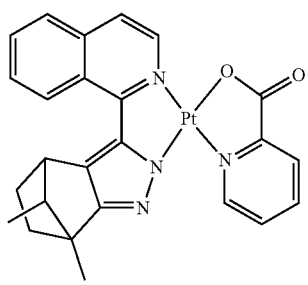
PD69 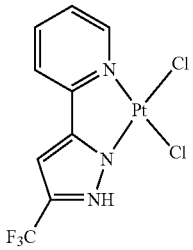
PD70 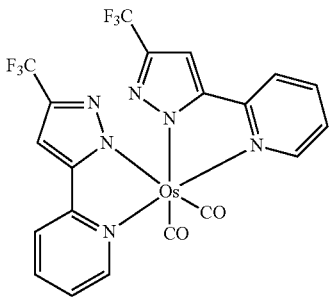
PD71 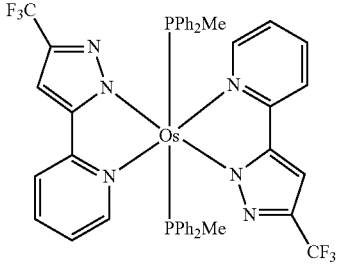
PD72 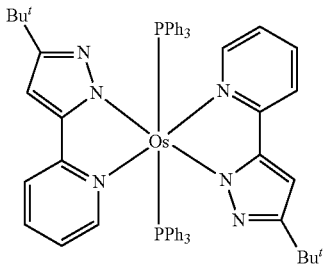
PD73 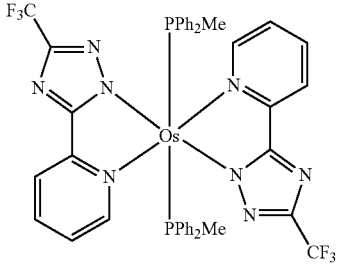

PD74 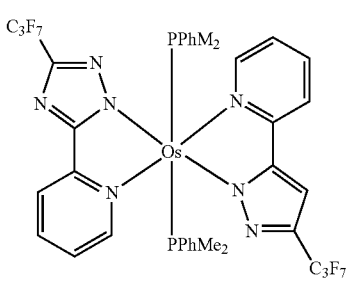

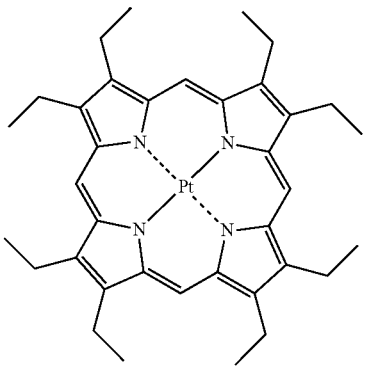

PtOEP

PD75

PD76 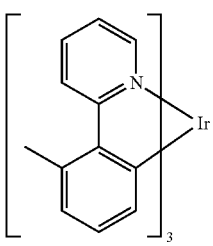

When the emission layer includes a host and a dopant, the content of the dopant may be generally about 0.01 to about 20 parts by weight based on about 100 parts by weight of the host, but is not limited thereto.

The emission layer may be about 100 Å to about 1000 Å thick, for example, about 200 Å to about 600 Å thick. When the emission layer has a thickness within the range, excellent light emitting characteristics may be obtained without substantially increasing a driving voltage.

Next, on the emission layer, an electron transport region is disposed.

The electron transport region may include at least one of a hole blocking layer, an electron transport layer (ETL) and an electron injection layer (EIL).

PD77 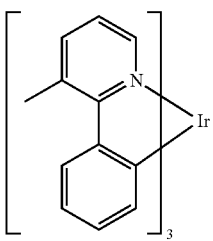

For example, the electron transport region may have a structure of hole blocking layer/electron transport layer (ETL)/electron injection layer (EIL) or electron transport layer (ETL)/electron injection layer EIL, but is not limited thereto. The electron transport layer (ETL) may have a monolayer structure or a multi-layer structure including more than two materials.

The hole blocking layer, the electron transport layer (ETL) and the electron injection layer (EIL) in the electron transport region are formed referring to the conditions for forming the hole injection layer (HIL).

When the electron transport region includes the hole blocking layer, the hole blocking layer may include, for example, at least one of the following BCP, Bphen and BAlq, but is not limited thereto.

PD78 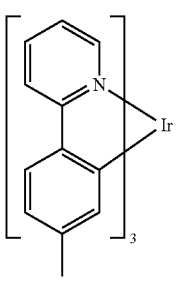

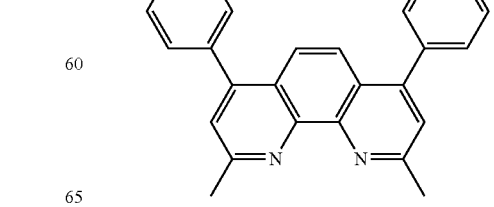

BCP

Alternatively, the phosphorescent dopant may include the following PtOEP:

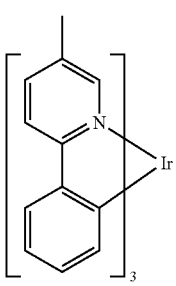

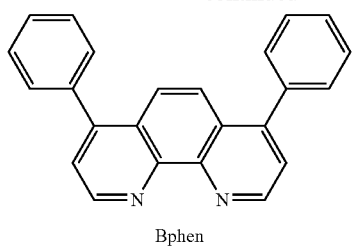

Bphen

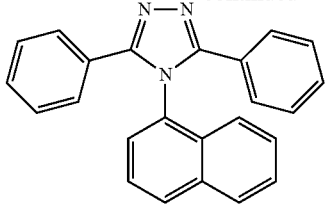

NTAZ

The hole blocking layer may be about 20 Å to about 1000 Å thick, for example about 30 Å to about 300 Å thick. When the hole blocking layer has a thickness within the range, excellent hole blocking characteristics may be obtained without substantially increasing a driving voltage.

The electron transport layer (ETL) may further include at least one of the BCP, the Bphen and the following Alq$_3$, Balq, TAZ and NTAZ.

Or, the electron transport layer (ETL) may include at least one of the following compounds ET1 and ET2, but is not limited thereto.

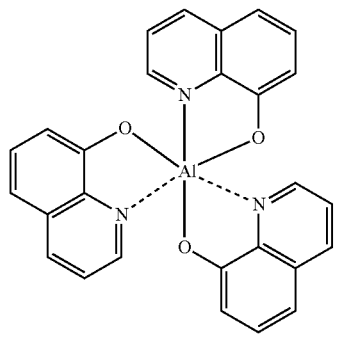

Alq$_3$

ET1

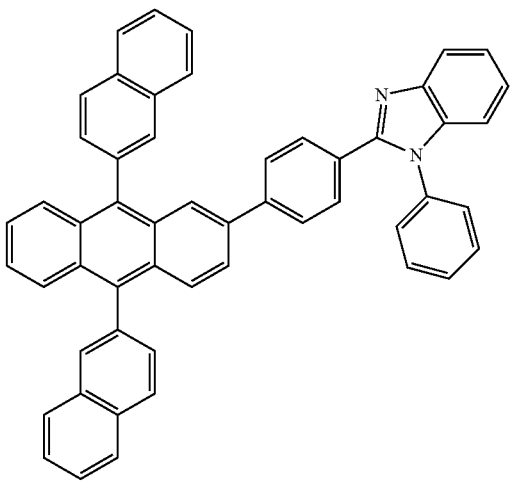

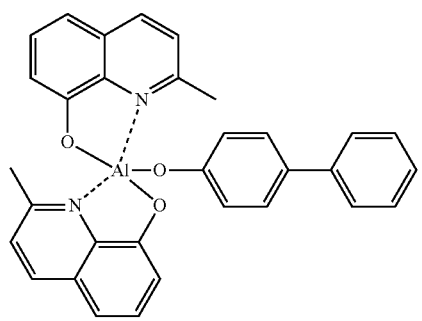

BAlq

ET2

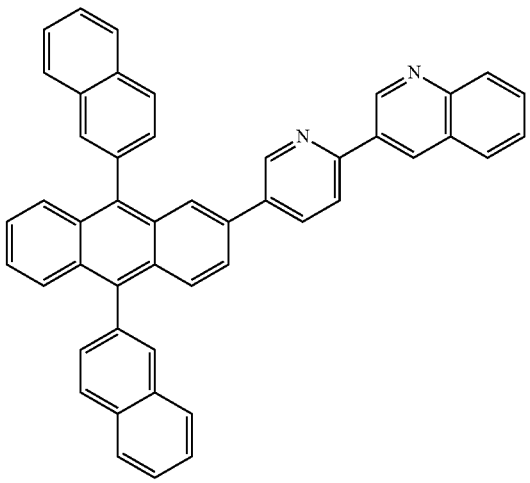

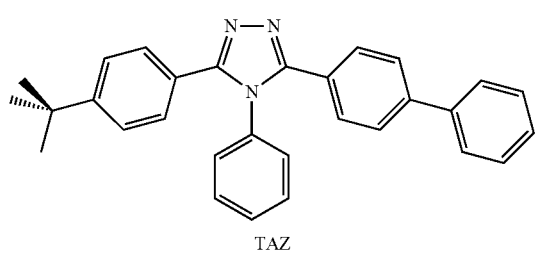

TAZ

The electron transport layer (ETL) may be about 100 Å to about 1000 Å thick, for example about 150 Å to about 500 Å thick. When the electron transport layer (ETL) has a thickness within the range, satisfactory electron transport characteristics may be obtained without substantially increasing a driving voltage.

The electron transport layer (ETL) may further include a metal-containing material other than the aforementioned material.

The metal-containing material may include a Li complex. The Li complex may include, for example, the following compound ET-D1 (lithium quinolate, LiQ) or ET-D2.

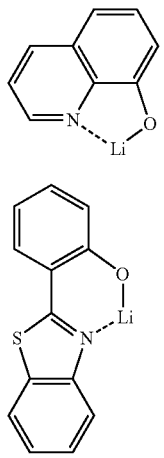

ET-D1

ET-D2

In addition, the electron transport region may include an electron injection layer (EIL) facilitating injection of electrons from the second electrode 19.

The electron injection layer (EIL) may include at least one selected from LiF, NaCl, CsF, Li$_2$O and BaO.

The electron injection layer (EIL) may be about 1 Å to about 100 Å thick and specifically, about 3 Å to about 90 Å thick. The electron injection layer (EIL) has a thickness within the range, satisfactory electron injection characteristics may be obtained without substantially increasing a driving voltage.

On the organic layer 15, the second electrode 19 is disposed. The second electrode 19 may be a cathode. A material for forming the second electrode 19 may include a metal, an alloy, electrically conductive compound and a combination thereof having a relatively low work function. Specific examples of the material for forming the second electrode 19 may include lithium (Li), magnesium (Mg), aluminum (Al), aluminum-lithium (Al—Li), calcium (Ca), magnesium-indium (Mg—In), magnesium-silver (Mg—Ag), and the like. Or, various modifications of forming the transmissive second electrode 19 by using ITO and IZO and the like may be performed to manufacture a front light emitting element.

Hereinbefore, the organic light emitting device is described referring to FIG. 1, but is not limited thereto.

In the present specification, the $C_1$-$C_{60}$ alkyl group refers to a C1 to C60 linear or branched aliphatic hydrocarbon monovalent group, and specific examples may include a methyl group, an ethyl group, a propyl group, an isobutyl group, a sec-butyl group, a ter-butyl group, a pentyl group, an iso-amyl group, a hexyl group, and the like. In the present specification, the $C_1$-$C_{60}$ alkylene group refers to a divalent group having the same structure as the $C_1$-$C_{60}$ alkyl group.

In the present specification, the $C_1$-$C_{60}$ alkoxy group is a monovalent group having Formula, —OA$_{101}$ (wherein, A$_{101}$ is the $C_1$-$C_{60}$ alkyl group), and specific examples may be a methoxy group, an ethoxy group, an isopropyloxy group, and the like.

In the present specification, the $C_2$-$C_{60}$ alkenyl group has a structure where at least one carbon double bond is included in the middle or terminal end of the $C_2$-$C_{60}$ alkyl group, and specific examples may be an ethenyl group, a propenyl group, a butenyl group, and the like. In the present specification, the $C_2$-$C_{60}$ alkenylene group refers to a divalent group having the same structure as the $C_2$-$C_{60}$ alkenyl group.

In the present specification, the $C_2$-$C_{60}$ alkynyl group has a structure where at least one carbon triple bond is included in the middle or terminal end of the $C_2$-$C_{60}$ alkyl group, and specific examples may be an ethynyl group, a propynyl group, and the like. In the present specification, the $C_2$-$C_{60}$ alkynylene group refers to a divalent group having the same structure as the $C_2$-$C_{60}$ alkynyl group.

In the present specification, the $C_3$-$C_{10}$ cycloalkyl group refers to a C3 to C10 monovalent saturated hydrocarbon monocyclic group, and examples thereof may be a cyclopropyl group, a cyclobutyl group, a cyclopentyl group, a cyclohexyl group, a cycloheptyl group, and the like. In the present specification, the $C_3$-$C_{10}$ cycloalkylene group refers to a divalent group having the same structure as the $C_3$-$C_{10}$ cycloalkyl group.

In the present specification, the $C_2$-$C_{10}$ heterocycloalkyl group refers to a C2 to C10 monovalent monocyclic group including a ring-forming atom including at least one heteroatom selected from N, O, P and S, and examples thereof are a tetrahydrofuranyl group, a tetrahydrothiophenyl group, and the like. In the present specification, the $C_2$-$C_{10}$ heterocycloalkylene group refers to a divalent group having the same structure as the $C_2$-$C_{10}$ heterocycloalkyl group.

In the present specification, the $C_3$-$C_{10}$ cycloalkenyl group refers to a C3 to C10 monovalent monocyclic group having at least one double bond in the ring and not having aromacity, and examples thereof are a cyclopentenyl group, a cyclohexenyl group, a cycloheptenyl group, and the like. In the present specification, the $C_3$-$C_{10}$ cycloalkenylene group refers to a divalent group having the same structure as the $C_3$-$C_{10}$ cycloalkenyl group.

In the present specification, the $C_2$-$C_{10}$ heterocycloalkenyl group refers to a C2 to C10 monovalent monocyclic group including a ring-forming atom including at least one heteroatom selected from N, O, P and S, and includes at least one double bond in the ring. Examples of the $C_2$-$C_{10}$ heterocycloalkenyl group are a 2,3-hydrofuranyl group, a 2,3-hydrothiophenyl group, and the like. In the present specification, the $C_2$-$C_{10}$ heterocycloalkenylene group refers to a divalent group having the same structure as the $C_2$-$C_{10}$ heterocycloalkenyl group.

In the present specification, the $C_6$-$C_{60}$ aryl group refers to a monovalent group having a C6 to C60 carbocyclic aromatic system, and $C_6$-$C_{60}$ arylene group refers to a divalent group having a C6 to C60 carbocyclic aromatic system. Examples of the $C_6$-$C_{60}$ aryl group are a phenyl group, a naphthyl group, an anthracenyl group, a phenanthrenyl group, a pyrenyl group, a chrysenyl group, and the like. When the $C_6$-$C_{60}$ aryl group and $C_6$-$C_{60}$ arylene group includes 2 or more rings, the 2 or more rings may be fused.

In the present specification, the $C_2$-$C_{60}$ heteroaryl group refers to a monovalent group including a ring-forming atom including at least one heteroatom selected from N, O, P and S, and having a C2 to C60 carbocyclic aromatic system, and the $C_2$-$C_{60}$ heteroarylene group refers to a divalent group including a ring-forming atom including at least one heteroatom selected from N, O, P and S and having a C2 to C60 carbocyclic aromatic system. Examples of the $C_2$-$C_{60}$ heteroaryl group are a pyridinyl group, a pyrimidinyl group, a pyrazinyl group, a pyridazinyl group, a triazinyl group, a quinolinyl group, an isoquinolinyl group, and the like. When the $C_2$-$C_{60}$ heteroaryl group and $C_2$-$C_{60}$ heteroarylene group include 2 or more rings, the 2 or more rings may be fused.

In the present specification, the $C_6$-$C_{60}$ aryloxy group refers to —$OA_{102}$ (wherein, $A_{102}$ is the $C_6$-$C_{60}$ aryl group), and the $C_6$-$C_{60}$ arylthio group refers to —$SA_{103}$ (wherein, $A_{103}$ is the $C_6$-$C_{60}$ aryl group).

In the present specification, the monovalent non-aromatic condensed polycyclic group refers to a monovalent group including condensation of 2 or more rings, and including only carbon as ring-forming atoms (e.g., carbon numbers are 8 to 60), and having non-aromaticity over the entire molecule. Examples of the non-aromatic condensed polycyclic group are a fluorenyl group, and the like. In the present specification, the divalent non-aromatic condensed polycyclic group refers to a divalent group having the same structure as the monovalent non-aromatic condensed polycyclic group.

In the present specification, the monovalent non-aromatic heterocondensed polycyclic group refers to a monovalent group including condensation of 2 or more rings, and including hetero atoms selected from N, O, P and S as well as carbon (e.g., carbon numbers are 2 to 60) as ring-forming atoms, and having non-aromaticity over the entire molecule. The monovalent non-aromatic heterocondensed polycyclic group includes a carbazolyl group, and the like. In the present specification, the divalent non-aromatic heterocondensed polycyclic group refers to a divalent group having the same structure as the monovalent non-aromatic heterocondensed polycyclic group.

In the present specification, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group and substituted monovalent non-aromatic heterocondensed polycyclic group may be selected from, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and a $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ a cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, monovalent non-aromatic heterocondensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group and a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —$N(Q_{21})(Q_{22})$, —$Si(Q_{23})(Q_{24})(Q_{25})$ and —$B(Q_{26})(Q_{27})$; and —$N(Q_{31})(Q_{32})$, —$Si(Q_{33})(Q_{34})(Q_{35})$ and —$B(Q_{36})(Q_{37})$.

In the present specification, $Q_1$ to $Q_7$, $Q_{11}$ to $Q_{17}$ and $Q_{31}$ to $Q_{37}$ may be independently selected from hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group and a monovalent non-aromatic heterocondensed polycyclic group.

For example, at least one substituent of the substituted $C_1$-$C_{60}$ alkylene group, the substituted $C_2$-$C_{60}$ alkenylene group, the substituted $C_2$-$C_{60}$ alkynylene group, the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group and substituted monovalent non-aromatic heterocondensed polycyclic group may be selected from, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and $C_1$-$C_{60}$ alkoxy group;

a $C_1$-$C_{60}$ alkyl group, a $C_2$-$C_{60}$ alkenyl group, a $C_2$-$C_{60}$ alkynyl group and a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ a cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{11}$)($Q_{12}$), —Si($Q_{13}$)($Q_{14}$)($Q_{15}$), and —B($Q_{16}$)($Q_{17}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, pyrrolyl group, an imidazolyl group, a pyrazolyl group, a yridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group and an imidazopyridinyl group each of which is substituted with at least one of a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group and a quinazolinyl group;

deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group and $C_1$-$C_{60}$ alkoxy group;

a $C_1$-$C_{60}$ alkyl group, a $C_2$-$C_{60}$ alkenyl group, a $C_2$-$C_{60}$ alkynyl group and $C_1$-$C_{60}$ alkoxy group each of which is substituted with at least one of a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{21}$)($Q_{22}$), —Si($Q_{23}$)($Q_{24}$)($Q_{25}$) and —B($Q_{26}$)($Q_{27}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group and an imidazopyridinyl group each of which is substituted with at least one of a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a Cinnolinyl group and a quinazolinyl group; and —N($Q_{31}$)($Q_{32}$), —Si($Q_{33}$)($Q_{34}$)($Q_{35}$) and —B($Q_{36}$)($Q_{37}$);

wherein the $Q_1$ to $Q_7$, $Q_{11}$ to $Q_{17}$ and $Q_{31}$ to $Q_{37}$ are independently a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzooxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group and an imidazopyridinyl group each of which is substituted with at least one of hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a Cinnolinyl group and a quinazolinyl group, but are not limited thereto.

In the present specification, the "biphenyl group" refers to "a phenyl group substituted with a phenyl group."

Hereinafter, a compound and an organic light emitting device according to one embodiment of the present invention are specifically illustrated referring to Synthesis Examples and Examples, but the present invention is not limited to the following Synthesis Examples and Examples. In the following Synthesis Examples, when "'B' is used instead of 'A'", the amounts of 'A' and 'B' are the same as based on a mole equivalent.

EXAMPLE

Synthesis Example 1: Synthesis of Compound 1

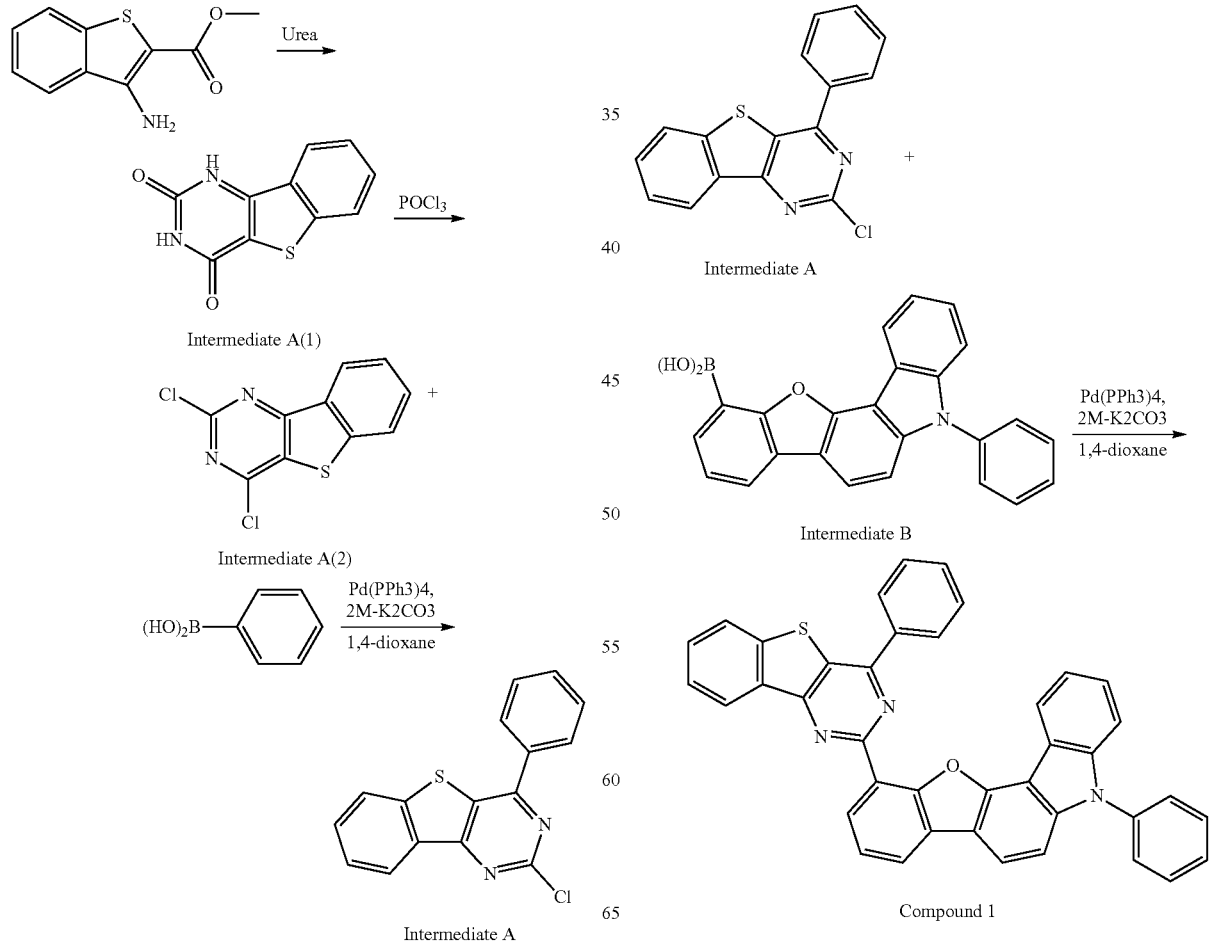

Synthesis of Intermediate A(1) (benzo-1H-thieno[3,2-d]pyrimidine-2,4-dione)

A mixture of benzo-methyl 3-amino-2-thiophenecarboxylate (47.5 g, 0.23 mol) and urea (79.4 g, 1.15 mol) was agitated at 200° C. for 2 hours in a 2000 mL round flask. The reaction mixture at the high temperature was cooled down to room temperature and poured into a sodium hydroxide solution, the reactant obtained by filtering and removing an impurity therein was acidized (HCl, 2N) to obtain a precipitate, and the precipitate was dried, obtaining an intermediate A(1) (35 g, 75%).

Synthesis of Intermediate A(2) (benzo-2,4-dichloro-thieno[3,2-d]pyrimidine)

A mixture of the intermediate A (1) (benzo-1H-thieno[3,2-d]pyrimidine-2,4-dione) (35 g, 0.16 mol) and 600 mL of phosphorus oxychloride was agitated under a reflux for 6 hours in a 1000 mL round flask. The reaction mixture was cooled down to room temperature, and ice/water was poured thereinto to produce a precipitate while the reaction mixture was agitated. The obtained reactant was filtered, obtaining an intermediate A (2) (benzo-2,4-dichloro-thieno[3,2-d]pyrimidine) (35 g, 85%, a white solid).

Synthesis of Intermediate A 20.0 g (78.4 mmol) of the intermediate A(2), 11.0 g (90.15 mmol) of phenylboronic acid, 27.09 g (195.99 mmol) of potassium carbonate, and 4.53 g (3.9 mmol) of Pd(PPh$_3$)$_4$ (tetrakis-(triphenylphosphine) palladium (0)) were added to 300 mL of 1,4-dioxane and 150 mL of water in a 1000 mL flask and then, heated at 60° C. for 12 hours under a nitrogen atmosphere. The obtained mixture was added to 1000 mL of methanol, and a solid crystallized therein, dissolved in monochlorobenzene, filtered with silica gel/Celite, and then, recrystallized with methanol after removing an organic solvent in an appropriate amount, obtaining an intermediate A (13.9 g, a yield of 60%).

Synthesis of Intermediate B(1)

5H-benzofuro[3,2-c]carbazole (40 g, 155.47 mmol), bromobenzene (293.3 g, 186.56 mmol), trisdibenzylideneacetonedipaladium (4.27 g, 4.66 mmol) and sodium-t-butoxide (19.4 g, 202.11 mmol) were put in a 1 L flask, 750 ml of xylene was added thereto, and the mixture was agitated. Then, tri-t-butylphosphine (3.4 ml, a 50% solution (toluene)) was added thereto, and the mixture was heated at 130° C. for 12 hours under a nitrogen atmosphere. The obtained reactant was cooled down to room temperature and then, poured into 1 L of methanol, and a solid produced therein was filtered and recrystallized with dichloromethane and methanol, obtaining an intermediate B(1) (25 g, 48%).

Synthesis of Intermediate B

The intermediate B(1) (25 g, 74.99 mmol) was dissolved in 250 ml of tetrahydrofuran in a reactor, the reactor was cooled down by using liquid nitrogen, n-butyllithium (35.99 ml, 89.99 mmol) was added thereto in a dropwise fashion, the mixture was agitated for 6 hours at room temperature, and then, the reactor was cooled down. Next, trimethylborate (10.03 ml, 89.99 mol) was slowly added thereto in a dropwise fashion, a reactant obtained by agitating the mixture for 8 hours was poured into 900 ml of a 1N—HCl aqueous solution, and the mixture was agitated and extracted with dichloromethane and then, recrystallized with dichloromethane and hexane, obtaining an intermediate B (20 g, 71%).

Synthesis of Compound 1

The intermediate A (13 g, 43.80 mmol), the intermediate B (16.52 g, 43.80 mmol), potassium carbonate (12.1 g, 87.61 mmol) and tetrakistriphenylphosphine (2.53 g, 2.19 mmol) were put in a 500 ml flask, 40 ml of water and 175 ml of 1,4-dioxane were added thereto, and the mixture was heated at 100° C. for 12 hours. The obtained reactant was poured into 500 ml of methanol, and a solid produced therein was filtered and recrystallized with 1,2-dichlorobenzene, obtaining a compound 1 (20 g, 77%).

300 MHz (CDCl$_3$, ppm): 7.27-7.31 (m, 1H), 7.42-7.79 (m, 14H), 8.00-8.03 (m, 2H), 8.14-8.17 (d, 1H), 8.61-8.64 (m, 2H), 8.69-8.74 (t, 2H), 8.97-8.99 (d, 1H)

Synthesis Example 2: Synthesis of Compound 4

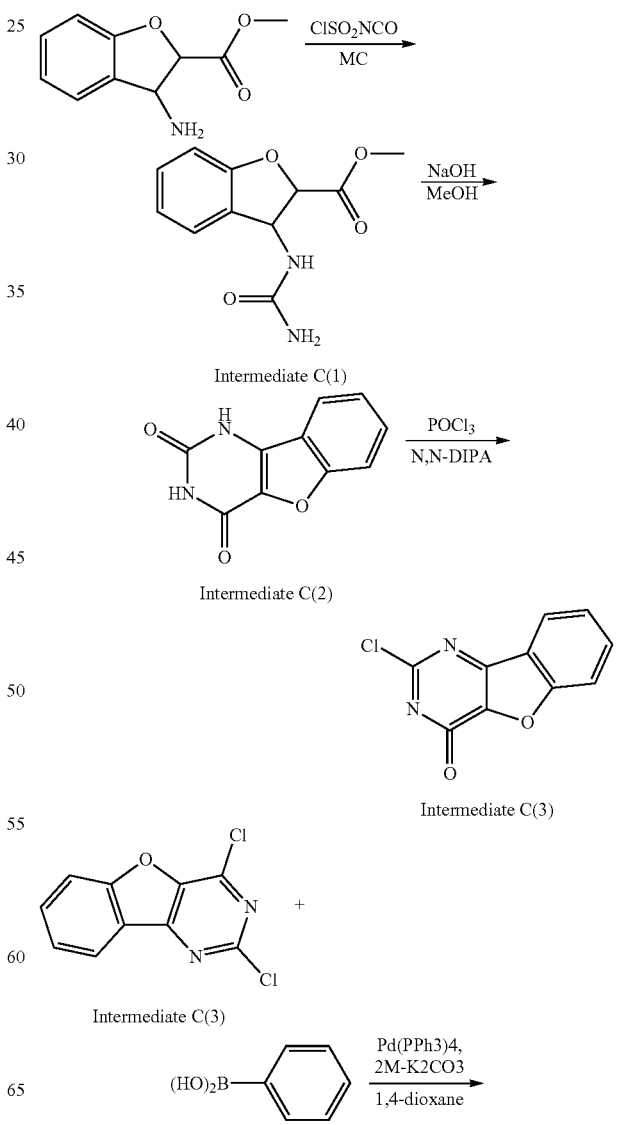

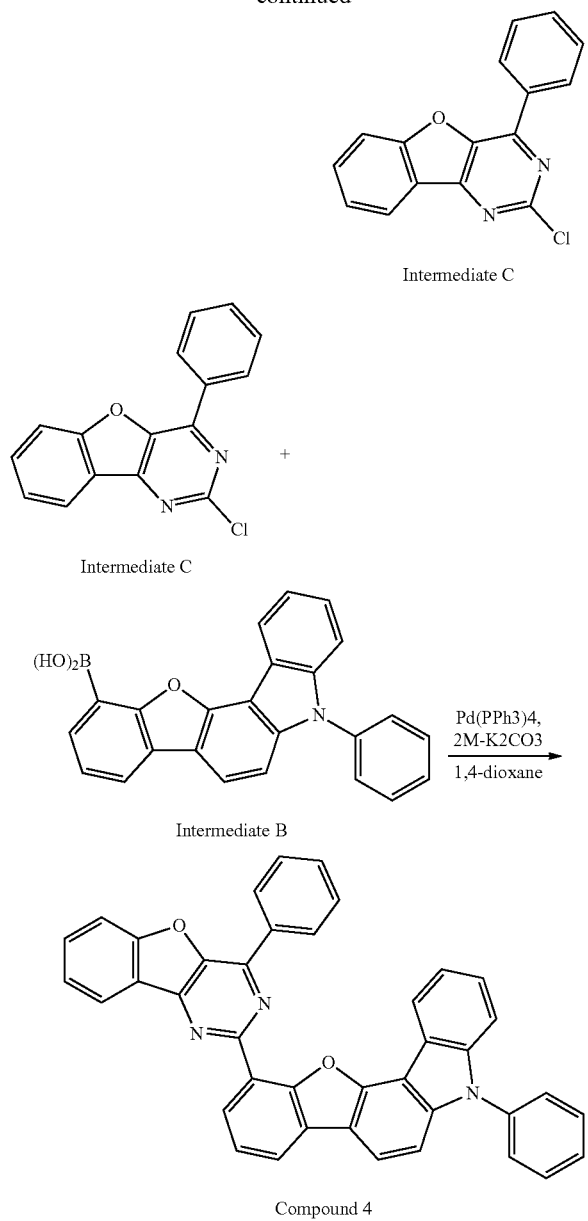

Synthesis of Intermediate C(1) (benzo-methyl 3-ureidofuran-2-carboxylate)

Chlorosulfonyl isocyanate (33.4 ml, 0.38 mol) was added in a dropwise fashion to a benzo-methyl 3-aminofuran-2-carboxylate (49.0 g, 0.25 mol) solution in dichloromethane (1000 ml) in a 1000 mL round flask at −78° C. The reactant was slowly heated up to room temperature and agitated for 2 hours. Then, the reactant was concentrated, Conc. HCl (100 ml) was added thereto, and the mixture was agitated at 100° C. for 1 hour. The reaction mixture was cooled down to room temperature and neutralized with a saturated NaHCO$_3$ aqueous solution. Then, a solid produced therein was filtered, obtaining an intermediate C (1, benzo-ethyl 3-ureidofuran-2-carboxylate) (52.1 g, 87%) as a beige solid.

Synthesis of Intermediate C(2) (benzo-furo[3,2-d]pyrimidine-2,4-diol)

The intermediate C (1) (benzo-ethyl 3-ureidofuran-2-carboxylate) (50.0 g, 0.21 mol) was suspended in 1000 ml of methanol in a 2000 mL round flask, and 300 ml of 2 M NaOH was added thereto in a dropwise fashion. The reaction mixture was agitated under a reflux for 3 hours. Then, the reaction mixture was cooled down to room temperature and acidized into pH 3 by using Conc. HCl. After concentrating the mixture, methanol was slowly added to the residue in a dropwise fashion, precipitating a solid. The solid was filtered and then, dried, obtaining an intermediate C (2, benzo-furo[3,2-d]pyrimidine-2,4-diol) (38.0 g, 88%).

Synthesis of Intermediate C(3) (benzo-2,4-dichloro-furo[3,2-d]pyrimidine)

The intermediate C (2, benzo-furo[3,2-d]pyrimidine-2,4-diol) (37.2 g, 0.18 mol) was dissolved in phosphorous oxychloride (500 ml) in a 1000 mL round flask. The mixture was cooled down to −30° C., and N,N-diisopropylethylamine (52 ml, 0.36 mol) was slowly added thereto. The reactant was agitated under a reflux for 36 hours and then, cooled down to room temperature. Then, ice/water was poured into the reactant, and extraction was performed by using ethyl acetate. The obtained organic layer was washed with a saturated NaHCO3 aqueous solution and dried by using Na$_2$SO$_4$. Then, the organic layer was concentrated, obtaining an intermediate C (3, benzo-2,4-dichlorofuro[3,2-d]pyrimidine) (20.4 g, 46%).

Synthesis of Intermediate C 40.0 g (167.3 mmol) of the intermediate C(3), 22.4 g (184.1 mmol) of phenylboronic acid, 57.8 g (418.3 mmol) of potassium carbonate, and 9.7 g (8.4 mmol) of Pd(PPh$_3$)$_4$ (tetrakis(triphenylphosphine)palladium (0)) were added to 500 mL of 1,4-dioxane and 250 mL of water in a 2000 mL flask, and the mixture was heated at 40° C. for 8 hours under a nitrogen atmosphere. The obtained mixture was added to 1500 mL of methanol, and a solid crystallized therein, dissolved in monochlorobenzene, filtered with silica gel/Celite, and then, recrystallized with methanol after removing an organic solvent in an appropriate amount, obtaining an intermediate C (31.0 g, a yield of 66%).

Synthesis of Compound 4

A compound 4 (21 g, 68%) was synthesized according to the same method as Synthesis Example 1 except for using the intermediate C (15 g, 53.44 mmol), the intermediate B (20.16 g, 53.44 mmol), potassium carbonate (14.7 g, 106.8 mmol) and tetrakistriphenylphosphine (3.09 g, 2.67 mmol) instead of the intermediate A (13 g, 43.80 mmol), the intermediate B (16.52 g, 43.80 mmol), potassium carbonate (12.1 g, 87.61 mmol) and tetrakistriphenylphosphine (2.53 g, 2.19 mmol).

300 MHz (CDCl$_3$, ppm): 7.26-7.32 (m, 1H), 7.41-7.82 (m, 15H), 7.98-8.04 (d, 1H), 8.10-8.15 (d, 1H), 8.53-8.55 (d, 1H), 8.61-8.64 (d, 1H), 8.71-8.75 (d, 1H), 9.00-9.05 (d, 2H)

Synthesis Example 3: Synthesis of Compound 25

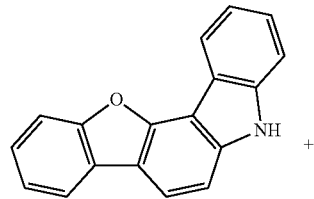

5H-benzofuro[3,2-c]carbazole

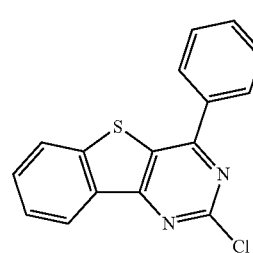

Intermediate A

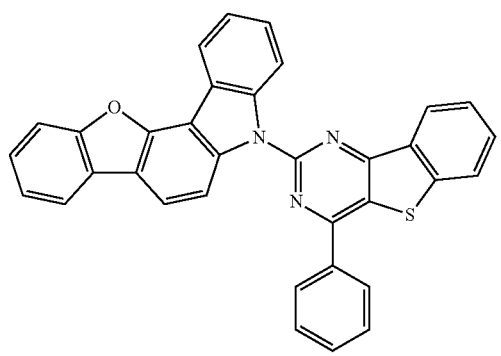

Compound 25

A compound 25 (21 g, 75%) was synthesized according to the same method as Synthesis Example 1 except for using 5H-benzofurano[3,2-c]carbazole (14 g, 54.41 mmol) and the intermediate A (19.38 g, 65.30 mmol) instead of the 5H-benzofuro[3,2-c]carbazole (40 g, 155.47 mmol) and the bromobenzene (293.3 g, 186.56 mmol).

calcd. $C_{34}H_{19}N_3OS$: C, 78.90; H, 3.70; N, 8.12; O, 3.09; S, 6.19. found: C, 78.84; H, 3.71; N, 8.15.

Synthesis Example 4: Synthesis of Compound 26

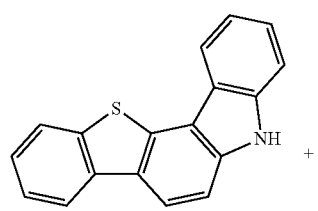

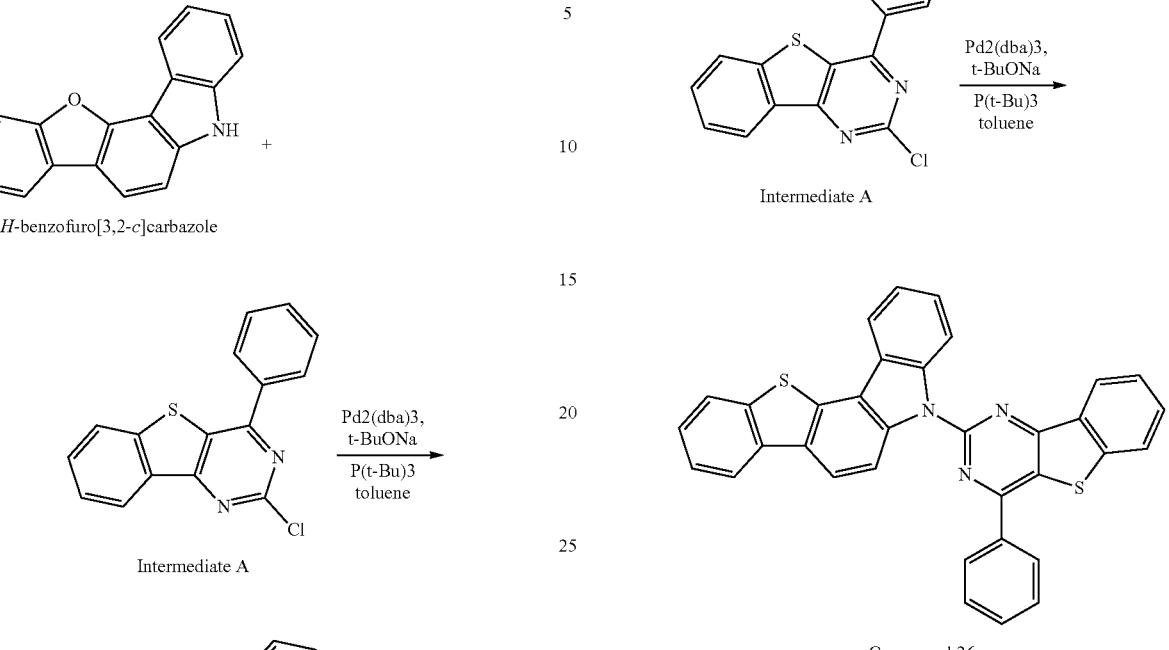

Intermediate A

Compound 26

A compound 26 (22 g, 76%) was synthesized according to the same method as Synthesis Example 1 except for using 5H-benzothiazo[3,2-c]carbazole (15 g, 54.48 mmol), the intermediate C (19.40 g, 65.37 mmol) instead of the 5H-benzofuro[3,2-c]carbazole (40 g, 155.47 mmol) and bromobenzene (293.3 g, 186.56 mmol).

calcd. $C_{34}H_{19}N_3S_2$: C, 76.52; H, 3.59; N, 7.87; S, 12.02. found: C, 76.54; H, 3.60; N, 7.88.

Synthesis Example 5: Synthesis of Compound 27

Intermediate F(1)

-continued

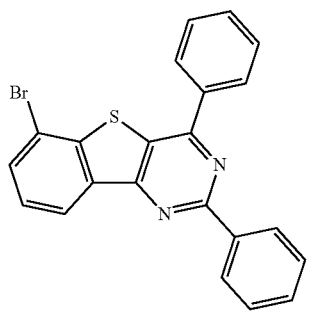

Intermediate F

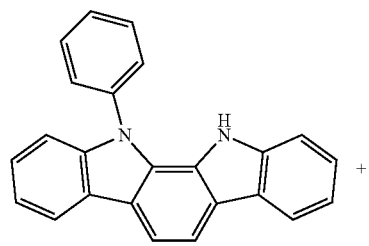

+

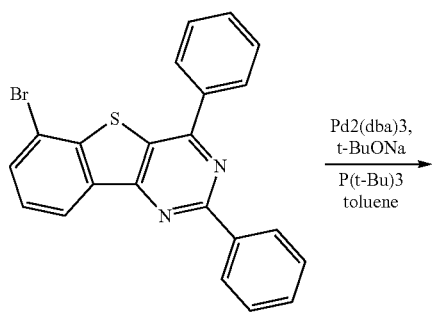

Intermediate F

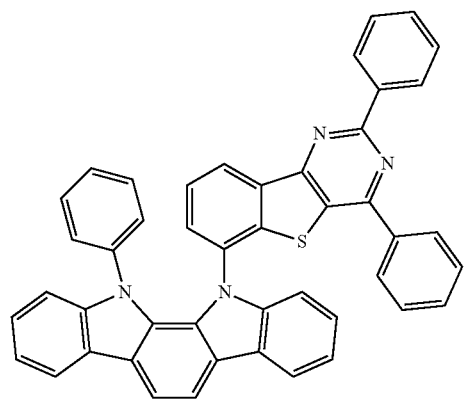

Compound 27

Synthesis of Intermediate F(1)

7-bromobenzo[b]thiophene-3(2H)-on (18.1 g, 78.81 mmol) and benzaldehyde (5.1 g, 78.81 mmol) were put in a 500 ml flask, sodium hydroxide (4.729 g, 118.22 mmol) was added thereto, 160 ml of ethanol was poured thereinto, and the mixture was agitated at room temperature for 12 hours. The obtained solid was filtered and washed with ethanol, obtaining an intermediate F(1) (12 g, 48%).

Synthesis of Intermediate F

The intermediate F(1) (7.6 g, 23.96 mmol), benzamidine hydrochloride (2.3 g, 23.93 mmol), and sodium hydroxide (2.875 g, 71.89 mmol) were added to 100 ml of ethanol, and the mixture was agitated at room temperature for 12 hours. The obtained solid was filtered and purified through column chromatography by using dichloromethane and hexane as a solvent, obtaining an intermediate F (5.3 g, 53%).

Synthesis of Compound 27

A compound 27 (3.5 g, 58%) was synthesized according to the same method as Synthesis Example 1 except for using 11,12-dihydro-11-phenylindolo[2,3-a]carbazole (3 g, 9.03 mmol) and the intermediate F (4.52 g, 10.83 mmol) instead of the 5H-benzofuro[3,2-c]carbazole (40 g, 155.47 mmol) and the bromobenzene (293.3 g, 186.56 mmol).

calcd. $C_{46}H_{28}N_4S$: C, 82.61; H, 4.22; N, 8.38; S, 4.79. found: C, 82.60; H, 4.25; N, 8.39.

Example 1

A glass substrate having a 1500 Å-thick ITO (Indium tin oxide) electrode (a first electrode, an anode) was cleaned with a distilled water ultrasonic wave. Then, the substrate was ultrasonic wave-cleaned with a solvent such as isopropyl alcohol, acetone, methanol and the like and dried, then, moved to a plasma cleaner and cleaned by using an oxygen plasma for 5 minutes, and then, moved to a vacuum depositor.

Then, a 1200 Å-thick hole transport layer (HTL) was formed on the ITO electrode of the glass substrate by vacuum-depositing a compound HTS, forming a hole transport region.

On the hole transport region, a 400 Å-thick emission layer was formed by codepositing the compound 1 (a host) and PhGD (a dopant (the same as a compound PD75) 10 wt %).

On the emission layer, a 50 Å-thick first electron transport layer (ETL) was formed by vacuum-depositing BAlq, a 250 Å-thick second electron transport layer (ETL) was formed on the first electron transport layer (ETL) by vacuum-depositing Alq₃, a 5 Å-thick electron injection layer (EIL) was formed on the second electron transport layer (ETL) by depositing LiF, and a 1000 Å-thick Al second electrode (a cathode) was formed on the electron injection layer (EIL), manufacturing an organic light emitting device.

HT5

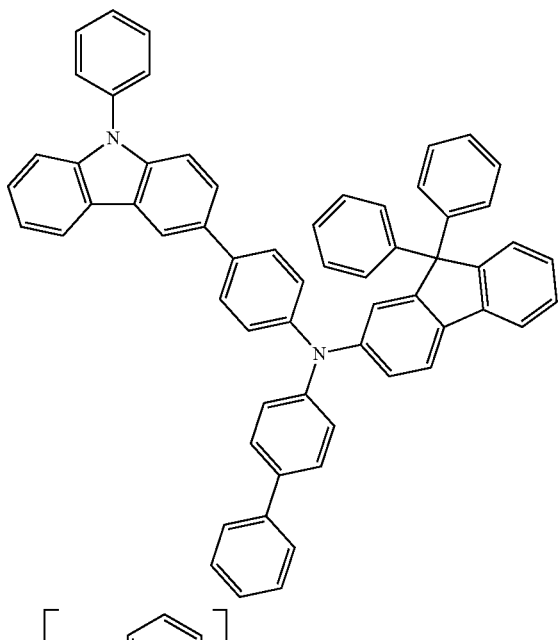

PhGD

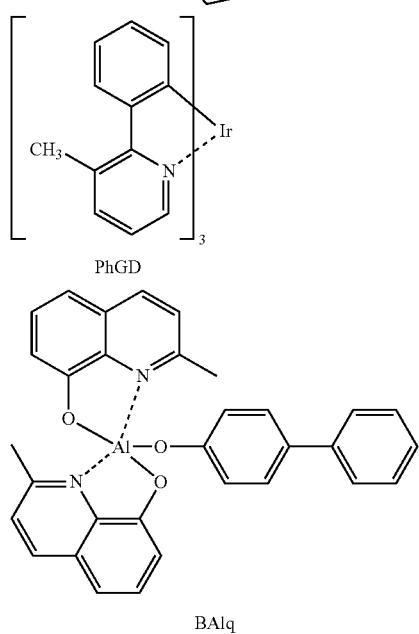

BAlq

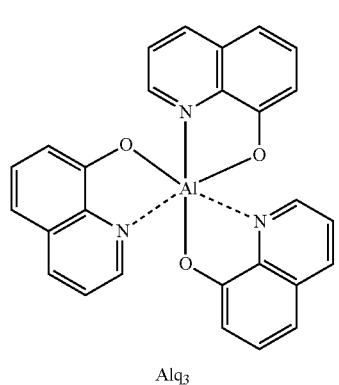

Alq₃

Example 2

An organic light emitting device was manufactured according to the same method as Example 1 except for using the compound 4 instead of the compound 1 as a host to form an emission layer.

Example 3

An organic light emitting device was manufactured according to the same method as Example 1 except for using the compound 25 instead of the compound 1 as a host to form an emission layer.

Example 4

An organic light emitting device was manufactured according to the same method as Example 1 except for using the compound 26 instead of the compound 1 as a host to form an emission layer.

Example 5

An organic light emitting device was manufactured according to the same method as Example 1 except for using the compound 27 instead of the compound 1 as a host to form an emission layer.

Evaluation Example 1: Characteristics of Organic Light Emitting Diode

Current density and luminance changes depending on a voltage and luminous efficiency of each organic light emitting device according to Examples 1 to 5 were measured. The measurements were specifically performed in the following method, and the results were provided in the following Table 2.

(1) Measurement of Current Density Change Depending on Voltage Change

The obtained organic light emitting devices were measured for current value flowing in the unit device while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting devices was increased from 0 V to 10 V.

(3) Measurement of Luminous Efficiency

Current efficiency (cd/A) at the same current density (10 mA/cm²) were calculated by using the luminance, current density, and voltages (V) from the items (1) and (2).

TABLE 2

| | Host | Dopant | Driving Voltage (V) | Efficiency (cd/A) | Color coordinate CIE x | Color coordinate CIE y |
|---|---|---|---|---|---|---|
| Example 1 | Compound 1 | PhGD | 4.1 | 56.3 | 0.366 | 0.601 |
| Example 2 | Compound 4 | PhGD | 4.4 | 53.7 | 0.379 | 0.591 |
| Example 3 | Compound 25 | PhGD | 4.2 | 54.0 | 0.380 | 0.592 |
| Example 4 | Compound 26 | PhGD | 4.2 | 55.2 | 0.376 | 0.595 |
| Example 5 | Compound 27 | PhGD | 4.4 | 52.5 | 0.375 | 0.594 |
| Comparative Example 1 | CBP | PhGD | 7.8 | 44.6 | 0.33 | 0.62 |

Referring to Table 2, the organic light emitting devices according to Examples 1 to 5 showed remarkably improved luminous efficiency compared with Comparative Example 1.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

10: organic light emitting device
11: first electrode
15: organic layer
19: second electrode

The invention claimed is:
1. A condensed cyclic compound represented by the following Formula 1:

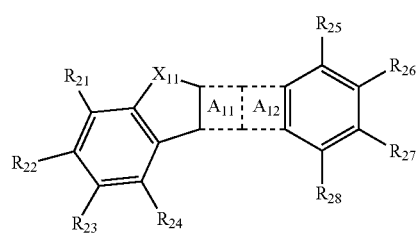

<Formula 1>

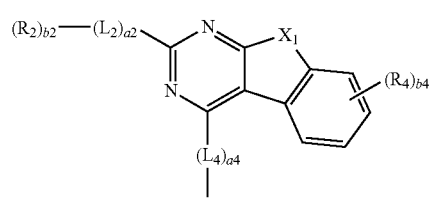

<Formula 2A>

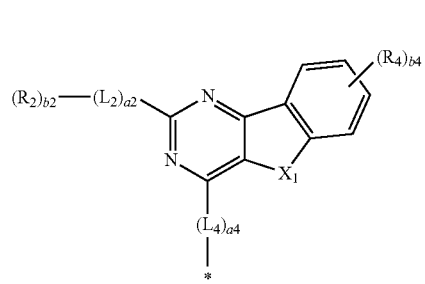

<Formula 2B>

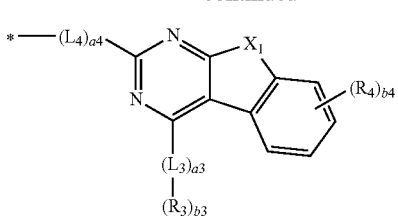

<Formula 2C>

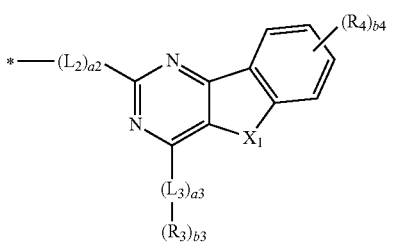

<Formula 2D>

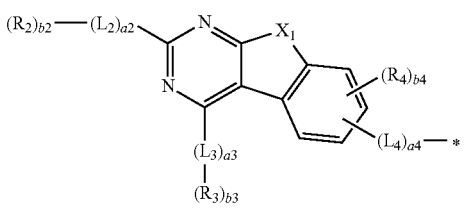

<Formula 2E>

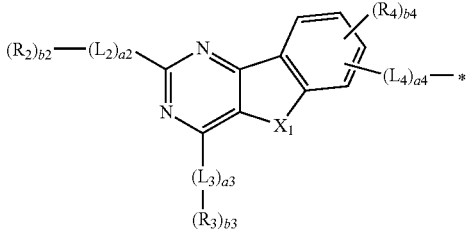

<Formula 2F>

<Formula 1A>

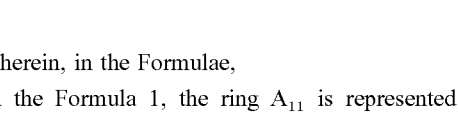

<Formula 1B> wherein, in the Formulae,
in the Formula 1, the ring $A_{11}$ is represented by the Formula 1A;

in the Formula 1, the ring $A_{12}$ is represented by the Formula 1B;

$X_{11}$ is $N-[(L_{11})_{a11}-(R_{11})_{b11}]$, S, O, S(=O), S(=O)$_2$, C(=O), C(R$_{13}$)(R$_{14}$), Si(R$_{13}$)(R$_{14}$), P(R$_{13}$), P(=O)R$_{13}$ or C=N(R$_{13}$);

$X_{12}$ is $N-[(L_{12})_{a12}-(R_{12})_{b12}]$, S, O, S(=O), S(=O)$_2$, C(=O), C(R$_{15}$)(R$_{16}$), Si(R$_{15}$)(R$_{16}$), P(R$_{15}$), P(=O)R$_{15}$ or C=N(R$_{15}$);

$X_1$ is $N-[(L_1)_{a1}-(R_1)_{b1}]$, S, O, S(=O), S(=O)$_2$, C(=O), Si(R$_5$)(R$_6$), P(R$_5$), P(=O)R$_5$ or C=N(R$_5$);

$L_1$ to $L_4$, $L_{11}$ and $L_{12}$ are independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic heterocondensed polycyclic group;

a1 to a4, a11 and a12 are independently selected from integers of 0 to 3;

$R_1$ to $R_6$, $R_{11}$ to $R_{16}$ and $R_{21}$ to $R_{30}$ are independently one of hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —N(Q$_1$)(Q$_2$), —Si(Q$_3$)(Q$_4$)(Q$_5$), —B(Q$_6$)(Q$_7$), or one of the groups represented by the Formula 2A to Formula 2F, provided that the $R_1$ to $R_6$ are not one of the groups represented by the Formula 2A, Formula 2B, Formula 2C, Formula 2D, Formula 2E, or Formula 2F, and provided that at least one of $R_{11}$ to $R_{16}$ or $R_{21}$ to $R_{30}$ is a group represented by one of the Formula 2A, Formula 2B, Formula 2C, Formula 2D, Formula 2E, or Formula 2F;

b1 to b4, b11 and b12 are independently selected from integers of 1 to 3;

i) in the Formula 1, when $X_{11}$ is $N-[(L_{11})_{a11}-(R_{11})_{b11}]$ and $X_{12}$ is not $N-[(L_{12})_{a12}-(R_{12})_{b12}]$, in the Formula 1, at least one of b11 $R_{11}$'s and $R_{21}$ to $R_{30}$ is selected from the group represented by the Formula 2A to the group represented by the Formula 2F;

ii) in the Formula 1, when $X_{11}$ is not $N-[(L_{11})_{a11}-(R_{11})_{b11}]$ and $X_{12}$ is $N-[(L_{12})_{a12}-(R_{12})_{b12}]$, in the Formula 1, at least one of b12 $R_{12}$'s and $R_{21}$ to $R_{30}$ is selected from the group represented by the Formula 2A to the group represented by the Formula 2F; and iii) in the Formula 1, when $X_{11}$ is $N-[(L_{11})_{a11}-(R_{11})_{b11}]$ and $X_{12}$ is $N-[(L_{12})_{a12}-(R_{12})_{b12}]$, in the Formula 1, at least one of b11 $R_{11}$'s, and b12 $R_{12}$'s and $R_{21}$ to $R_{30}$ is selected from the group represented by the Formula 2A to the group represented by the Formula 2F;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group and substituted monovalent non-aromatic heterocondensed polycyclic group is, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N(Q$_{11}$)(Q$_{12}$), —Si(Q$_{13}$)(Q$_{14}$)(Q$_{15}$) and —B(Q$_{16}$)(Q$_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —N($Q_{21}$)($Q_{22}$), —Si($Q_{23}$)($Q_{24}$)($Q_{25}$) and —B($Q_{26}$)($Q_{27}$); or —N($Q_{31}$)($Q_{32}$), —Si($Q_{33}$)($Q_{34}$)($Q_{35}$) or —B($Q_{36}$)($Q_{37}$);

wherein the $Q_1$ to $Q_7$, $Q_1$ to $Q_{17}$, $Q_{21}$ to $Q_{27}$ and $Q_{31}$ to $Q_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group.

2. The condensed cyclic compound of claim 1, wherein $X_{11}$ is N-[$(L_{11})_{a11}$-$(R_{11})_{b11}$], S or O;
$X_{12}$ is N-[$(L_{12})_{a12}$-$(R_{12})_{b12}$], S or O; and
$X_1$ is N-[$(L_1)_{a1}$-$(R_1)_{b1}$], S or O.

3. The condensed cyclic compound of claim 1, wherein the $L_1$ to $L_4$, $L_{11}$ and $L_{12}$ are independently represented by one of Formulae 2-1 to 2-13:

Formula 2-1
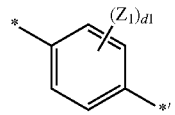

Formula 2-2
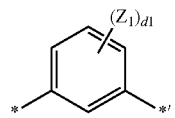

Formula 2-3
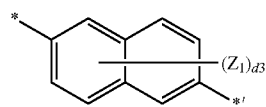

Formula 2-4
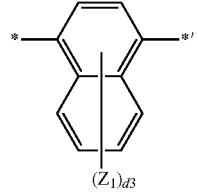

Formula 2-5
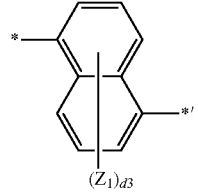

Formula 2-6
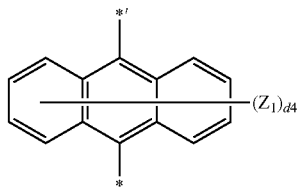

Formula 2-7
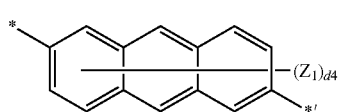

Formula 2-8
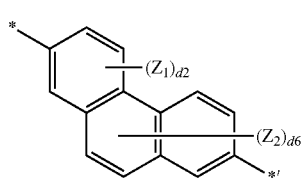

Formula 2-9
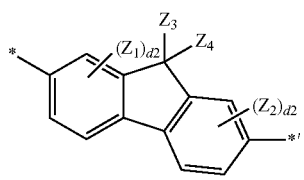

Formula 2-10
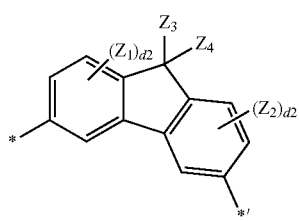

Formula 2-11
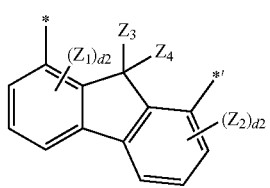

Formula 2-12
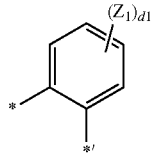

Formula 2-13
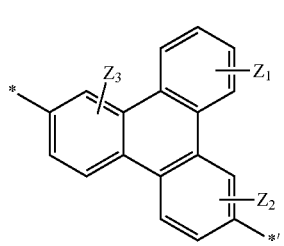

wherein, in the Formulae 2-1 to 2-13,
$Z_1$ to $Z_4$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group or —Si($Q_{33}$)($Q_{34}$)($Q_{35}$);

wherein the $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, quinazolinyl group or quinoxalinyl group; and d1 is selected from integers of 1 to 4, d2 is selected from integers of 1 to 3, d3 is selected from integers of 1 to 6, d4 is selected from integers of 1 to 8, d6 is selected from integers of 1 to 5, * and *' indicate bonding sites with a neighboring atom.

4. The condensed cyclic compound of claim 1, wherein $R_1$ to $R_6$, $R_{11}$ to $R_{16}$ and $R_{21}$ to $R_{30}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

a phenyl group, a pentalenyl group, an indenyl group, a naphthyl group, an azulenyl group, a heptalenyl group, an indacenyl group, acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and a biphenyl group;

—Si($Q_3$)($Q_4$)($Q_5$), provided that the $R_{13}$ to $R_{16}$ and $R_5$ and $R_6$ are not —Si($Q_3$)($Q_4$)($Q_5$); or one of the groups represented by the Formula 2A to Formula 2F, provided that the $R_1$ to $R_6$ are not the group represented by the Formula 2A, Formula 2B, Formula 2C, Formula 2D, Formula 2E, or Formula 2F, and provided that at least one of $R_{11}$ to $R_{16}$ or $R_{21}$ to $R_{30}$ is a group represented by one of the Formula 2A, Formula 2B, Formula 2C, Formula 2D, Formula 2E, or Formula 2F;

wherein the $Q_3$ to $Q_5$ and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group.

5. The condensed cyclic compound of claim 1, wherein the $R_1$ to $R_6$, $R_{11}$ to $R_{16}$ and $R_{21}$ to $R_{30}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group or a $C_1$-$C_{20}$ alkoxy group;

a $C_1$-$C_{20}$ alkyl group or a $C_1$-$C_{20}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof and a phosphoric acid or a salt thereof;

one of the following Formulae 4-1 to 4-31;

—Si($Q_3$)($Q_4$)($Q_5$), provided that the $R_{13}$ to $R_{16}$ and $R_5$ to $R_6$ are not —Si($Q_3$)($Q_4$)($Q_5$); or one of the groups represented by the Formula 2A to Formula 2F, provided that $R_1$ to $R_6$ are not one of the groups represented by the Formula 2A, Formula 2B, Formula 2C, Formula 2D, Formula 2E, or Formula 2F, and provided that at least one of $R_{11}$ to $R_{16}$ or $R_{21}$ to $R_{30}$ is a group represented by one of the Formula 2A, Formula 2B, Formula 2C, Formula 2D, Formula 2E, or Formula 2F,

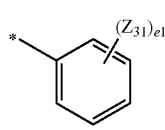

Formula 4-1

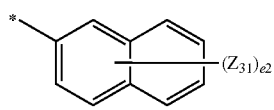

Formula 4-2

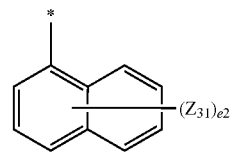

Formula 4-3

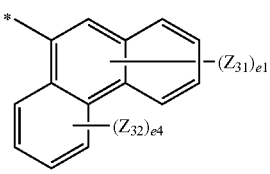

Formula 4-4

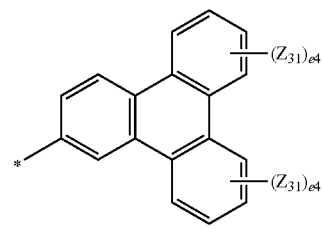

Formula 4-5

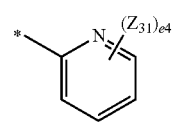

Formula 4-6

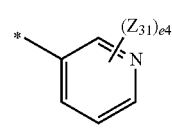

Formula 4-7

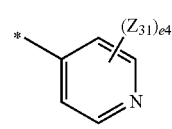

Formula 4-8

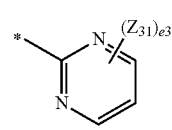

Formula 4-9

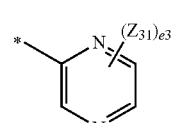

Formula 4-10

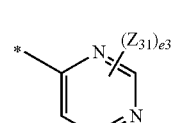

Formula 4-11

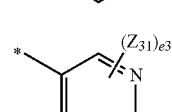

Formula 4-12

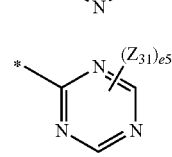

Formula 4-13

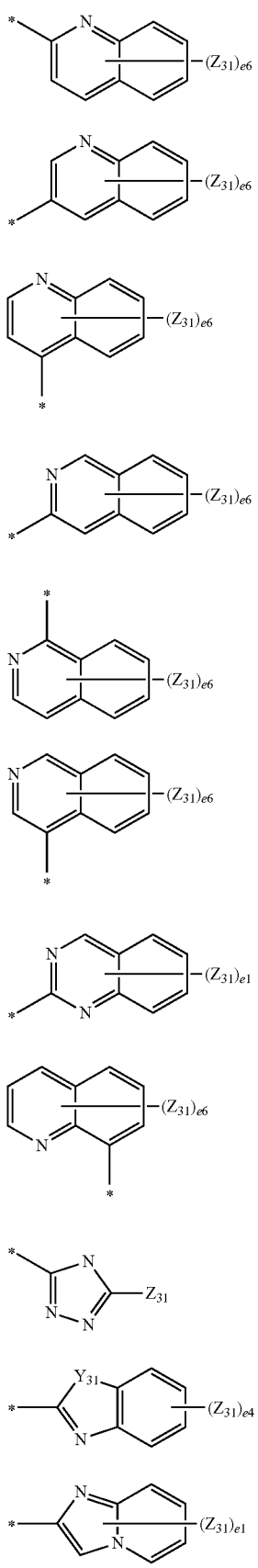

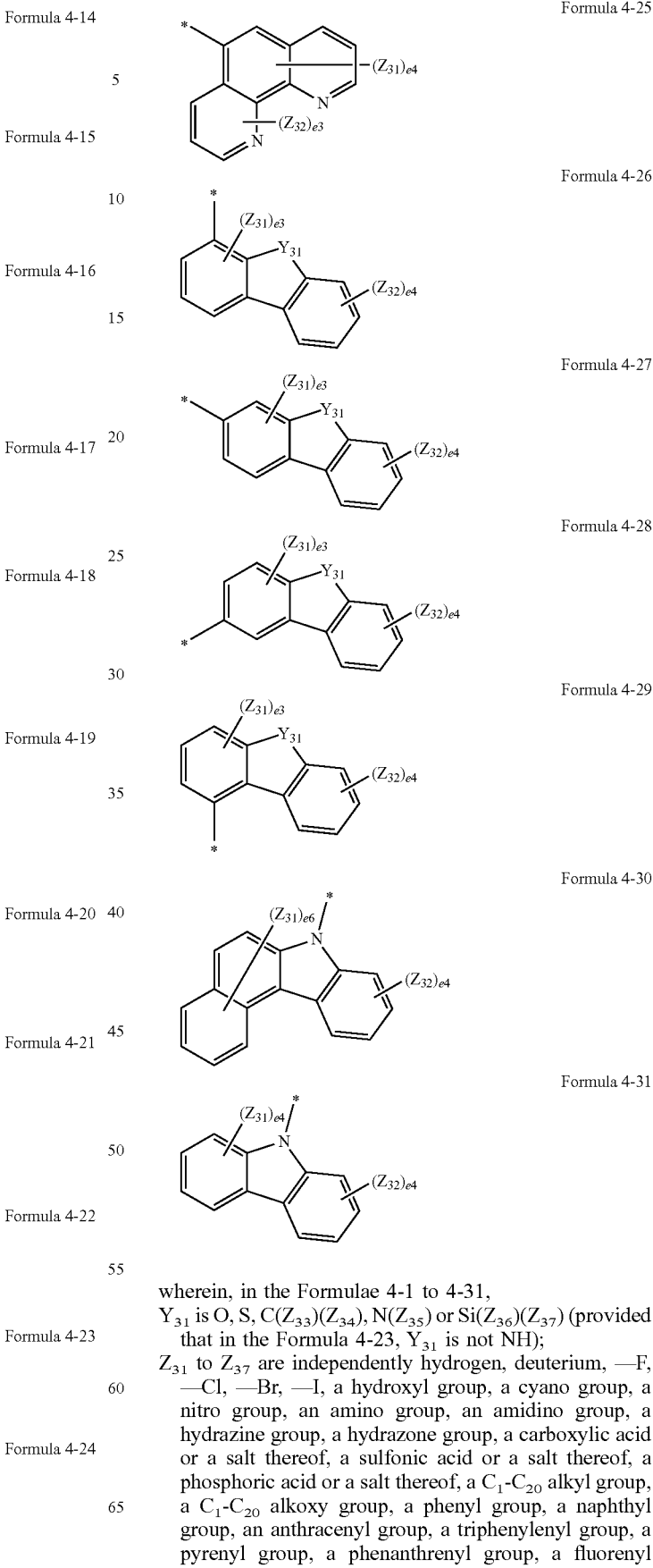

wherein, in the Formulae 4-1 to 4-31,
Y$_{31}$ is O, S, C(Z$_{33}$)(Z$_{34}$), N(Z$_{35}$) or Si(Z$_{36}$)(Z$_{37}$) (provided that in the Formula 4-23, Y$_{31}$ is not NH);
Z$_{31}$ to Z$_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, a C$_1$-C$_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group, a quinoxalinyl group, a biphenyl group or —Si($Q_{33}$)($Q_{34}$)($Q_{35}$);

wherein the $Q_3$ to $Q_5$ and $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a triphenylenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group;

e1 is selected from integers of 1 to 5, e2 is selected from integers of 1 to 7, e3 is selected from integers of 1 to 3, e4 is selected from integers of 1 to 4, e5 is 1 or 2, e6 is selected from integers of 1 to 6, and * indicates a bonding site with a neighboring atom.

6. The condensed cyclic compound of claim 1, wherein $R_2$ in the Formula 2A and 2B, $R_3$ in the Formulae 2C and 2D, and at least one of $R_2$ and $R_3$ in the Formulae 2E and 2F is a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_{33}$)($Q_{34}$)($Q_{35}$), phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group and a biphenyl group; and wherein the $Q_{33}$ to $Q_{35}$ are independently hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzothiophenyl group, a pyridinyl group, a pyrimidinyl group, a triazinyl group, a quinolinyl group, an isoquinolinyl group, a quinazolinyl group or a quinoxalinyl group.

7. The condensed cyclic compound of claim 1, which is represented by one of the following Formulae 1-1 to 1-6:

Formula 1-1
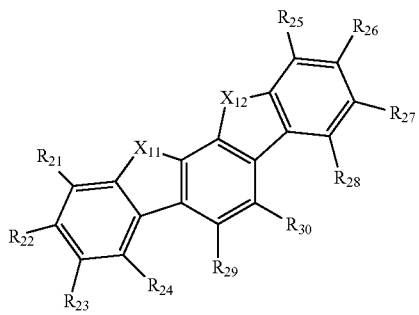

Formula 1-2
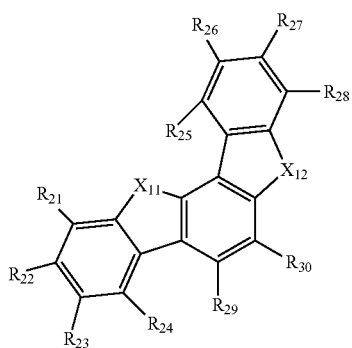

Formula 1-3
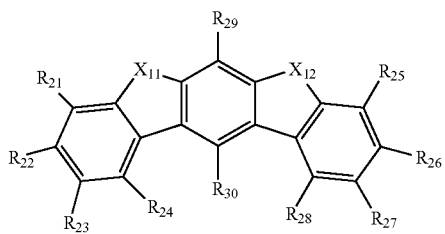

Formula 1-4
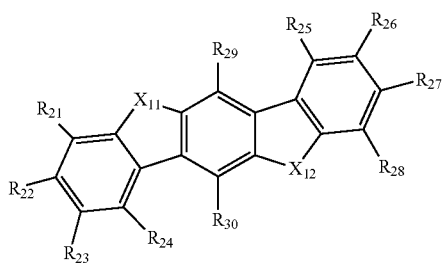

Formula 1-5
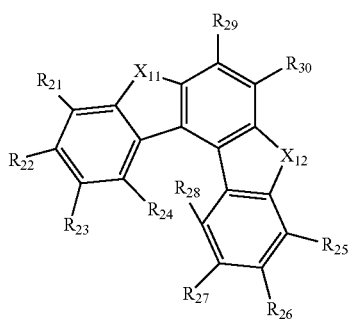

Formula 1-6
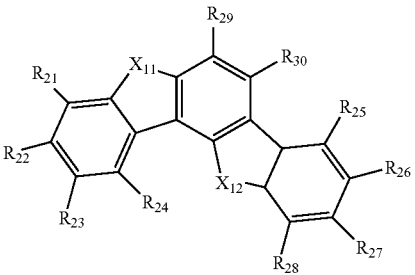

wherein, in the Formulae 1-1 to 1-6, $X_{11}$, $X_{12}$ and $R_{21}$ to $R_{30}$ are the same as in claim 1.

8. The condensed cyclic compound of claim 7, wherein the condensed cyclic compound is
   i) represented by the Formula 1-1 or 1-2, wherein in the Formulae 1-1 and 1-2, $R_{21}$ is selected from the groups represented by the Formula 2A to Formula 2F, or
   ii) represented by the Formula 1-1 or 1-6, wherein in the Formulae 1-1 and 1-6, $X_{11}$ is N-[$(L_{11})_{a11}$-$(R_{11})_{b11}$], and $R_{11}$ is selected from the groups represented by the Formulae 2A to Formula 2F.

9. The condensed cyclic compound of claim 1, which is one of the following compounds 1 to 40:

1
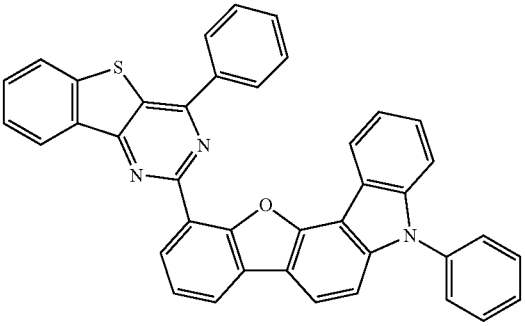

2
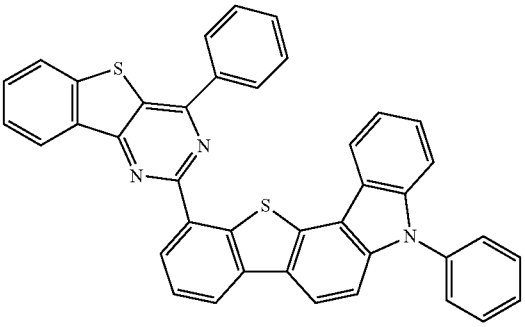

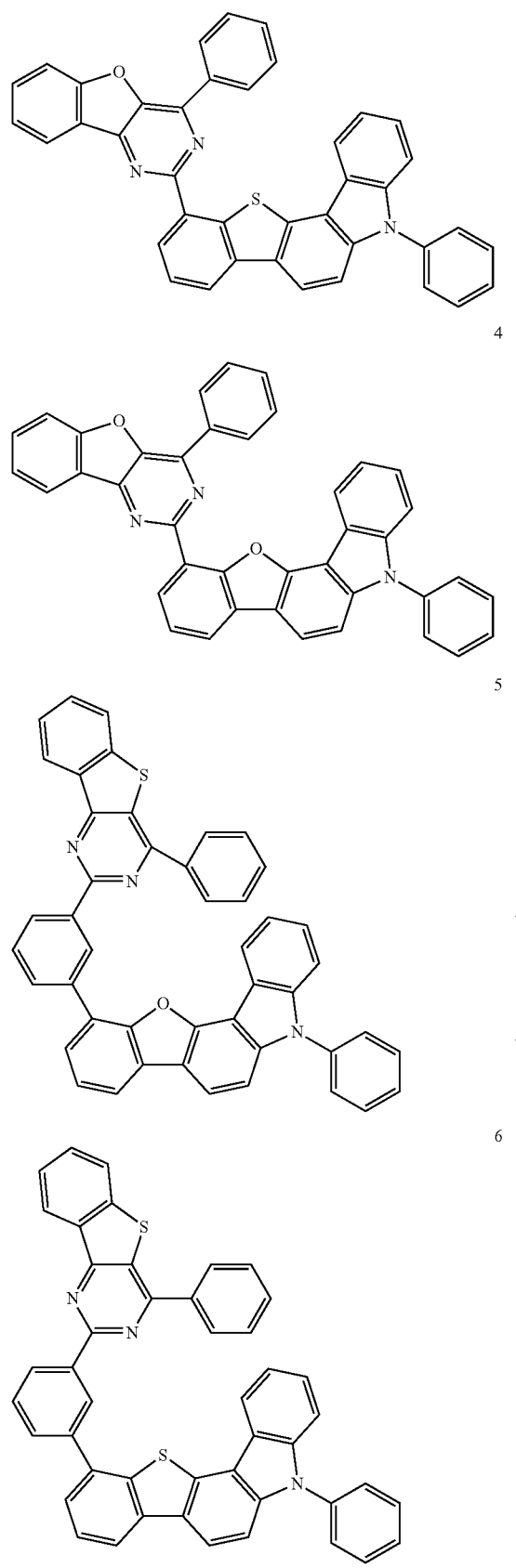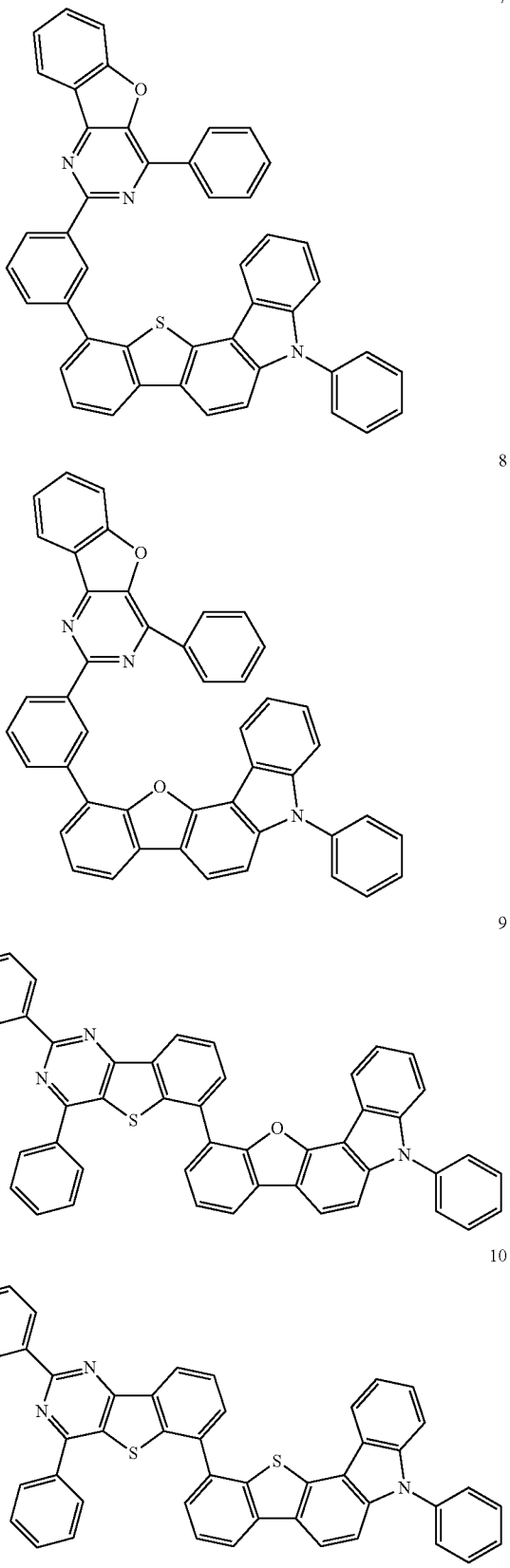

11
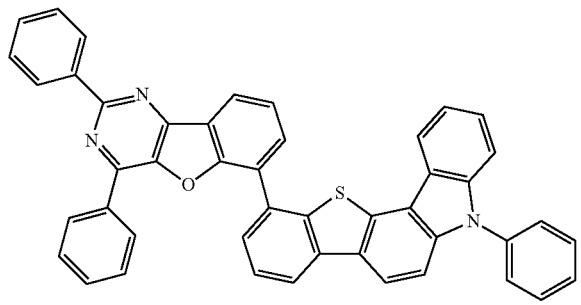
16
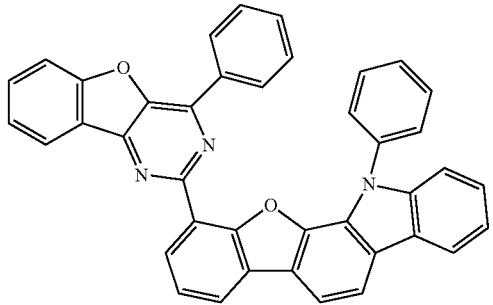
12
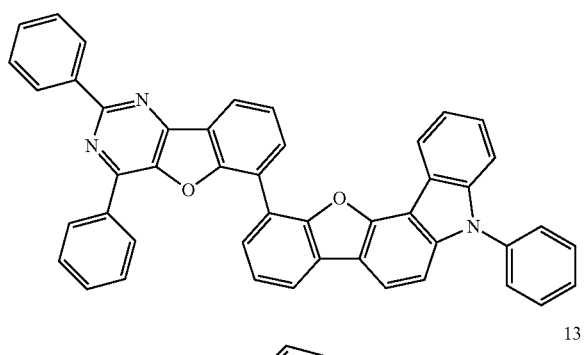
17
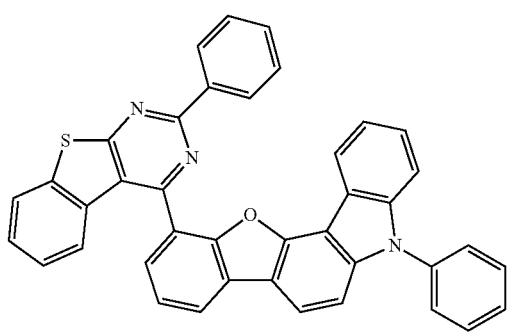
13
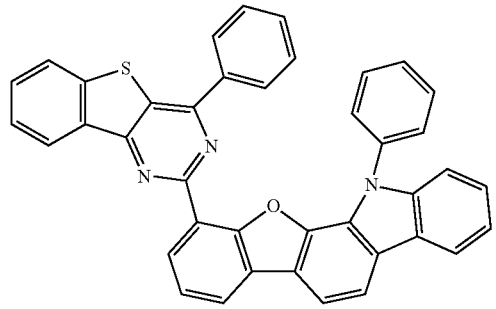
18
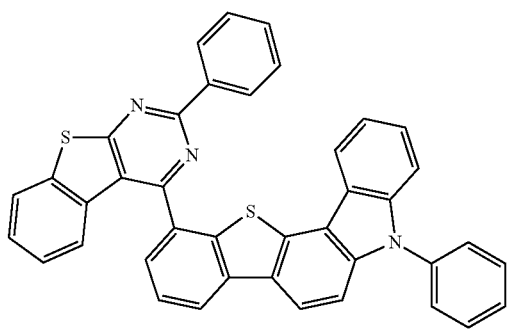
14
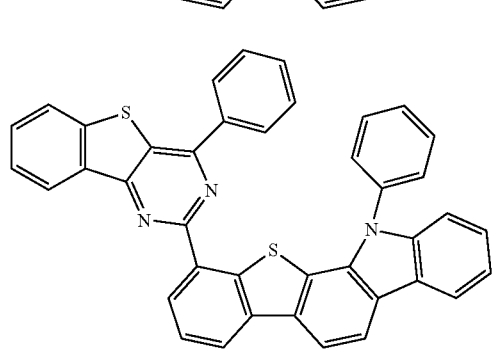
19
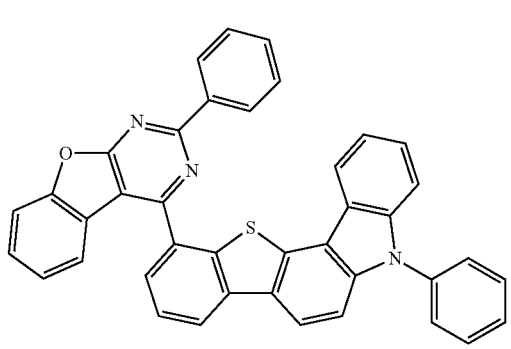
15
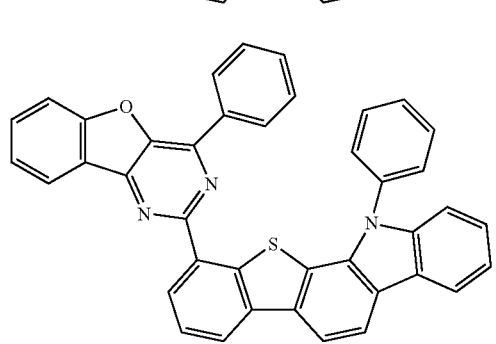

20
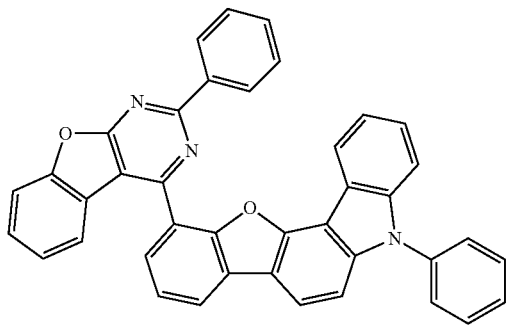
21
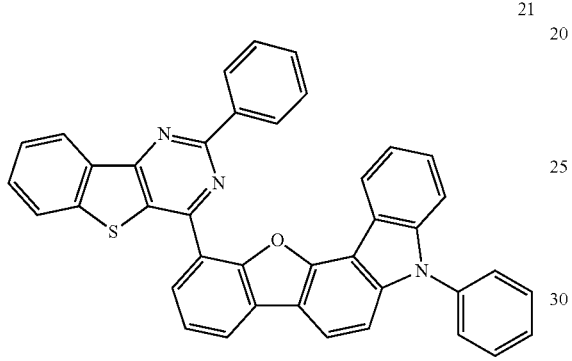
22
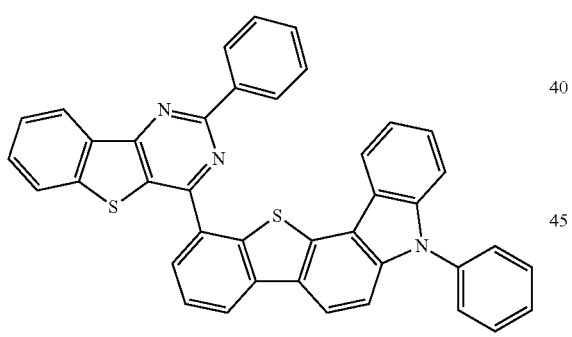
23
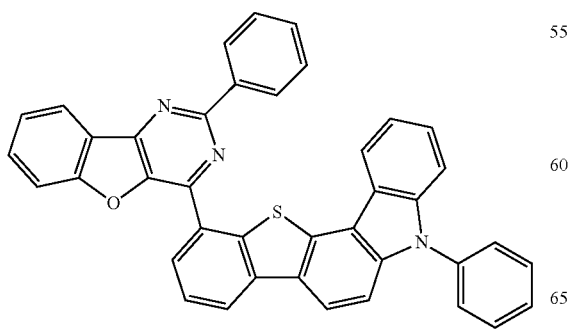
24
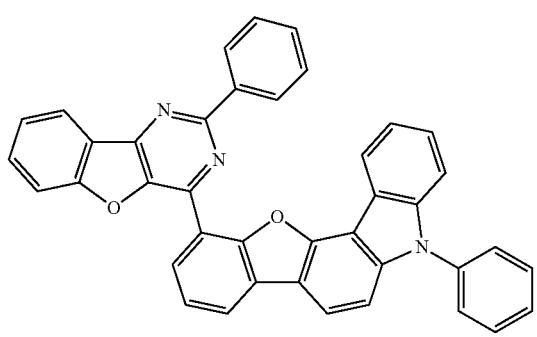
25
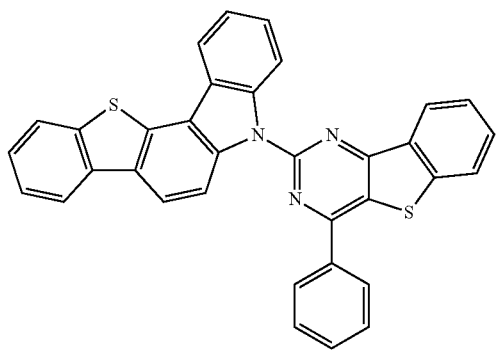
26
27
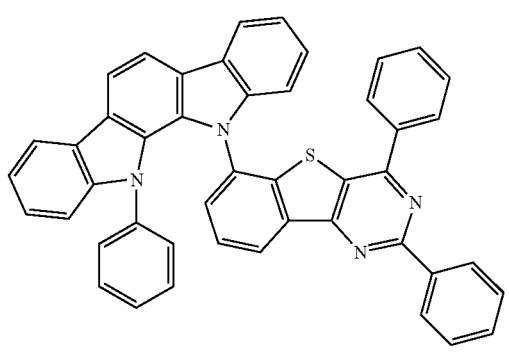

-continued
28
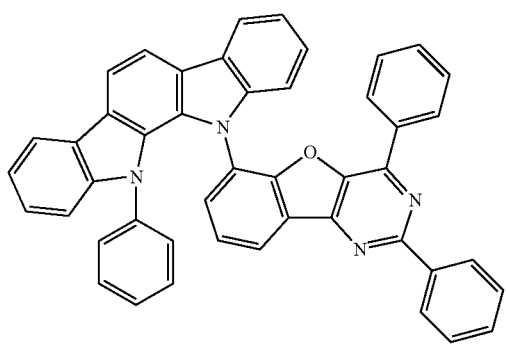
29
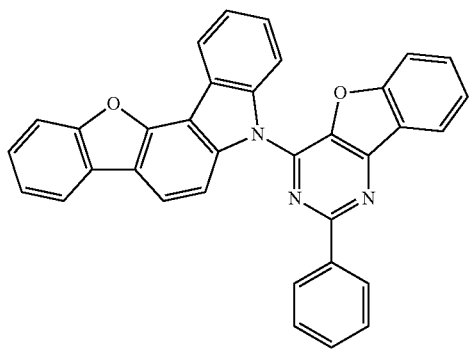
30
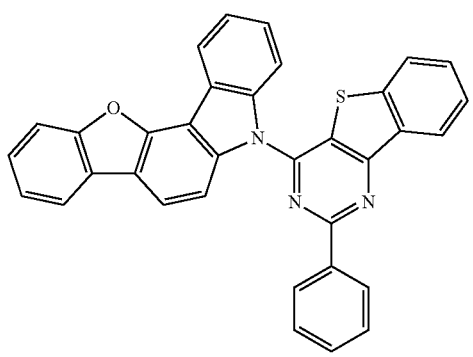
31
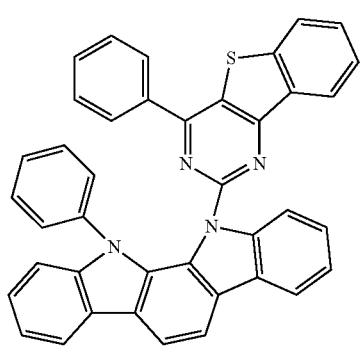
-continued
32
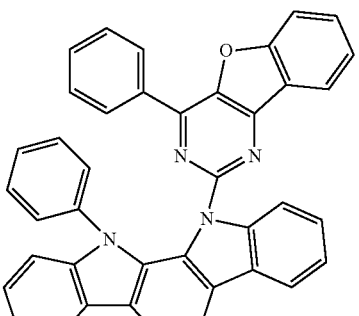
33
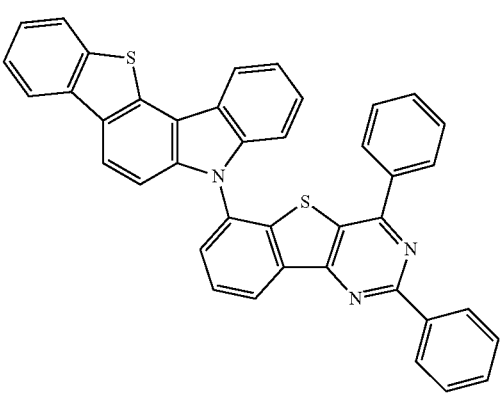
34
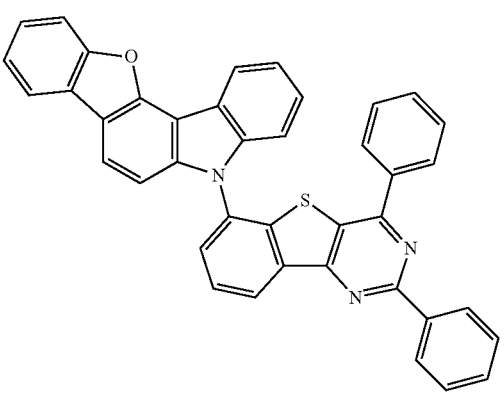
35
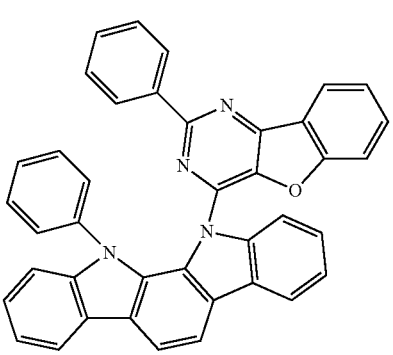

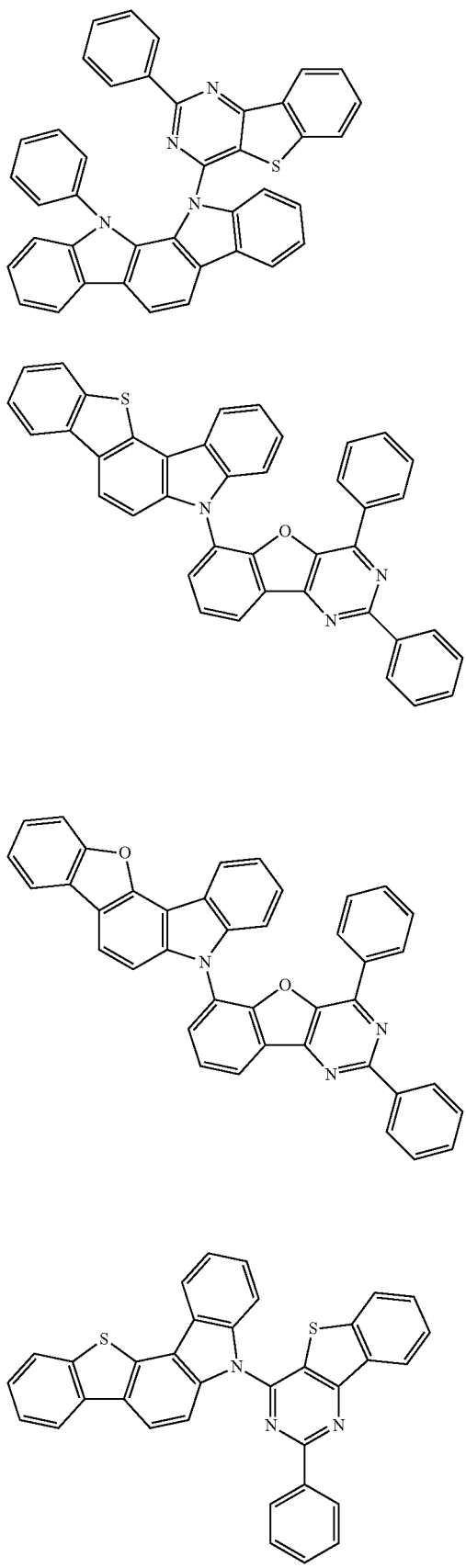

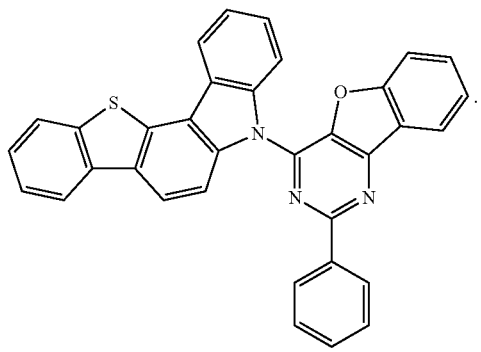

10. An organic light emitting device comprising a first electrode; a second electrode facing the first electrode; and an organic layer including an emission layer interposed between the first electrode and the second electrode; wherein the organic layer comprises the condensed cyclic compound of claim 1.

11. The organic light emitting device of claim 10, wherein the condensed cyclic compound is present in the emission layer.

12. The organic light emitting device of claim 10, wherein the emission layer comprises a first host, a second host and a dopant, the first host and the second host are different from each other, the first host comprises the condensed cyclic compound, the second host comprises at least one of a first compound represented by the following Formula 41 and a second compound represented by the following Formula 61:

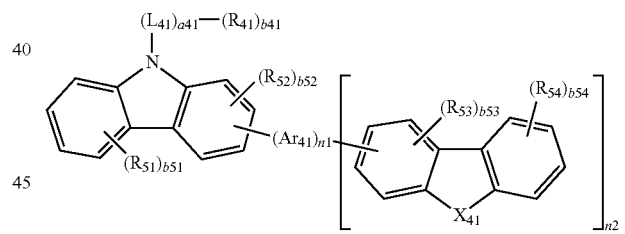

<Formula 41>

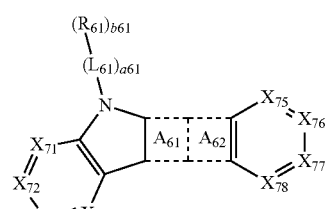

<Formula 61>

<Formula 61A>

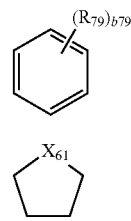

<Formula 61B> wherein, in the Formulae $X_{41}$ is $N-[(L_{42})_{a42}-(R_{42})_{b42}]$, S, O, S(=O), $S(=O)_2$, C(=O), $C(R_{43})(R_{44})$, $Si(R_{43})(R_{44})$, $P(R_{43})$, $P(=O)R_{43}$ or C=$N(R_{43})$;

in the Formula 61, the ring $A_{61}$ is represented by the Formula 61A;

in the Formula 61, the ring $A_{62}$ is represented by the Formula 61B;

$X_{61}$ is $N-[(L_{62})_{a62}-(R_{62})_{b62}]$, S, O, S(=O), $S(=O)_2$, C(=O), $C(R_{63})(R_{64})$, $Si(R_{63})(R_{64})$, $P(R_{63})$, $P(=O)R_{63}$ or C=$N(R_{63})$;

$X_{71}$ is $C(R_{71})$ or N, $X_{72}$ is $C(R_{72})$ or N, $X_{73}$ is $C(R_{73})$ or N, $X_{74}$ is $C(R_{74})$ or N, $X_{75}$ is $C(R_{75})$ or N, $X_{76}$ is $C(R_{76})$ or N, $X_{77}$ is $C(R_{77})$ or N, $X_{78}$ is $C(R_{78})$ or N;

$Ar_{41}$, $L_{41}$, $L_{42}$, $L_{61}$ and $L_{62}$ are independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic heterocondensed polycyclic group;

n1 and n2 are independently selected from integers of 0 to 3;

a41, a42, a61 and a62 are independently selected from integers of 0 to 3;

$R_{41}$ to $R_{44}$, $R_{51}$ to $R_{54}$, $R_{61}$ to $R_{64}$ and $R_{71}$ to $R_{79}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic heterocondensed polycyclic group, —$N(Q_1)(Q_2)$, —$Si(Q_3)(Q_4)(Q_5)$ or —$B(Q_6)(Q_7)$;

b41, b42, b51 to b54 b61, b62 and b79 are independently selected from integers of 1 to 3;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic heterocondensed polycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{60}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group and substituted monovalent non-aromatic heterocondensed polycyclic group is, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group or a $C_1$-$C_{60}$ alkoxy group;

a $C_1$-$C_{60}$ alkyl group, a $C_2$-$C_{60}$ alkenyl group, a $C_2$-$C_{60}$ alkynyl group or a $C_1$-$C_{60}$ alkoxy group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —$N(Q_{11})(Q_{12})$, —$Si(Q_{13})(Q_{14})(Q_{15})$ and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic heterocondensed polycyclic group each of which is substituted with at least one of deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic heterocondensed polycyclic group, —$N(Q_{21})(Q_{22})$, —$Si(Q_{23})(Q_{24})(Q_{25})$ and —$B(Q_{26})(Q_{27})$; or —$N(Q_{31})(Q_{32})$, —$Si(Q_{33})(Q_{34})(Q_{35})$ or —$B(Q_{36})(Q_{37})$;

wherein the $Q_1$ to $Q_7$, $Q_{11}$ to $Q_{17}$, $Q_{21}$ to $Q_{27}$ and $Q_{31}$ to $Q_{37}$ are independently hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group or a monovalent non-aromatic heterocondensed polycyclic group.

* * * * *

UNITED STATES PATENT AND TRADEMARK OFFICE
CERTIFICATE OF CORRECTION

PATENT NO. : 10,361,377 B2  
APPLICATION NO. : 15/102912  
DATED : July 23, 2019  
INVENTOR(S) : Hyung-Sun Kim et al.

It is certified that error appears in the above-identified patent and that said Letters Patent is hereby corrected as shown below:

On the Title Page

Item (73) (Assignee), Reads:  
"Samsung SDI Co., Ltd., Yongin-Si, Gyeonggi-Do (KR)"  
Should Read:  
"SAMSUNG SDI Co., Ltd., Yongin-Si, Gyeonggi-Do (KR); SAMSUNG ELECTRONICS CO., LTD., Suwon-Si, Gyeonggi-Do (KR)"

Signed and Sealed this  
Thirty-first Day of March, 2020

Andrei Iancu  
*Director of the United States Patent and Trademark Office*